US008708909B2

(12) United States Patent
Goertz et al.

(10) Patent No.: US 8,708,909 B2
(45) Date of Patent: Apr. 29, 2014

(54) HIGH FREQUENCY ULTRASOUND IMAGING USING CONTRAST AGENTS

(75) Inventors: David E. Goertz, Rotterdam (NL); F. Stuart Foster, Toronto (CA)

(73) Assignee: FUJIFILM VisualSonics, Inc., Toronto (CA)

( * ) Notice: Subject to any disclaimer, the term of this patent is extended or adjusted under 35 U.S.C. 154(b) by 1266 days.

(21) Appl. No.: 11/040,999

(22) Filed: Jan. 20, 2005

(65) Prior Publication Data
US 2006/0078501 A1 Apr. 13, 2006

Related U.S. Application Data

(60) Provisional application No. 60/538,174, filed on Jan. 20, 2004.

(51) Int. Cl.
*A61B 8/00* (2006.01)

(52) U.S. Cl.
USPC .......................................... 600/437; 600/407

(58) Field of Classification Search
USPC .......................................... 600/407, 437, 441
See application file for complete search history.

(56) References Cited

U.S. PATENT DOCUMENTS

| 5,307,816 | A | * | 5/1994 | Hashimoto et al. | 600/439 |
| 5,410,516 | A | * | 4/1995 | Uhlendorf et al. | 367/7 |
| 5,462,058 | A | | 10/1995 | Yamada et al. | |
| 5,678,553 | A | * | 10/1997 | Uhlendorf et al. | 600/458 |
| 5,706,819 | A | | 1/1998 | Hwang et al. | 128/662.02 |
| 5,879,303 | A | | 3/1999 | Averkiou et al. | 600/447 |
| 6,132,374 | A | * | 10/2000 | Hossack et al. | 600/443 |
| 6,676,606 | B2 | | 1/2004 | Simpson et al. | 600/458 |
| 6,680,047 | B2 | | 1/2004 | Klaveness et al. | 424/424 |
| 6,827,686 | B2 | * | 12/2004 | Szabo et al. | 600/458 |
| 6,872,180 | B2 | * | 3/2005 | Reinhardt et al. | 600/443 |

(Continued)

OTHER PUBLICATIONS

Allen, et al., "Shell waves and acoustic scattering from ultrasound contrast agents," *IEEE Trans. Ultrason., Ferroelect., Freqa. Contr.*, vol. 48, pp. 409-418, 2001.

(Continued)

*Primary Examiner* — Unsu Jung
*Assistant Examiner* — Nasir S Shahrestani
(74) *Attorney, Agent, or Firm* — Perkins Coie LLP

(57) ABSTRACT

Provided herein are compositions comprising a microbubble contrast agent, wherein at least 20% by volume of the microbubbles in the contrast agent has a size of less than 1 micron, wherein the contrast agent produces non-linear scattering when contacted by ultrasound at a frequency above 20 MHz. Provided herein are compositions comprising a microbubble contrast agent, wherein at least 10% by volume of the microbubbles in the contrast agent has a size of less than 500 nanometers, wherein the contrast agent produces non-linear scattering when contacted by ultrasound at a frequency above 20 MHz. Provided herein are compositions comprising a microbubble contrast agent, wherein at least 5% by volume of the microbubbles in the contrast agent has a size of less than 200 nanometers, wherein the contrast agent produces non-linear scattering when contacted by ultrasound at a frequency above 20 MHz. The disclosed contrast agents can be targeted contrast agents. Further provided are methods of using the compositions disclosed herein. Specifically provided are methods for producing an ultrasound image comprising: administering contrast agent to a laboratory animal; generating ultrasound at a frequency of at least 20 MHz; transmitting ultrasound at a frequency of at least 20 MHz into the subject; receiving non-linear ultrasound from the contrast agent in the subject; processing the received ultrasound to provide an image.

35 Claims, 36 Drawing Sheets

(56) References Cited

U.S. PATENT DOCUMENTS

| | | |
|---|---|---|
| 2001/0021808 A1 | 9/2001 | Shi et al. |
| 2003/0157023 A1 | 8/2003 | Roessling .................... 424/9.52 |
| 2004/0122319 A1 | 6/2004 | Mehi et al. .................... 600/443 |
| 2004/0236219 A1 | 11/2004 | Liu et al. ....................... 600/443 |
| 2006/0079775 A1 | 4/2006 | McMorrow et al. |
| 2008/0200815 A1 | 8/2008 | Van Der Steen et al. |

OTHER PUBLICATIONS

Bouakaz, et al., "Contrast superharmonic imaging: A feasibility study," Ultrasound Med. Biol. vol. 29, pp. 547-553, 2003.
Burns, et al., "Harmonic power mode Doppler using microbubble contrast agents: An improved method for small vessel flow imaging," J. Ech. Med. Ultra., vol. 16, pp. 132-142, 1994.
Cachard, et al., "Ultrasound contrast agent in intravascular echography: An in vitro study," Ultrasound Med. Biol., vol. 23, No. 5, pp. 705-717, 1997.
Cherin et al., "Experimental characterization of fundamental and second harmonic beams for a high-frequency ultrasound transducer", Ultrasound Med. Biol., vol. 28 (5), pp. 635-646, 2002.
Chin and Burns, "Experimental verification of ensemble model for scattering by microbubbles population in a contrast agent", Proc. UFFC Symp., pp. 1827-1830, 1998.
Chomas, et al., "Mechanisms of contrast agent destruction," IEEE Trans. Ultrason., Ferroelect., Freq. Contr., vol. 48, pp. 232-248, 2001.
Dayton et al. "Targeted Imaging using ultrasound" J. Magnetic Resonance Imaging 16:362-377, 2002.
de Jong, et al, "Higher harmonics of vibrating gas-filled microspheres. Part Two: Measurement," Ultrasonics, vol. 32, pp. 455-459, 1994.
de Jong, et al., "Detection procedures of ultrasound contrast agents," Ultrasonics, vol. 38, pp. 87-92, 2000.
Demos et al. "In vivo targeting of acoustically reflective liposomes for the intravascular and transvascular ultrasonic enhancement" J. American College of Cargiology 33(3), pp. 867-75, 1999.
Deng et al., "Imaging and spectrum analysis of contrast agents in the in vivo rabbit eye using very high frequency ultrasound," Ultrasound Med. Biol., vol. 24, pp. 383-394, 1998.
Deng et al., "A review of physical phenomena associated with ultrasonic contrast agents and illustrative clinical phenomena," Ultrasound Med. Biol., vol. 28, pp. 277-286, 2002.
Eatock, et al., "Numerical studies of the spectrum of low intensity ultrasound scattered by bubbles," J. Acoust. Soc. Amer., vol. 77, pp. 1692-1701, 1985.
Ellegala et al. "Imaging tumor angiogenesis with contrast ultrasound and microbubbles targeted to $\alpha_v\beta_3$" Circulation 108:336-391, 2003.
Forsberg et al., "Subharmonic imaging of contrast agents," Ultrasonics, vol. 38, pp. 93-98, Mar. 2000.
Foster et al., "Advances in ultrasound biomicroscopy", Ultrasound Med. Biol., vol. 26, pp. 1-27, 2000.
Foster et al., "A new ultrasound instrument for in vivo microimaging of mice", Ultrasound Med. Biol., pp. 1165-1172, 2002.
Goertz, "Imaging the microcirculation with High Frequency Ultrasound", PhD Thesis, University of Toronto, 2002.
Goertz et al., "High frequency nonlinear microbubble imaging", presented at the 8th European Symposium on Ultrasound Contrast Imaging, Jan. 23-24, 2003.
Goertz et al., "High frequency nonlinear B-scan imaging of microbubble contrast agents," Submitted to IEEE Trans. Ultrason., Ferroelec., Freq. Contr. vol. 52(1) pp. 65-79, 2005.
Goertz et al., "High frequency 3D color-flow imaging of the microcirculation", Ultrasound Med. Biol., vol. 29(1), pp. 39-51, 2003.

Goertz et al., "Non-linear scattering from microbubble contrast agents in the 14-40MHz Range", Proc. IEEE Ultrason. Symp., pp. 1747-1750, 2001.
Goertz et al., "High frequency nonlinear flow imaging of microbubble contrast agents" IEEE Trans. Ultrason., Ferroelec., Freq. Contr. vol. 52(3) pp. 495-502, 2005.
Goertz, et al., "The effect of bubble size on non-linear scattering at high frequencies," in Proc. IEEE Ultrason. Symp., 2003, pp. 1503-1506.
Goodsell "The molecular perspective: VEGF and angiogenesis" The Oncologist 7(6) pp. 569-570, 2002.
Gorce, et al., "Influence of bubble size distribution on the echogenicity of ultrasound contrast agents. A study of SonoVue™, ", Invest. Radiol. vol. 35, pp. 661-671, Nov. 2000.
Hope-Simpson et al., "Pulse inversion Doppler: a new method for detecting non-linear echoes from microbubble contrast agents," Ultrason., Ferroelec, Freq. Contr., vol. 46, pp. 372-382, 1999.
Kilbanov, et al., "Targeting of ultrasound contrast material. An in vitro feasibility study," Acta. Radiol., vol. 38, Suppl. 412 pp. 113-120, 1997.
Lanza, et al., "Targeted ultrasonic contrast agents for molecular imging and therapy," Prog. Cardiovasc. Dis., vol. 44, pp. 13-31, 2001.
Lee and Hamilton, "Time-domain modeling of pulsed finite-amplitude sound beams," J. Acoust Soc. Amer., vol. 97, pp. 906-917, 1995.
Li et al. "A digital ultrasonic system for small animal imaging" Ultrasonic Imaging 26:85-99, 2004.
Lindner "Microbubbles in medical imaging: current applications and future directions" Nature Reviews 3:527-532, 2004.
Lindner et al. "Ultrasound assessment of inflammation and renal tissue injury with microbubbles targeted to P-selection" Circulation 104:2107-2112, 2001.
Loupas et al., "An axial velocity estimator for ultrasound blood flow imaging based on a full evaluation of the Doppler equation using a 2-dimensional autocorrelation approach," IEEE Trans. Ultrason., Ferroelec., Freq. Contr., vol. 42, pp. 672-688, 1995.
Loupas et al., "Experimental evaluation of velocity and power estimation for ultrasound blood flow imaging by means of a two-dimensional autocorrelation approach," IEEE Trans. Ultrason., Ferroelec., Freq. Contr., vol. 42, pp. 689-699, 1995.
Lu et al. "Targeted in vivo labeling of receptors for vascular endothelial growth factor" Circulation 108:97-103, 2003.
Miller, "Ultrasonic detection of bubbles by their second harmonic emissions," Ultrasonics, vol. 19, pp. 217-224, 1981.
Moran, et al., "In vitro acoustic characterization of ultrasonic contrast agtents at 30 MHz," Ultrasound Med. Biol., vol. 28, pp. 785-791, 2002.
Powers, et al., "Imaging instrumentation for ultrasound contrast agents," in Advances in Echo Imaging Using Contrast Enhancement. N.C. Nanda, S reinhard, and B.B. Goldberg, Eds. Norwell, MA: Kluwer, 1997.
Prosperetti, "Nonlinear oscillations of gas bubbles in liquids: Transient solutions and the connection between harmonic signal and cavitation," J. Acoust Soc. Amer., vol. 57, pp. 810-821, 1975.
Ryan and Foster, "Tissue equivalent vessel phantoms for intravascular ultrasound", Ultrasound in Medicine & Biology, vol. 23, pp. 261-273, 1997.
Shankar, et al., "Advantages of subharmonic over second harmonic backscatter for contrast-to-tissue enhancement," Ultrasound Med. Biol., vol. 24, pp. 395-399, 1998.
Shankar, et al., "Subharmonic backscattering from ultrasound contrast agents," J. Acoust. Soc. Amer., vol. 106, pp. 2104-2110, 1999.
Sherar and Foster, The design and fabrication of high frequency poly (vinylidene fluoride) transducers, Ultrason. Imaging, vol. 11, pp. 75-94, 1989.
Shi, et al., "Ultrasonic characterization of the nonlinear properties of contrast microbubbles," Ultrasound Med. Biol., vol. 26, pp. 93-104, 2000.
Shi, et al., "Subharmonic imaging with microbuble contrast agents; Initial results," Ultrason. Imag., vol. 21. pp. 79-94, 1999.
Szabo et al. "Effects of nonlinearity on the estimation of in situ values of acoustic output parameters," Ultrasound Med. Biol., vol. 18, pp. 33-41, 1999.

(56) References Cited

OTHER PUBLICATIONS

Uhlendorf, et al., "Nonlinear acoustic response of coated microbubbles in diagnostic ultrasound," in *Proc. IEEE Ultrason. Symp.*, 1994, pp. 1559-1562.

Unger, et al., "Gas-filled lipid bilayers as ultrasound contrast agents," *Invest. Radiol.*, vol. 29, pp. S134-S136, 1994.

Verbeek et al. "Baseband velocity estimation for second-harmonic signals exploiting the invariance of the doppler equation," *IEEE T. Bio-med. Eng.*, vol. 45 (10), pp. 1217-1226, Oct. 1998.

Villanueva et al. "Microbubbles targeted to intercellular adhesion molecule-1 bind to activated coronary artery endothelial cells" *Circulation* 98: 1-5, 1998.

Weller et al. "Ultrasound imaging of acute cardiac transplant rejection with microbubbles targeted to intercellular adhesion molecule-1" *Circulation* 108:218-224, 2003.

Weller et al. "Modulating targeted adhesion of an ultrasound contrast agent to dysfunctional endothelium" *Ann. of Biomed. Eng.* 30:1012-1019, 2002.

Unger, et al., "Microbubbles in molecular imaging and therapy," *MedicaMundi*, 47:1 Apr. 2003, pp. 58-65.

Goertz, et al., "High Frequency Nonlinear Imaging of Microbubbles," *8th European Symposium on Ultrasound Contrast Imaging* (Jan. 23, 2003).

Foster et al., "High Frequency ultrasound Imaging: From Man to Mouse," *Ultrasonics Symposium* 2:1633-1638 (2000).

\* cited by examiner

SIZE STATISTICS REPORT BY INTENSITY

SAMPLE DETAILS
NAME: DEFINITY
FILENAME: DEFINITY

SOP: STANDARD – GLASS CUVETTE.SOP

| SIZE | MEAN % INTENSITY | STD DEV % INTENSITY | SIZE | MEAN % INTENSITY | STD DEV % INTENSITY | SIZE | MEAN % INTENSITY | STD DEV % INTENSITY | SIZE | MEAN % INTENSITY | STD DEV % INTENSITY |
|---|---|---|---|---|---|---|---|---|---|---|---|
| 10 | 0 | 0 | 53.06 | 0 | 0 | 281.5 | 3.002 | 0.5342 | 1494 | 4.917 | 2.474 |
| 10.97 | 0 | 0 | 58.21 | 0 | 0 | 308.8 | 4.378 | 0.9245 | 1639 | 5.237 | 2.928 |
| 12.04 | 0 | 0 | 63.86 | 0 | 0 | 338.8 | 5.319 | 1.413 | 1798 | 5.268 | 3.123 |
| 13.21 | 0 | 0 | 70.07 | 0 | 0 | 371.8 | 5.616 | 1.656 | 1972 | 5.009 | 3.023 |
| 14.49 | 0 | 0 | 76.88 | 0 | 0 | 407.9 | 5.271 | 1.605 | 2164 | 4.504 | 2.665 |
| 15.9 | 0 | 0 | 84.34 | 0 | 0 | 447.5 | 4.457 | 1.398 | 2374 | 3.827 | 2.145 |
| 17.44 | 0 | 0 | 92.54 | 0 | 0 | 491 | 3.437 | 1.283 | 2605 | 3.086 | 1.596 |
| 19.14 | 0 | 0 | 101.5 | 0 | 0 | 538.7 | 2.48 | 1.406 | 2858 | 2.389 | 1.198 |
| 20.99 | 0 | 0 | 111.4 | 0 | 0 | 591 | 1.781 | 1.666 | 3136 | 1.825 | 1.095 |
| 23.03 | 0 | 0 | 122.2 | 0 | 0 | 648.4 | 1.405 | 1.935 | 3440 | 1.44 | 1.206 |
| 25.27 | 0 | 0 | 134.1 | 0 | 0 | 711.4 | 1.248 | 2.19 | 3774 | 1.214 | 1.367 |
| 27.73 | 0 | 0 | 147.1 | 0 | 0 | 780.5 | 1.244 | 2.336 | 4141 | 1.037 | 1.502 |
| 30.42 | 0 | 0 | 161.4 | 0 | 0 | 856.3 | 1.378 | 2.316 | 4543 | 0.8691 | 1.476 |
| 33.37 | 0 | 0 | 177.1 | 0.01888 | 0.04221 | 939.5 | 1.676 | 2.117 | 4985 | 0.669 | 1.234 |
| 36.62 | 0 | 0 | 194.3 | 0.09819 | 0.2195 | 1031 | 2.189 | 1.749 | 5469 | 0.4207 | 0.7805 |
| 40.17 | 0 | 0 | 213.1 | 0.2205 | 0.4931 | 1131 | 2.875 | 1.386 | 6000 | 0 | 0 |
| 44.08 | 0 | 0 | 233.9 | 0.6069 | 0.705 | 1241 | 3.636 | 1.402 | | | |
| 48.36 | 0 | 0 | 256.6 | 1.595 | 0.6567 | 1361 | 4.355 | 1.881 | | | |

FIG. 1

SIZE STATISTICS REPORT BY VOLUME

SAMPLE DETAILS
NAME: DEFINITY
FILENAME: DEFINITY

SOP: STANDARD – GLASS CUVETTE.SOP

| SIZE | MEAN % VOLUME | STD DEV % VOLUME |
|---|---|---|
| 10 | 0 | 0 |
| 10.97 | 0 | 0 |
| 12.04 | 0 | 0 |
| 13.21 | 0 | 0 |
| 14.49 | 0 | 0 |
| 15.9 | 0 | 0 |
| 17.44 | 0 | 0 |
| 19.14 | 0 | 0 |
| 20.99 | 0 | 0 |
| 23.03 | 0 | 0 |
| 25.27 | 0 | 0 |
| 27.73 | 0 | 0 |
| 30.42 | 0 | 0 |
| 33.37 | 0 | 0 |
| 36.62 | 0 | 0 |
| 40.17 | 0 | 0 |
| 44.08 | 0 | 0 |
| 48.36 | 0 | 0 |

| SIZE | MEAN % VOLUME | STD DEV % VOLUME |
|---|---|---|
| 53.06 | 0 | 0 |
| 58.21 | 0 | 0 |
| 63.86 | 0 | 0 |
| 70.07 | 0 | 0 |
| 76.88 | 0 | 0 |
| 84.34 | 0 | 0 |
| 92.54 | 0 | 0 |
| 101.5 | 0 | 0 |
| 111.4 | 0 | 0 |
| 122.2 | 0 | 0 |
| 134.1 | 0 | 0 |
| 147.1 | 0 | 0 |
| 161.4 | 0.000218 | 0.0004874 |
| 177.1 | 0.001565 | 0.003499 |
| 194.3 | 0.005135 | 0.01148 |
| 213.1 | 0.01524 | 0.02317 |
| 233.9 | 0.04884 | 0.03367 |
| 256.6 | 0.1357 | 0.04067 |

| SIZE | MEAN % VOLUME | STD DEV % VOLUME |
|---|---|---|
| 281.5 | 0.3078 | 0.06954 |
| 308.8 | 0.599 | 0.1589 |
| 338.8 | 1.06 | 0.3173 |
| 371.8 | 1.799 | 0.5627 |
| 407.9 | 2.843 | 0.8846 |
| 447.5 | 3.29 | 1.029 |
| 491 | 2.349 | 0.787 |
| 538.7 | 1.075 | 0.4777 |
| 591 | 0.4827 | 0.3763 |
| 648.4 | 0.4121 | 0.5477 |
| 711.4 | 0.8852 | 1.532 |
| 780.5 | 1.346 | 2.396 |
| 856.3 | 1.007 | 1.665 |
| 939.5 | 0.8331 | 0.862 |
| 1031 | 1.962 | 1.154 |
| 1131 | 2.894 | 1.382 |
| 1241 | 3.404 | 1.439 |
| 1361 | 4.499 | 2.197 |

| SIZE | MEAN % VOLUME | STD DEV % VOLUME |
|---|---|---|
| 1494 | 5.081 | 2.713 |
| 1639 | 5.78 | 3.382 |
| 1798 | 6.9 | 4.164 |
| 1972 | 7.097 | 4.291 |
| 2164 | 6.911 | 4.009 |
| 2374 | 6.805 | 3.686 |
| 2605 | 5.746 | 2.816 |
| 2858 | 4.443 | 2.011 |
| 3136 | 3.852 | 2.05 |
| 3440 | 3.485 | 2.596 |
| 3774 | 3.247 | 3.382 |
| 4141 | 2.952 | 3.955 |
| 4543 | 2.577 | 4.12 |
| 4985 | 2.171 | 3.806 |
| 5469 | 1.333 | 2.4 |
| 6000 | 0.3675 | 0.6636 |

FIG. 2

SIZE STATISTICS REPORT BY NUMBER

SAMPLE DETAILS
NAME: DEFINITY
FILENAME: DEFINITY

SOP: STANDARD – GLASS CUVETTE.COP

| SIZE | MEAN % NUMBER | STD DEV % NUMBER | SIZE | MEAN % NUMBER | STD DEV % NUMBER | SIZE | MEAN % NUMBER | STD DEV % NUMBER | SIZE | MEAN % NUMBER | STD DEV % NUMBER |
|---|---|---|---|---|---|---|---|---|---|---|---|
| 10 | 0 | 0 | 53.06 | 0 | 0 | 281.5 | 5.38 | 1.271 | 1494 | 0.6532 | 0.3501 |
| 10.97 | 0 | 0 | 58.21 | 0 | 0 | 308.8 | 7.966 | 1.82 | 1639 | 0.5339 | 0.3212 |
| 12.04 | 0 | 0 | 63.86 | 0 | 0 | 338.8 | 10.7 | 2.659 | 1798 | 0.4889 | 0.3071 |
| 13.21 | 0 | 0 | 70.07 | 0 | 0 | 371.8 | 13.73 | 3.391 | 1972 | 0.3875 | 0.2457 |
| 14.49 | 0 | 0 | 76.88 | 0 | 0 | 407.9 | 16.61 | 3.677 | 2164 | 0.2834 | 0.1722 |
| 15.9 | 0 | 0 | 84.34 | 0 | 0 | 447.5 | 15.56 | 3.129 | 2374 | 0.2111 | 0.1167 |
| 17.44 | 0 | 0 | 92.54 | 0 | 0 | 491 | 9.184 | 2.07 | 2605 | 0.1412 | 0.06692 |
| 19.14 | 0 | 0 | 101.5 | 0 | 0 | 538.7 | 3.315 | 1.307 | 2858 | 0.08178 | 0.03123 |
| 20.99 | 0 | 0 | 111.4 | 0 | 0 | 591 | 1.115 | 0.9207 | 3136 | 0.05439 | 0.02588 |
| 23.03 | 0 | 0 | 122.2 | 0 | 0 | 648.4 | 0.6971 | 0.9925 | 3440 | 0.03845 | 0.02997 |
| 25.27 | 0 | 0 | 134.1 | 0 | 0 | 711.4 | 1.08 | 1.971 | 3774 | 0.02813 | 0.03231 |
| 27.73 | 0 | 0 | 147.1 | 0 | 0 | 780.5 | 1.416 | 2.672 | 4141 | 0.02034 | 0.02984 |
| 30.42 | 0 | 0 | 161.4 | 0.02056 | 0.04596 | 856.3 | 0.9008 | 1.623 | 4543 | 0.01385 | 0.02374 |
| 33.37 | 0 | 0 | 177.1 | 0.1217 | 0.2722 | 939.5 | 0.4571 | 0.5765 | 4985 | 0.009078 | 0.0169 |
| 36.62 | 0 | 0 | 194.3 | 0.3255 | 0.728 | 1031 | 0.7206 | 0.5329 | 5469 | 0.004628 | 0.008833 |
| 40.17 | 0 | 0 | 213.1 | 0.6919 | 1.192 | 1131 | 0.8945 | 0.5144 | 6000 | 0.001116 | 0.002136 |
| 44.08 | 0 | 0 | 233.9 | 1.531 | 1.399 | 1241 | 0.7604 | 0.3442 | | | |
| 48.36 | 0 | 0 | 256.6 | 3.13 | 1.31 | 1361 | 0.7343 | 0.3611 | | | |

FIG. 3

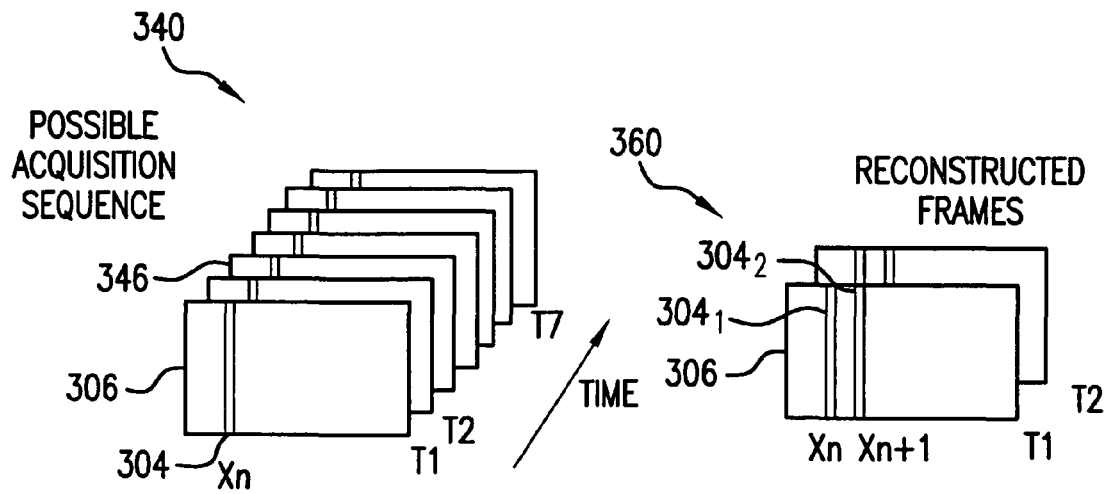
FIG.8C
FIG.8D
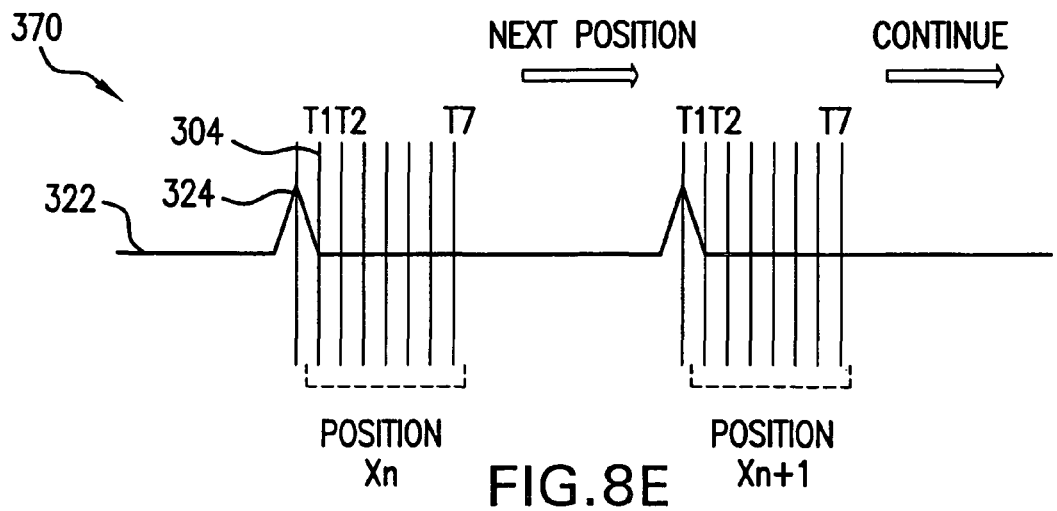
FIG.8E

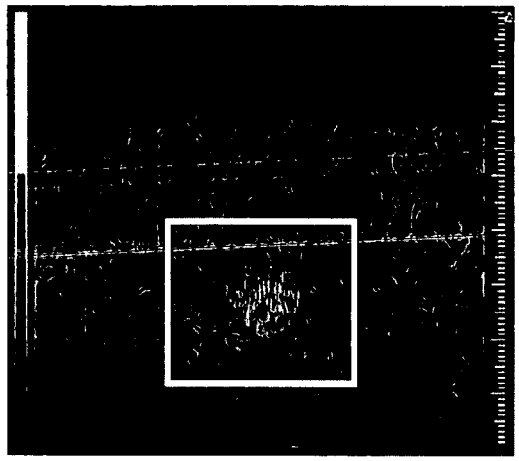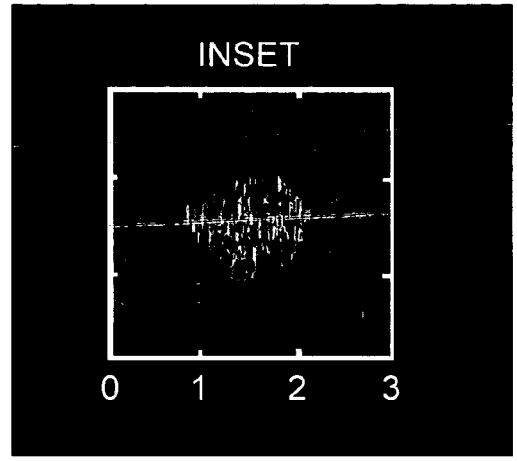
FIG.29A  FIG.29B
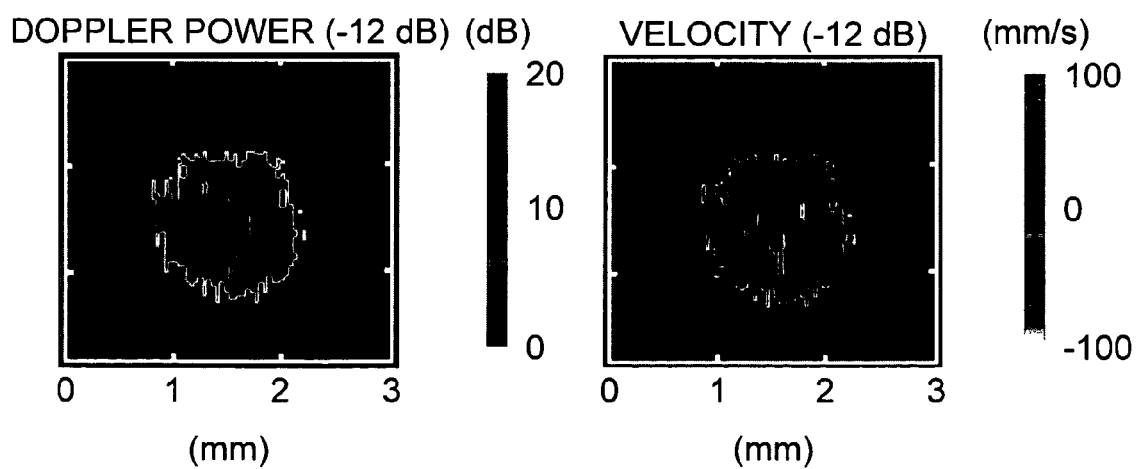
FIG.29C  FIG.29D

HIGH FREQUENCY ULTRASOUND IMAGING USING CONTRAST AGENTS

CROSS-REFERENCE TO RELATED APPLICATIONS

This application claims priority to U.S. Provisional Application No. 60/538,174, filed Jan. 20, 2004. The aforementioned application is herein incorporated by reference in its entirety.

BACKGROUND

Small animal or laboratory animal research is a cornerstone of modern biomedical advancement. Research using small animals enables researchers to understand complex biological mechanisms, to understand human and animal disease progression, and to develop new drugs to cure or alleviate many human and animal maladies. Small animal research is important in many areas of biomedical research including neurobiology, developmental biology, cardiovascular research and cancer biology. Cardiovascular disease and cancer are currently two of the most common causes of death and morbidity in our society. Therefore, it is extremely important for small animal research to be sufficiently sophisticated and efficient to allow for medical advance in these and other categories of disease.

For small animal research to continue to advance the understanding of diseases, it is of great benefit for researchers to image or visualize structures within a small animal. Structures within the small animal that could benefit from imaging include, but are not limited to, tissues, organs, and cavities. Moreover, it is valuable for these structures to be imaged longitudinally over an animal's lifetime. One method for visualizing structures within a small animal is invasive surgery. Invasive surgery involves surgically invading an animal to visualize its internal structures. Once the animal is incised and the desired structure visualized, the animal's incision can be closed and the animal can be allowed to recover, or the animal can be sacrificed. If a researcher wants to visualize the same structure at a subsequent time in the animal's lifetime, surgery can be repeated on the same animal, or, if the small animal was sacrificed, a different animal can be visualized at the desired period in its life. Invasive surgery, however, has many drawbacks.

The drawbacks of invasive surgery include, but are not limited to, poor results, potential surgical complications and high costs. Results obtained using surgery are often poor because surgery can stress the animal or cause post surgical complications, including infection. An animal's stress response to surgery may prevent a researcher from drawing accurate conclusions regarding that animal's response to a given disease, drug, or medical procedure. Post surgical infection can also negatively affect results. Moreover, an infection can kill the animal, or require the animal to be medically treated or sacrificed. If an animal dies from infection, another post surgical complication, or is sacrificed, another animal must be studied. When a different animal must be used, inaccuracies are inherently introduced into a researcher's findings. These inaccuracies may be due to individual differences between study animals, differing husbandry conditions, or any other number of potential differences. All of these drawbacks increase the cost of research by increasing the number of animals needed and by making poor results more likely.

Non-invasive ultrasound has long been used as a diagnostic tool to aid in therapeutic procedures. It is based on the principle that waves of sound energy can be focused upon an area of interest, reflected and processed to produce an image. To improve the images obtained using conventional, or low frequency ultrasound, echogenic contrast agents are sometimes used to create a reflector of ultrasonic energy in an area of interest. In conventional frequency ultrasound, a rapid development of microbubble contrast imaging techniques for medical ultrasound has occured. Non-linear scattering from resonant bubble population has been exploited to implement a variety of detection methods, which are used to suppress tissue signals and enhance the detection of blood. Non-linear microbubble imaging for commercial ultrasound operating at conventional frequencies has demonstrated important clinical utility in improving structure visualization including improving small vessel detection and in cardiac chamber imaging. Because conventional frequency ultrasound operates in the 1-8 MHz range, microbubble contrast agents have been designed to work well within this frequency range.

Ultrasound has recently been adapted for use in small animal research. In particular, high frequency ultrasound has been used to visualize anatomical structures and hemodynamic function in longitudinal studies of small animals. High frequency ultrasound imaging of small animals is non-invasive and allows longitudinal studies of individual animals. These studies reduce the number of animals required for analysis and alleviate many problems associated with invasive surgery. Potential areas of small animal research where high frequency ultrasound imaging is beneficial include, but are not limited to, cancer and angiogenesis studies, developmental biology, cardiovascular research and neurological research. In each of these areas, ultrasound imaging offers the distinct advantage of non-invasive longitudinal studies that were previously unavailable using invasive surgery or conventional frequency ultrasound.

To improve on these advantages it would be desirable to take advantage of non-linear scattering by microbubble contrast agents of high frequency ultrasound in small animals. Improved high frequency ultrasound imaging in small animals using microbubble contrast agents could improve the sophistication and efficiency of biomedical research and drug development in small animals. The need exists in the art for a method of producing an ultrasound image of a small animal and its internal structures that is enhanced by non-linear scattering of ultrasound by microbubble contrast agents. A need also exists for a composition of microbubbles designed to enhance imaging when high-frequency ultrasound is utilized.

SUMMARY

Provided herein are microbubble contrast agents designed for use with high frequency ultrasound and methods of using these contrast agents to enhance high frequency ultrasound imaging in small laboratory animals.

Further provided herein is a composition comprising a microbubble contrast agent, wherein at least 20% by volume of the microbubbles in the contrast agent have a size of less than 1 micrometer (μm) also referred to throughout as "micron", wherein the contrast agent produces non-linear scattering when contacted by ultrasound at a frequency above 20 MHz. Also provided herein are compositions wherein at least 30%, 40%, 50% or 75% by volume of the microbubbles in the contrast agent have a size of less than 1 micron. In another embodiment, the microbubbles in the contrast agent have at least 10% by volume of a size less than 500 nanometers, or in another embodiment, at least 5% by volume of the microbubbles in the contrast agent have a size of less than 200 nanometers. Optionally, the compositions comprise a targeted contrast agent.

Also provided herein are compositions wherein the microbubble contrast agent produces non-linear scattering when contacted by ultrasound at a frequency above 30 MHz, 40 MHz, 50 MHz or 60 MHz. Further, transducer operating frequencies significantly greater than those mentioned above are also contemplated. In another embodiment, the microbubbles can be disrupted or popped by the ultrasound at a frequency above 20 MHz. The microbubbles may also be disrupted by ultrasound at a frequency above 30 MHz, 40 MHz, 50 MHz or 60 MHz.

Also provided herein is a method for producing an ultrasound image comprising administering contrast agent to a laboratory animal, generating ultrasound at a frequency of at least 20 MHz, transmitting ultrasound energy at a frequency of at least 20 MHz into the subject, receiving non-linear ultrasound energy from the contrast agent in the subject and processing the received ultrasound to provide an image. Optionally, the contrast agent is a targeted contrast agent. In one embodiment of the method, the contrast agent is a microbubble contrast agent. The methods provided herein can be used to image any laboratory animal but is especially suited for a mouse or a rat. The methods can also be used to image organs of a laboratory animal. The organs imaged can include, but are not limited to, a lung, a heart, a brain, a kidney a liver and blood. In one embodiment the organ imaged is the organ of a mouse or a rat. The methods can also be used to image a neoplastic condition in a laboratory animal. In one embodiment the neoplastic condition is in a mouse or a rat.

Such methods can also provide an image in real-time and can provide an image having a spatial resolution of less than 100 microns. The methods can also be used to produce an image having a frame rate of at least 15 frames per second (fps). In another embodiment, a contrast agent can be targeted to a particular cell type, tissue type or organ.

The disclosed methods include embodiments where in the contrast agent is disrupted by a pulse of ultrasound energy.

Also provided are methods wherein at least 20% by volume of the microbubbles in the contrast agent have a size of less than 1 micron. In other embodiments at least 30%, 40%, 50% or 75% by volume of the microbubbles in the contrast agent have a size of less than 1 micron. Also provided herein is a method wherein the ultrasound is generated and transmitted at least at 30 MHz, 40 MHz, 50 MHz or 60 MHz. Further, transducer operating frequencies significantly greater than those mentioned above are also contemplated.

BRIEF DESCRIPTION OF THE DRAWINGS

The accompanying drawings, which are incorporated in and constitute a part of this specification, illustrate several aspects described below.

FIGS. 8A through 8E show schematic diagrams illustrating an exemplary system for generating an ultrasound image using line based image reconstruction that can be used with the disclosed compositions and methods.

FIGS. 29a, b, c and d show color flow imaging using a 1 mm diameter wall-less vessel phantom. (a) fundamental 20 MHz B-scan image of the vessel (large hache marks separated by 1 mm); (b) inset. SH20 Doppler power (c) and velocity (d) images of the vessel illustrate the ability to form color flow images using nonlinear scattering at high frequencies.

DETAILED DESCRIPTION

Figure 1A:
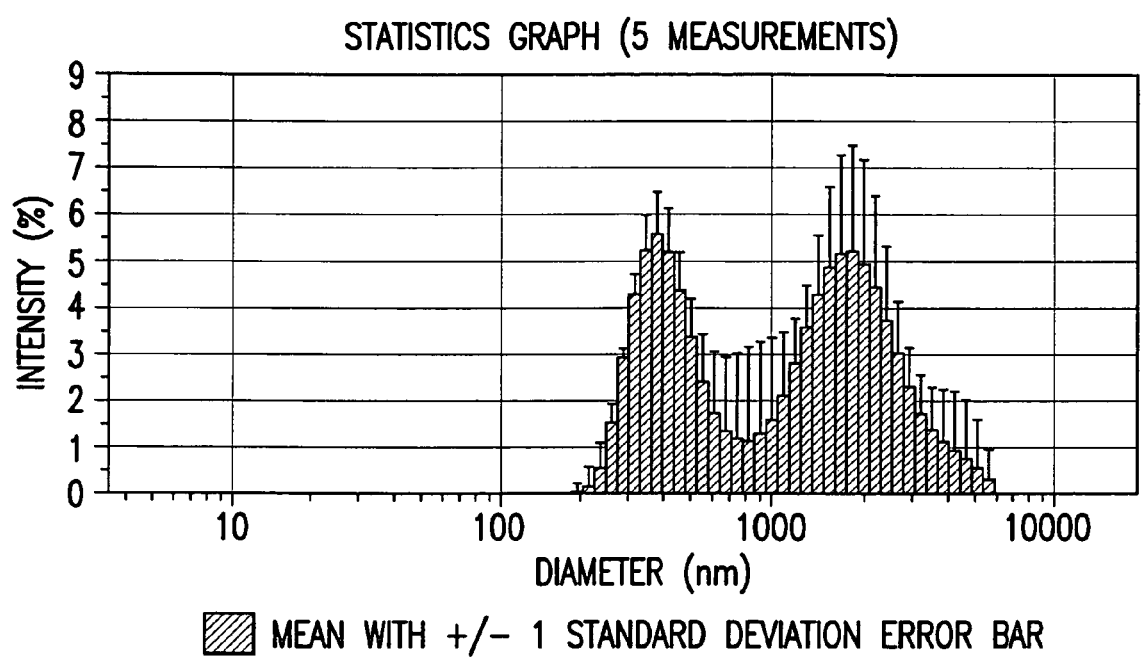
FIG. 1 shows a size statistics report of microbubble contrast agent by intensity.

As used in the specification and the appended claims, the singular forms "a," "an" and "the" include plural referents unless the context clearly dictates otherwise. Thus, for example, reference to "a contrast agent" can include mixtures of two or more such agents unless the context indicates otherwise.

Although the methods and compositions have been described with reference to specific details of certain embodiments thereof, it is not intended that such details should be regarded as limitations upon the scope of the invention except as and to the extent that they are included in the accompanying claims.

It is understood that there are a number of values disclosed herein, and that each value is also herein disclosed as "about" that particular value in addition to the value itself. For example, if the value "20" is disclosed, then "about 20" is also disclosed. It is also understood that when a value is disclosed that "less than or equal to" the value, "greater than or equal to the value" and possible ranges between values are also disclosed, as appropriately understood by the skilled artisan. For example, if the value "20" is disclosed the "less than or equal to 20" as well as "greater than or equal to 20" is also disclosed. It is also understood that the throughout the application, values are provided in a number of different formats, and that these values represent endpoints and starting points, and ranges for any combination of the values. For example, if a particular value "20" and a particular value "30" are disclosed, it is understood that greater than, greater than or equal to, less than, less than or equal to, and equal to 20 and 30 are considered disclosed as well as between 20 and 30.

Provided herein is a composition comprising a microbubble contrast agent, wherein at least 20% by volume of the microbubbles in the contrast agent have a size of less than 1 micrometer (μm) also referred to throughout as "micron", wherein the contrast agent produces non-linear scattering when contacted by ultrasound at a frequency above 20 MHz. The ultrasound can be transmitted and generated using a pulsed-wave doppler system as described in example 2. Moreover, color flow doppler, pulsed-wave doppler, continuous wave doppler, and power flow doppler processing of received ultrasound can be used. Also provided herein are compositions wherein at least 30%, 40%, 50% or 75% by volume of the microbubbles in the contrast agent have a size of less than 1 micron. In another embodiment, the microbubbles in the contrast agent have at least 10% by volume of a size less than 500 nanometers, or in another embodiment, at least 5% by volume of the microbubbles in the contrast agent have a size of less than 200 nanometers. Examples of commercial microbubble contrast agents include, but are not limited to, Definity™, Sonovue™, Levovist™ and Optison™. Examples of microbubble contrast agents are described in U.S. Pat. Nos. 5,529,766, 5,558,094, 5,573,751, 5,527,521, 5,547,656, 5,769,080, 6,652,782, 5,425,366, 5,141,738, 4,681,119, 4,466,442, 4,276,885, 6,200,548, 5,911,972, 5,711,933, 5,686,060, 5,310,540, 5,271,928.

A typical contrast agent comprises a thin flexible or rigid shell composed of albumin, lipid or polymer confining a gas such as nitrogen or a perflurocarbon. Other examples of representative gases include air, oxygen, carbon dioxide, hydrogen, nitrous oxide, inert gases, sulpher fluorides, hydrocarbons, and halogenated hydrocarbons. Liposomes or other microbubbles can also be designed to encapsulate gas or a substance capable of forming gas as described in U.S. Pat. No. 5,316,771. In another embodiment, gas or a composition capable of producing gas can be trapped in a virus, bacteria, or cell to form a microbubble contrast agent.

Figure 2A:
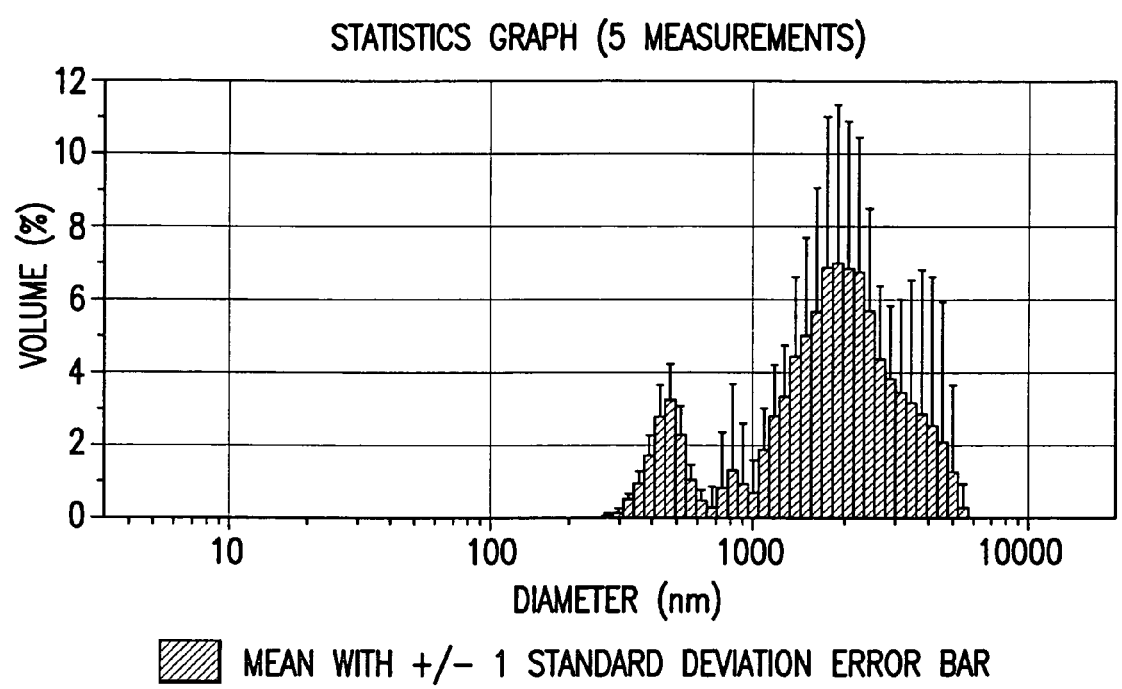
FIG. 2 shows a size statistics report of microbubble contrast agent by volume.
Figure 3A:
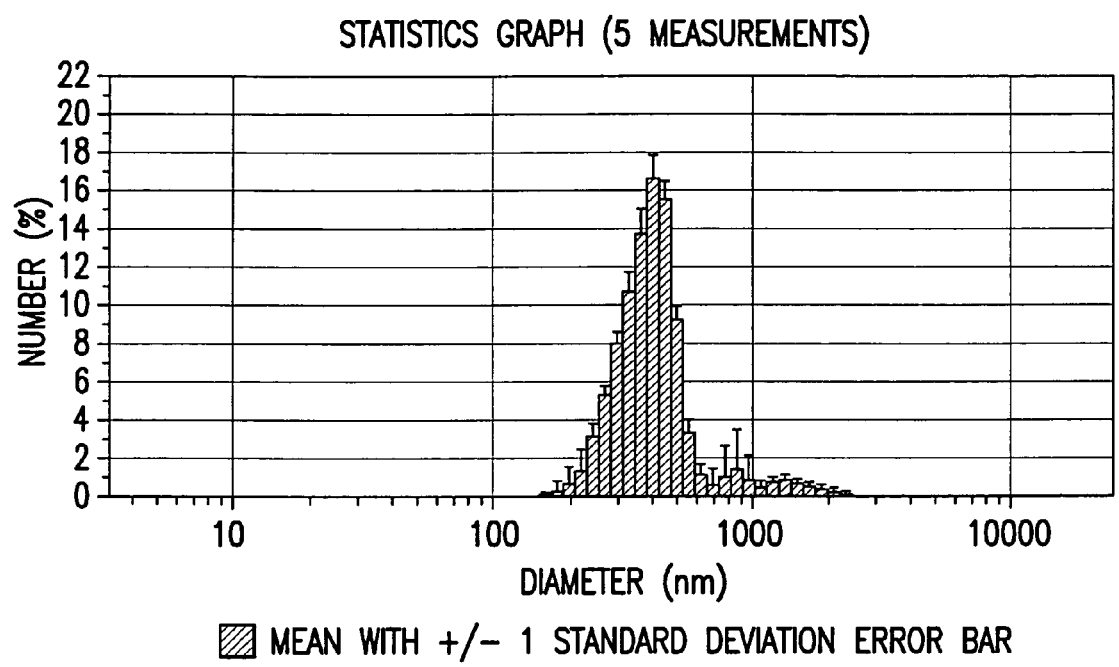
FIG. 3 shows a size statistics report of microbubble contrast agent by number.

A contrast agent can be modified to achieve a desired volume percentage by a filtering process, such as by micro or nano-filtration using a porous membrane. Contrast agents can also be modified by allowing larger bubbles to separate in solution relative to smaller bubbles. For example, contrast agents can be modified by allowing larger bubbles to float higher in solution relative to smaller bubbles. A population of microbubbles of an appropriate size to achieve a desired volume percentage can subsequently be selected. Other means are available in the art for separating micron-sized and nano-sized particles and can be adapted to select a microbubble population of the desired volume of submicron bubbles such as by centrifugation. The number of mico and nanobubbles of differing sizes (FIG. 1) can be determined, for example, using an optical decorrelation method. The diameter of mico and nanobubbles making up given volume percentage (FIG. 2) can also be determined and the number percentage of micro and nanobubbles at different sizes (FIG. 3) can also be determined. For optical decorrelation methods a Malvin™ Zetasizer™ or similar apparatus may be used.

Also provided herein are compositions wherein the microbubble contrast agent produces non-linear scattering when contacted by ultrasound at a frequency above 30 MHz, 40 MHz, 50 MHz or 60 MHz. Non-linear scattering can be measured, for example, as set forth herein. Further, transducer operating frequencies significantly greater than those mentioned above are also contemplated. In another embodiment, the above contrast agent compositions can be disrupted or popped by the ultrasound energy at a frequency above 20 MHz. As used throughout, "disrupted" or "destroyed" means that a microbubble is fragmented, ruptured, or cracked such that gas escapes from the microbubble. The compositions may also be disrupted by ultrasound at a frequency above 30 MHz, 40 MHz, 50 MHz or 60 MHz. The destruction or popping creates a means of probing perfusion of selected tissues or a means for releasing a therapeutic payload.

Also provided herein is a method for producing an ultrasound image comprising administering contrast agent to a laboratory animal, generating ultrasound at a frequency of at least 20 MHz, transmitting ultrasound at a frequency of at least 20 MHz into the subject, receiving non-linear ultrasound from the contrast agent in the subject and processing the received ultrasound to provide an image. In one embodiment of the method, the contrast agent is a microbubble contrast agent. Once transmitted the ultrasound interacts with the laboratory animal's tissue and the contrast agent. The ultrasound is reflected by structures within the animal and scattered non-linearly by the contrast agent. Echos resulting from interactions with the animal and contrast agent return to an ultrasound imaging system. After ultrasound energy is received it is processed to form an image.

Administration of contrast imaging agents of the present invention may be carried out in various fashions, such as intravascularly, intralymphatically, parenterally, subcutaneously, intramuscularly, intraperitoneally, interstitially, hyperbarically, orally, or intratumorly using a variety of dosage forms. One preferred route of administration is intravascularly. For intravascular use the contrast agent is generally injected intravenously, but may be injected intraarterially as well. The useful dosage to be administered and the mode of administration may vary depending upon the age and weight of the subject, and on the particular diagnostic application intended. Typically, dosage is initiated at lower levels and increased until the desired contrast enhancement is achieved. Generally, the contrast agent construed in accordance with embodiments of the invention is administered in the form of an aqueous suspension such as in water or a saline solution (e.g., phosphate buffered saline). The water can be sterile and the saline solution can be a hypertonic saline solution (e.g., about 0.3 to about 0.5% NaCl), although, if desired, the saline solution may be isotonic. The solution also may be buffered, if desired, to provide a pH range of pH 6.8 to pH 7.4. In addition, dextrose may be included in the media.

The contrast agent provided herein, while not limited to a particular use, can be administered intravenously to a laboratory animal. A laboratory animal includes, but is not limited to, a rodent such as a mouse or a rat. As used herein, the term laboratory animal is also used interchangeably with small animal, small laboratory animal, or subject, which includes mice, rats, cats, dogs, fish, rabbits, guinea pigs, rodents, etc. The term laboratory animal does not denote a particular age or sex. Thus, adult and newborn animals, as well as fetuses (including embryos), whether male or female, are included.

In one embodiment, the contrast agent is administered intravenously to a mouse or a rat. In another embodiment, the contrast agent is administered into the tail vein of a mouse or a rat. The intravenous injection can be administered as a single bolus dose, or by repeated injection or continuous infusion. Effective dosages and schedules for administering the compositions may be determined empirically, and making such determinations is within the ordinary skill in the art. The dosage range for the administration of the compositions are those large enough to produce the desired ultrasound imaging effect. Such an effect typically includes an increased return from the contrast agent versus a reduced return from surrounding tissue. The dosage should not be so large as to cause adverse side effects. Generally, the dosage will vary with the ultrasound imaging protocol and the desired imaging characteristics, and can be determined by one skilled in the art. The dosage can be adjusted by the individual researcher. Dosage can vary, and can be administered in one or more dose administrations daily, for one or several days. The ultrasound can be transmitted immediately after administration of contrast agent or at any time interval subsequent to contrast agent administration. Ultrasound imaging can also begin prior to administration, continue throughout the administration process, and continue subsequent to the completion of administration. The imaging can also take place at any discrete time prior to, during or after administration of the contrast agent.

The methods described herein can be used to image a mouse or a rat. The methods above can also be used to image organs of a laboratory animal. The organs imaged can include, but are not limited to a lung, a heart, a brain, a kidney a liver and blood. In one embodiment, the organ imaged is the organ of a mouse or a rat. The compositions and methods can also be used to image physiological or pathological processes such as angiogenesis.

The methods described can also be used to image a neoplastic condition in a laboratory animal. For example, the methods can be used to image angiogenesis in a subject associated with tumor growth. A representative but non-limiting list of cancers that the disclosed method can be used to image is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers, testicular cancer, colon and rectal cancers, prostatic cancer, or pancreatic cancer. In one embodiment, the neoplastic condition imaged is found in a mouse or a rat.

The methods described can be used to provide an image in real-time and can provide an image having a spatial resolution of less than 100 microns. The methods can also be used to produce an image having a frame rate of at least 15 frames per second (fps).

Provided herein is a method of producing an ultrasound image comprising administering a targeted contrast agent to a subject, generating ultrasound at a frequency of at least 20 MHz, transmitting ultrasound at a frequency of at least 20 MHz into the subject, receiving non-linear ultrasound scattered from the contrast agent in the subject and processing the received ultrasound to provide an image. The ultrasound can be generated and transmitted using a pulsed-wave doppler system as described in example 2. Optionally, the ultrasound can be generated and transmitted at least 30, 40, 50 or 60 MHz. Optionally, the ultrasound can be transmitted percutaneously or extravascularly.

Several strategies can be used to direct ultrasound contrast agent to a desired target. One strategy takes advantage of the inherent chemical properties of the microbubble shell components. For example, albumin or lipid microbubbles can attach to the surface of target cells via cell receptors. Another strategy involves conjugation of specific ligands or antibodies that bind to desired markers.

A targeted contrast agent is an ultrasound contrast agent that can bind selectively or specifically to a desired target. Such selective or specific binding can be readily determined using the methods and devices described herein. For example, selective or specific binding can be determined in vivo or in vitro by administering a targeted contrast agent and detecting an increase in non-linear ultrasound scattering from the contrast agent bound to a desired target. Thus a targeted contrast agent can be compared to a control contrast agent having all the components of the targeted contrast agent except the targeting ligand. By detecting increased non-linear resonance or scattering from the targeted contrast agent versus a control contrast agent, the specificity or selectivity of binding can be determined. If an antibody or similar targeting mechanism is used, selective or specific binding to a target can be determined based on standard antigen/epitope/antibody complementary binding relationships. Further, other controls can be used. For example, the specific or selective targeting of the microbubbles can be determined by exposing targeted microbubbles to a control tissue, which includes all the components of the test tissue except for the desired target ligand or epitope. To compare a control sample to a test sample, levels of non-linear resonance can be detected by enhanced ultrasound imaging.

Specific or selective targeted contrast agents can be produced by methods known in the art, for example, using the methods described. For example, targeted contrast agents can be prepared as perfluorocarbon or other gas-filled microbubbles with a monoclonal antibody on the shell as a ligand for binding to target ligand in a subject as described in Villanueva et al., "Microbubbles Targeted to Intracellular Adhesion Molecule-1 Bind to Activated Coronary Artery Endothelial Cells," Circulation (1998) 98: 1-5. For example, perfluorobutane can be dispersed by sonication in an aqueous medium containing phosphatidylcholine, a surfactant, and a phospholipid derivative containing a carboxyl group. The perfluorobutane is encapsulated during sonication by a lipid shell. The carboxylic groups are exposed to an aqueous environment and used for covalent attachment of antibodies to the microbubbles by the following steps. First, unbound lipid dispersed in the aqueous phase is separated from the gas-filled microbubbles by floatation. Second, carboxylic groups on the microbubble shell are activated with 1-ethyl-3-(3-dimethylaminopropyl) carbodimide, and antibody is then covalently attached via its primary amino groups with the formation of amide bonds.

Targeted microbubbles can also be prepared with a biotinylated shell as described in Weller et al., "Modulating Targeted Adhesion of an Ultrasound Contrast Agent to Dysfunctional Endothelium," Ann. Biomed. Engineering, (2002) 30: 1012-1019. For example, lipid-based perfluorocarbon-filled microbubbles can be prepared with monoclonal antibody on the shell using avidin-biotin bridging chemistry using the following protocol. Perfluorobutane is dispersed by sonication in aqueous saline containing phosphatidyl choline, polyethylene glycol (PEG) stearate, and a biotinylated derivative of phosphatidylethanolamine as described in the art. The sonication results in the formation of perfluorobutane microbubbles coated with a lipid monolayer shell and carrying the biotin label. Antibody conjugation to the shell is achieved via avidin-biotin bridging chemistry. Samples of biotinylated microbubbles are washed in phosphate-buffered saline (PBS) by centrifugation to remove the lipid not incorporated in the microbubble shell. Next, the microbubbles are incubated in a solution (0.1-10 µg/mL) of streptavidin of in PBS. Excess streptavidin is removed by washing with PBS. The microbubbles are then incubated in a solution of biotinylated monoclonal antibody in PBS and washed again. The resultant microbubble have antibody conjugated to the lipid shell via biotin-streptavidin-biotin linkage. In another example, for targeted microbubbles, biotinylated microbubbles can be prepared by sonication of an aqueous dispersion of decafluorobutane gas, distearoylphodphatidylcholine, polyethyleneglycol-(PEG-) state, and distearoyl-phosphatidylethanolamine-PEG-biotin. Microbubbles can then be combined with streptavidin, washed, and combined with biotinylated echistatin.

Targeted microbubbles can also be prepared with an avidinated shell, as is known in the art. In a preferred embodiment, a polymer microbubble can be prepared with an avidinated or streptavidinated shell. For example, a polymer contrast agent comprising a functionalized polyalkylcyanoacrylate can be used as described in patent application PCT/EP01/02802. Streptavidin can be bonded to the contrast agent via the functional groups of the functionalized polyalkylcyanoacrylate. In a preferred embodiment, avidinated microbubbles can be used in the methods disclosed herein. When using avidinated microbubbles, a biotinylated antibody or fragment thereof or another biotinylated targeting molecule or fragments thereof can be administered to a subject. For example, a biotinylated targeting ligand such as an antibody, protein or other bioconjugate can be used. Thus, a biotinylated antibody, targeting ligand or molecule, or fragment thereof can bind to a desired target within a subject. Once bound to the desired target, the contrast agent with an avidinated shell can bind to the biotinylated antibody, targeting molecule, or fragment thereof. When bound in this way, high frequency ultrasound energy can be transmitted to the bound contrast agent, which can produce non-linear scattering of the transmitted ultrasound energy. An avidinated contrast agent can also be bound to a biotinylated antibody, targeting ligand or molecule, or fragment thereof prior to administration to the subject.

When using a targeted contrast agent with a biotinylated shell or an avidinated shell a targeting ligand or molecule can be administered to the subject. For example, a biotinylated targeting ligand such as an antibody, protein or other bioconjugate, can be administered to a subject and allowed to accumulate at a target site. A fragment of the targeting ligand or molecule can also be used.

When a targeted contrast agent with a biotinylated shell is used, an avidin linker molecule, which attaches to the biotinylated targeting ligand can be administered to the subject. Then, a targeted contrast agent with a biotinylated shell is administered to the subject. The targeted contrast agent binds to the avidin linker molecule, which is bound to the biotinylated targeting ligand, which is itself bound to the desired target. In this way a three step method can be used to target contrast agents to a desired target. The intermediate targeting ligand can bind to all of the desired targets detailed above as would be clear to one skilled in the art.

Targeted contrast agents or non-targeted contrast agents can also comprise a variety of markers, detectable moieties, or labels. Thus, a microbubble contrast agent equipped with a targeting ligand or antibody incorporated into the shell of the microbubble can also include another detectable moiety or label. As used herein, the term "detectable moiety" is intended to mean any suitable label, including, but not limited to, enzymes, fluorophores, biotin, chromophores, radioisotopes, colored particles, electrochemical, chemical-modifying or chemiluminescent moieties. Common fluorescent moieties include: fluorescein, cyanine dyes, coumarins, phycoerythrin, phycobiliproteins, dansyl chloride, Texas Red, and lanthanide complexes. Of course, the derivatives of these compounds which are known to those skilled in the art also are included as common fluorescent moieties.

The detection of the detectable moiety can be direct provided that the detectable moiety is itself detectable, such as, for example, in the case of fluorophores. Alternatively, the detection of the detectable moiety can be indirect. In the latter case, a second moiety reactable with the detectable moiety, itself being directly detectable can be employed. The detectable moiety may be inherent to the molecular probe. For example, the constant region of an antibody can serve as an indirect detectable moiety to which a second antibody having a direct detectable moiety can specifically bind.

As with non-targeted contrast agents, targeted contrast agents can be modified to achieve a desired volume percentage for high frequency imaging by a filtering process, such as by micro or nano-filtration using porous membranes. Targeted contrast agents can also be modified by allowing larger bubbles to separate in solution relative to smaller bubbles. For example, targeted contrast agents can be modified by allowing larger bubbles to float higher in solution relative to smaller bubbles. A population of microbubbles of an appropriate size to achieve a desired volume percentage can subsequently be selected. Other means are available in the art for separating micron-sized and nano-sized particles and could be adapted to select a microbubble population of the desired volume of submicron bubbles such as by centrifugation. Sizing of the microbubbles can occur before or after the microbubbles are adapted to be targeted. For example, a desired size microbubble population can be selected prior to implementing the protocols detailed above for producing a targeted microbubble contrast agent.

For example, provided herein are methods wherein at least 20% by volume of the microbubbles in the targeted contrast agent have a size of less than 1 micron. In other embodiments at least 30%, 40%, 50% or 75% by volume of the microbubbles in the contrast agent have a size of less than 1 micron. Also provided herein is a method of using targeted contrast agents wherein the ultrasound is generated and transmitted at least at 30 MHz, 40 MHz, 50 MHz or 60 MHz. Further, transducer operating frequencies significantly greater than those mentioned above are also contemplated. Thus, for both targeted and non-targeted ultrasound contrast agents, a desired percentage by volume of microbubbles can be selected to enhance ultrasound imaging by non-linear scattering of the contrast agent and thus to enhance ultrasound imaging. Such a population can be selected as described above, by being compared to a control population have all of the components of the test sample of microbubbles except for a difference in microbubble size.

The targeted contrast agents used in the methods described can be targeted to a variety of cells, cell types, antigens, cellular membrane proteins, organs, markers, tumor markers, angiogenesis markers, blood vessels, thrombus, fibrin, and infective agents. For example, targeted microbubbles can be produced that localize to targets expressed in a subject. Desired targets are generally based on, but not limited to, the molecular signature of various pathologies, organs and/or cells. For example, adhesion molecules such as integrin $\alpha_v\beta_3$, intercellular adhesion molecule-1 (I-CAM-1), fibrinogen receptor GPIIb/IIIa and VEGF receptors are expressed in regions of angiogenesis, inflammation or thrombus. These molecular signatures can be used to localize high frequency ultrasound contrast agents through the use of targeting molecules, including but not limited to, complementary receptor ligands, targeting ligands, proteins, and fragments thereof. Target cell types include, but are not limited to, endothelial cells, neoplastic cells and blood cells. The methods described herein optionally use microbubbles targeted to VEGFR2, I-CAM-1, $\alpha_v\beta_3$ integrin, $\alpha_v$ integrin, fibrinogen receptor GPIIb/IIIa, P-selectin, mucosal vascular adressin cell adhesion molecule-1. Moreover, using methods known in the art, complementary receptor ligands, such as monoclonal antibodies, can be readily produced to target other markers in a subject. For example, antibodies can be produced to bind to tumor marker proteins, organ or cell type specific markers, or infective agent markers. Thus, the targeted contrast agents can be targeted, using antibodies, proteins, fragments thereof, or other ligands, as described herein, to sites of neoplasia, angiogenesis, thrombus, inflammation, infection, as well as to diseased or normal organs or tissues including but not limited to blood, heart, brain, blood vessel, kidney, muscle, lung and liver. Optionally, the targeted markers are proteins and may be extracellular or transmembrane proteins. The targeted markers, including tumor markers, can be the extracellular domain of a protein. The antibodies or fragments thereof designed to target these marker proteins can bind to any portion of the protein. Optionally, the antibodies can bind to the extracellular portion of a protein, for example, a cellular transmembrane protein. Antibodies, proteins, or fragments thereof can be made that specifically or selectively target a desired target molecule using methods known in the art.

There are a number of methods for isolating proteins which can bind a desired target. For example, phage display libraries have been used to isolate numerous peptides that interact with a specific target. (See for example, U.S. Pat. Nos. 6,031,071; 5,824,520; 5,596,079; and 5,565,332 which are herein incorporated by reference at least for their material related to phage display and methods related to combinatorial chemistry). Thus targeted contrast agents can comprise proteins or fragments thereof that interact with a desired target. A targeted contrast agent can also comprise a binding domain of an antibody or phage. Disclosed are methods of producing an ultrasound image using targeted contrast agent that is biotinylated, wherein the biotin is bound by avidin and wherein the avidin is linked to the binding domain of an antibody or phage. Optionally, the binding domain of the antibody or phage can bind to a target in a subject. Further disclosed are methods of producing an ultrasound image using targeted contrast agent that is biotinylated, wherein the biotin is bound by avidin and wherein the biotin is linked to the binding domain of an antibody or phage. Optionally, the binding domain of the antibody or phage binds a target in a subject. Further disclosed are methods of producing an ultrasound image using a targeted contrast agent comprising a ligand. Optionally, the ligand is a protein or fragment thereof.

Monoclonal antibodies may be prepared using hybridoma methods, such as those described by Kohler and Milstein, Nature, 256:495 (1975) or Harlow and Lane. Antibodies, A Laboratory Manual. Cold Spring Harbor Publications, New York, (1988). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro. Preferably, the immunizing agent comprises the desired target or fragment thereof to be targeted using the disclosed ultrasound contrast agents. Traditionally, the generation of monoclonal antibodies has depended on the availability of purified protein or peptides for use as the immunogen. More recently, DNA based immunizations have shown promise as a way to elicit strong immune responses and generate monoclonal antibodies.

Generally, either peripheral blood lymphocytes ("PBLs") are used in methods of producing monoclonal antibodies if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, "Monoclonal Antibodies: Principles and Practice" Academic Press, (1986) pp. 59-103). Immortalized cell lines are usually transformed mammalian cells, including myeloma cells of rodent, bovine, equine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells. Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies (Kozbor, J. Immunol., 133:3001 (1984); Brodeur et al., "Monoclonal Antibody Production Techniques and Applications" Marcel Dekker, Inc., New York, (1987) pp. 51-63).

The culture medium in which the hybridoma cells are cultured can then be assayed for the presence of monoclonal antibodies directed against the desired target or fragment thereof to be targeted using the disclosed ultrasound contrast agents. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art, and are described further in the Examples below or in Harlow and Lane "Antibodies, A Laboratory Manual" Cold Spring Harbor Publications, New York, (1988).

After the desired hybridoma cells are identified, the clones may be subcloned by limiting dilution or FACS sorting procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, protein G, hydroxylapatite chromatography, gel electrophoresis, dialysis, or affinity chromatography.

The monoclonal antibodies may also be made by recombinant DNA methods, such as those described in U.S. Pat. No.4,816,567. DNA encoding the monoclonal antibodies can be readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as simian COS cells, Chinese hamster ovary (CHO) cells, plasmacytoma cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No.4,816,567) or by covalently joining to the immunoglobulin coding sequence all or part of the coding sequence for a non-immunoglobulin polypeptide. Optionally, such a non-immunoglobulin polypeptide is substituted for the constant domains of an antibody or substituted for the variable domains of one antigen-combining site of an antibody to create a chimeric bivalent antibody comprising one antigen-combining site having specificity for the desired target or fragment thereof to be targeted using the disclosed ultrasound contrast agents and another antigen-combining site having specificity for a different antigen.

As described herein for non-targeted contrast agents, the method using targeted contrast agents can be performed on a subject that is a laboratory animal. Optionally, the laboratory animal is selected from the group consisting of a mouse, rat and rabbit. When using the targeted contrast agent in the methods described herein, the targeted contrast agent can be administered as described above for non-targeted contrast agents, with similar carriers and imaging protocols.

As described herein, the contrast agents can be targeted to a particular cell type, antigen, tissue type or organ. To target contrast agents the agent can be conjugated to tissue, cell or organ-specific ligands such as antibodies, antibody fragments, peptides, lectins etc. Microbubble targeting can also be achieved by the intrinsic binding properties of the microbubble surface. Targeted microbubbles can contain drugs, genes or other desired compounds either inside the microbubble, integrated into the microbubble shell, attached to any portion of the microbubble shell or attached to any linker or ligand attached to the microbubble shell. A second level of targeting specificity can be achieved by carefully controlling the ultrasound field and limiting microbubble destruction to the region of interest. When microbubbles are disrupted or destroyed, drugs or genes that are housed within them or bound to their shells can be released to the blood stream are then delivered to tissue by convective forces through the permeabilized microvessels.

The above methods include embodiments wherein the contrast agent is disrupted or destroyed by a pulse of ultrasound. The pulse of ultrasound can be produced by the same or a different transducer as the transducer producing the imaging frequency ultrasound. Therefore, the above methods contemplate using a plurality of ultrasound probes and frequencies.

The desired ultrasound for use with the disclosed compositions and methods can be applied, transmitted and received using an ultrasonic scanning device that can supply an ultrasonic signal of at least 20 MHz to the highest practical frequency. One such device is the VisualSonics™ UBM system model VS40 VEVO 660 as described in Example 1. Another such system may have the following components as described in U.S. patent application Ser. No.: 10/683,890, U.S. patent application publication 20040122319, which is set forth in part below, and incorporated herein by reference. Other devices capable of transmitting and receiving ultrasound at the desired frequencies can also be used.

Figure 4:
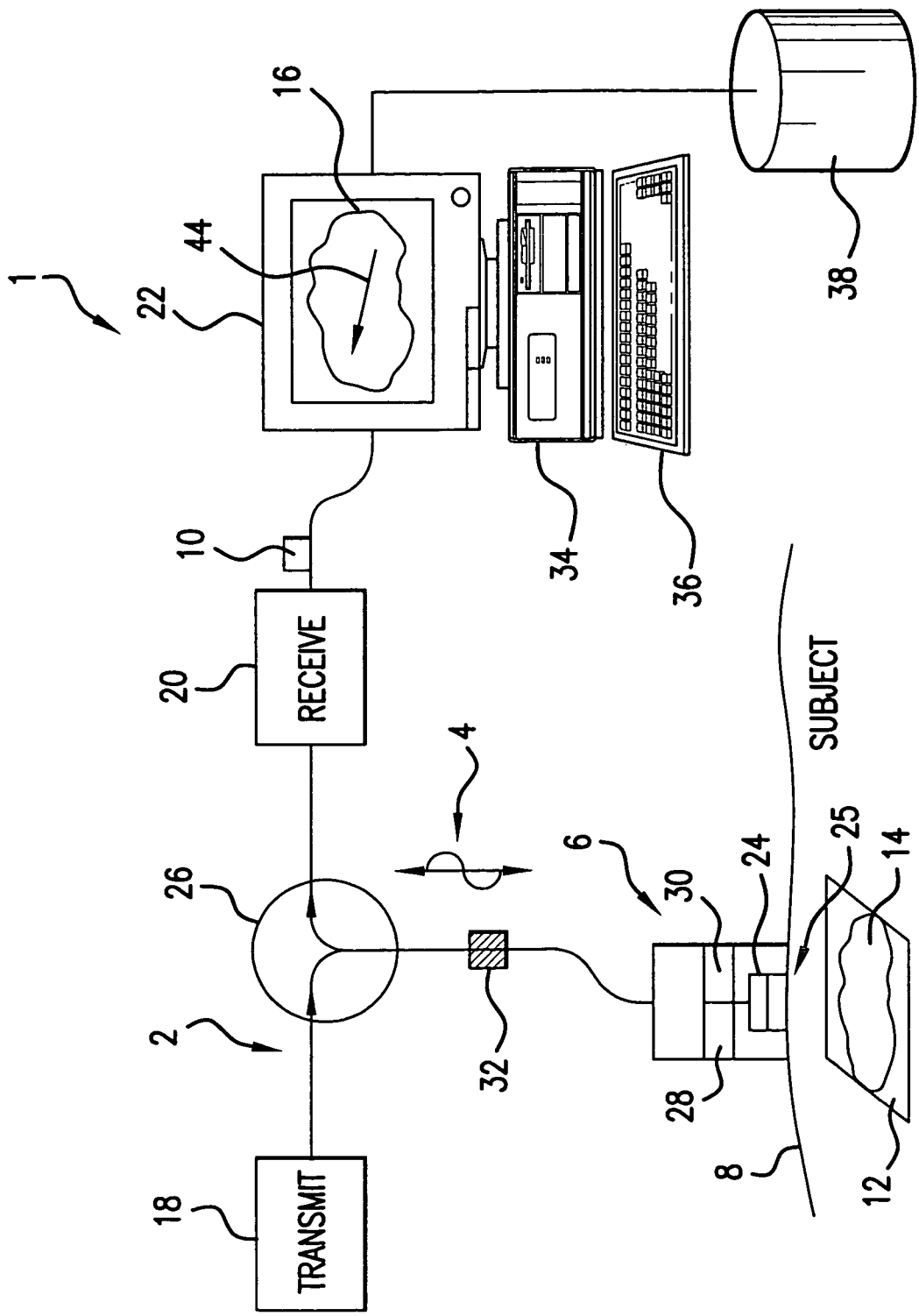
FIG. 4 shows a diagram of one embodiment of an exemplary ultrasound imaging system that can be used with the disclosed compositions and methods.

FIG. 4 is a diagram illustrating an ultrasound scanning system 1. The ultrasound scanning system 1 has an electronics circuit 2 for transmitting and receiving a series of ultrasound pulses 4 to and from a probe or scanhead 6. The scanhead 6 can be situated on a laboratory animal 8 to record image data 10 of a scan plane 12, representing a cross section of a target 14 for display on a display 16. The target 14 may be, for example, the organ of a small animal, such as a mouse, a rat or another research laboratory animal. Examples of organs that can be imaged include, but are not limited to, a lung, a heart, a brain, a kidney, a liver and blood flowing within the laboratory animal. Further, the ultrasound imaging system can be used to image a neo-plastic condition. The circuit 2 has a transmit subsystem 18 for generating the pulses 4 and a receive subsystem 20 for receiving the corresponding echo pulses 4, which are directed to a computer 22 for processing and eventual display as the image scan data 10. The scanhead 6 is coupled at 26 to the circuit 2. The scanhead 6 has a transducer assembly 24, with a membrane 25, which is coupled to a position encoder 28 in conjunction with a torque motor 30. The encoder 28 and motor 30 monitor the position of the transducer assembly 24 within the scanhead 6. The corresponding position data 32 is transmitted with the pulses 4, representing the image data 10, to the computer 22. The scanhead 6 can be used as an encapsulated real-time probe for recording and displaying image data 10 obtained in real-time at high frequencies, such as but not limited to greater than 20 MHz and including 25 MHz, 30 MHz, 35 MHz, 40 MHz, 45 MHz, 50 MHz, 55 MHz, 60 MHz and higher. Further, transducer operating frequencies significantly greater than those mentioned above are also contemplated.

The system 1 also includes a system processor 34. The processor 34 is coupled to the display or monitor 16 and to a human-machine interface 36, such as a keyboard, mouse, or other suitable device. If the monitor 16 is touch sensitive, then the monitor 16 can be employed as the input element for the human-machine interface 36. A computer readable storage medium 38 is coupled to the processor 34 for providing instructions to the processor 34 to instruct and/or configure the operation of the monitor 16 for recording and displaying the data 10, 32 on the monitor 16. The computer readable medium 38 can include hardware and/or software such as, by way of example only, magnetic disks, magnetic tape, optically readable medium such as a CD ROM, and semiconductor memory such as a PCMCIA card. In each case, the medium 38 may take the form of a portable item such as a small disk, floppy diskette, cassette, or it may take the form of a relatively large or immobile item such as hard disk drive, solid state memory card, or RAM coupled to the processor 34. It should be noted that the above listed example mediums 38 can be used either alone or in combination.

Figure 5:
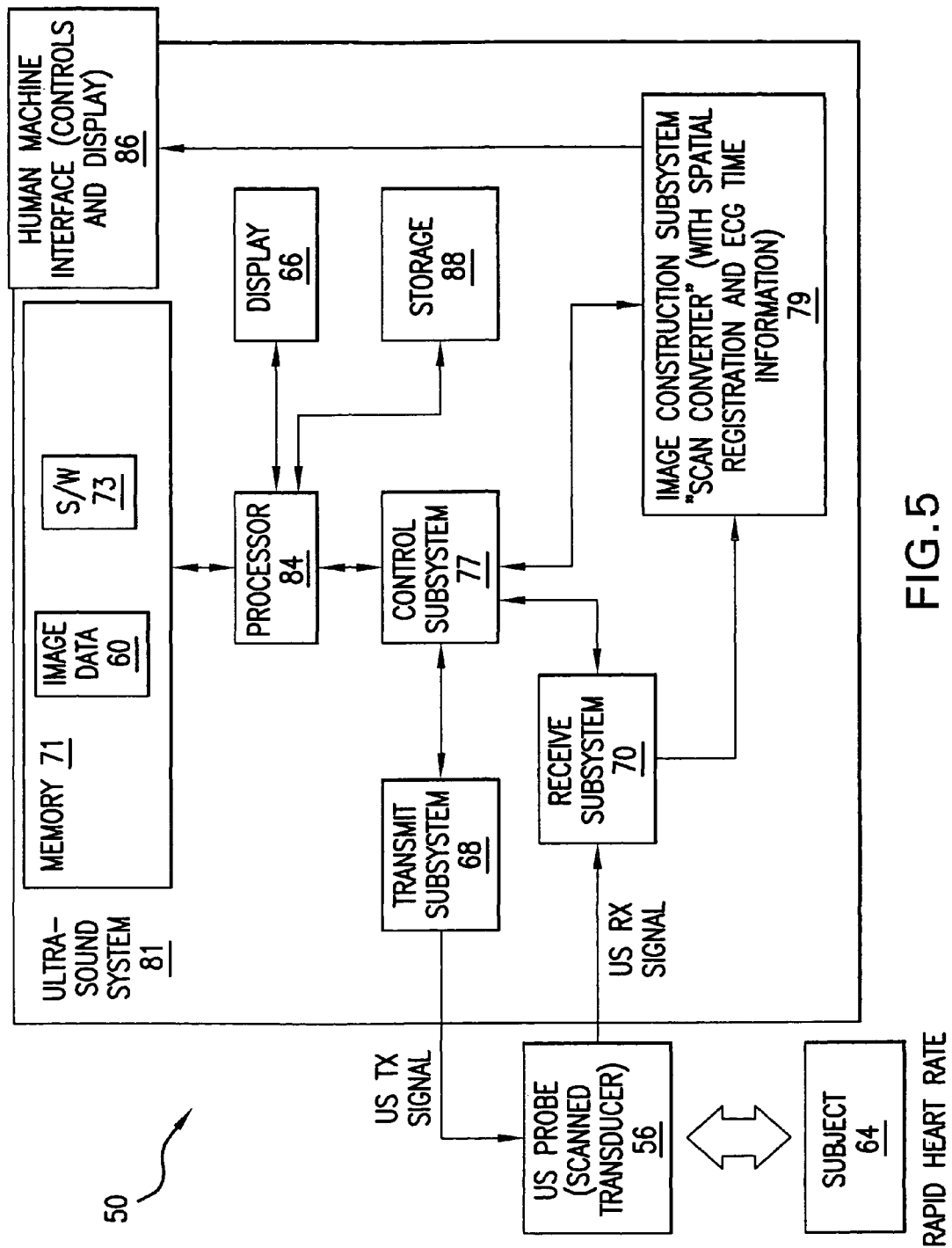
FIG. 5 shows a block diagram illustrating the exemplary ultrasound imaging system of FIG. 4.

FIG. 5 is a block diagram illustrating an embodiment of the imaging system 1 of FIG. 4. The imaging system 50 operates on a laboratory animal 64. The ultrasound probe 56 can be placed in proximity to the laboratory animal 64 to obtain image information.

The ultrasound system 81 includes a control subsystem 77, a scan converter 79, the transmit subsystem 68, the receive subsystem 70 and a user interface device 86. The processor 84 is coupled to the control subsystem 77 and a display 66. A memory 71 is coupled to the processor 84. The memory 71 can be any type of computer memory, and is typically referred to as random access memory "RAM," in which the software 73 of the ultrasound imaging system executes.

The ultrasound imaging system can be implemented using a combination of hardware and software. The hardware implementation of the ultrasound imaging system can include any or a combination of the following technologies, which are all well known in the art: discrete electronic components, a discrete logic circuit(s) having logic gates for implementing logic functions upon data signals, an application specific integrated circuit having appropriate logic gates, a programmable gate array(s) (PGA), a field programmable gate array (FPGA), etc.

The software for the ultrasound imaging system comprises an ordered listing of executable instructions for implementing logical functions, and can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

In the context of this document, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM), a read-only memory (ROM), an erasable programmable read-only memory (EPROM or Flash memory) (magnetic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

The memory 71 also includes the image data 60 obtained by the ultrasound system 81. A computer readable storage medium 88 is coupled to the processor for providing instructions to the processor to instruct and/or configure processor to perform steps or algorithms related to the operation of the ultrasound system 81, as further explained below. The computer readable medium can include hardware and/or software such as, by way of example only, magnetic disks, magnetic tape, optically readable medium such as a CD ROM, and semiconductor memory such as a PCMCIA card. In each case, the medium may take the form of a portable item such as a small disk, floppy diskette, cassette, or it may take the form of a relatively large or immobile item such as hard disk drive, solid state memory card, or RAM provided in the support system. It should be noted that the above listed example mediums can be used either alone or in combination.

The ultrasound system 81 includes a control subsystem 77 to direct operation of various components of the ultrasound system 81. The control subsystem 77 and related components may be provided as software for instructing a general purpose processor or as specialized electronics in a hardware implementation. The ultrasound system 81 includes a scan converter 79 for converting the electrical signals generated by the received ultrasound echoes to data that can be manipulated by the processor 84 and that can be rendered into an image on the display 66. The control subsystem 77 is connected to a transmit subsystem 68 to provide an ultrasound transmit signal to the ultrasound probe 56. The ultrasound probe 56 in turn provides an ultrasound receive signal to a receive subsystem 70. The receive subsystem 70 also provides signals representative of the received signals to the scan converter 79. The receive subsystem 70 is also connected to the control subsystem 77. The scan converter 79 is directed by the control subsystem 77 to operate on the received data to render an image for display using the image data 60.

The ultrasound system 81 transmits and receives ultrasound data through the ultrasound probe 56, provides an interface to a user to control the operational parameters of the imaging system 50, and processes data appropriate to formulate still and moving images that represent anatomy and/or physiology. Images are presented to the user through the interface display 66.

The human-machine interface 86 of the ultrasound system 81 takes input from the user, and translates such input to control the operation of the ultrasound probe 56. The human-machine interface 86 also presents processed images and data to the user through the display 66.

Once transmitted the ultrasound interacts with the laboratory animal's tissues and the contrast agent. The ultrasound is reflected by structures within the animal and scattered nonlinearly by the contrast agent. Echos resulting from interactions with the animal and contrast agent return to an ultrasound imaging system. After ultrasound is received it is processed to form an image. One embodiment of a system for receiving and processing reflected or scattered ultrasound is described in Example 1 below. Another embodiment is described in Example 2 below.

Ultrasound imaging systems may transmit pulsed energy along a number of different directions, or ultrasonic beams, and thereby receive diagnostic information as a function of both lateral directions across the body and axial distance into the body. This information may be displayed as two dimensional, "b-scan" images. Such a two-dimensional presentation gives a planar view, or "slice" through the body and shows the location and relative orientation of many features and characteristics within the body. Furthermore, by tilting or moving the ultrasonic sensor across the body, a third dimension may be scanned and displayed over time, thereby providing three-dimensional information.

Alternatively, ultrasound returns may be presented in the form of "m-scan" images, where the ultrasound echoes along a particular beam direction are presented sequentially over time, with the two axes being axial distance versus time. Thus, m-scan displays enable diagnosis of rapidly moving structures, such as heart valves.

Some ultrasound systems may combine both b-scan and m-scan images within the same display.

In one embodiment, high frequency pulsed-wave Doppler or color flow imaging may be used. A pulsed wave Doppler (PWD)/high frequency flow imaging system can also be used. Such a system can be modified for use with nonlinear signals. Systems can further be modified to enable nonlinear color flow imaging. Any of these systems can be used in combination with one for B-scan imaging. Any system can also be used in conjunction with filters, attenuators, pre-amplifiers and second filters as described in Example 2. Therefore the system can integrate PWD and color flow and also can enable nonlinear PWD in addition to color flow imaging.

Other ultrasound imaging systems may simultaneously present multiple ultrasound information, including b-scan, m-scan and doppler image displays, along with other information, such as EKG signals and/or phonograms.

Also provided is the use of a system for producing an ultrasound image using line-based image reconstruction with the contrast agents and the methods provided herein. One example of such a system may have the following components as described in U.S. patent application Ser. No. 10/736,232, U.S. patent application publication 20040236219, which is set forth in part below and is incorporated herein by reference. The system for producing an ultrasound image using line based image reconstruction can provide an ultrasound image having an effective frame rate in excess of 200 frames per second. The system incorporates an ECG based technique that enables significantly higher time resolution than what was previously available, thus allowing the accurate depiction of a rapidly moving structure, such as a heart, in a small animal, such as a mouse, rat, rabbit, or other small animal, using ultrasound (and ultrasound biomicroscopy). Biomicrosopy is an increasingly important application due to recent advances in biological, genetic, and biochemical techniques, which have advanced the mouse as a desirable test subject for the study of diseases, including the cardiovascular diseases.

In one aspect, the system for producing an ultrasound image using line based image resonstruction addresses specifically the need to image and analyze the motions of the heart of a small animal with proportionally relevant time and detail resolution. Such imaging is also applicable to imaging small structures within a human body. It also applies to other ultrasound imaging applications where effective frame rates greater than, for example, 200 frames per second are desired.

The human heart during rest beats regularly at a typical rate of 60-90 bpm (beats per minute). With clinical ultrasound, physicians generally desire 100 frames per heart beat to accurately depict motion, resulting in imaging frame rates of approximately 100 fps (frames per second). An adult mouse heart under similar conditions typically beats at a rate of 300-600 bpm. Therefore, to achieve 100 frames per heart beat, the desired imaging frame rate is approximately at or above 200-1000 fps, or higher.

Ultrasound images are formed by the analysis and amalgamation of multiple pulse echo events. An image is formed, effectively, by scanning regions within a desired imaging area using individual pulse echo events, referred to as "A-Scans", or ultrasound "lines." Each pulse echo event requires a minimum time for the acoustic energy to propagate into the subject and to return to the transducer. The image is completed by "covering" the desired image area with a sufficient number of scan lines, referred to as "painting in" the desired imaging area so that sufficient detail of the subject anatomy can be displayed. The number of and order in which the lines are acquired can be controlled by the ultrasound system, which also converts the raw data acquired into an image. Using a combination of hardware electronics and software instructions in a process called "scan conversion," or image construction, the ultrasound image obtained is rendered so that a user viewing the display can view the subject being imaged.

To decrease the amount of time required to obtain an image, the image is subdivided into regions, where each region corresponds to a single scan line. ECG signals acquired during the ultrasound scanning operation are used to time register individually the subdivided data (i.e., the individual pulse-echo events," or "raw data" associated with each scan line). A scan conversion mechanism utilizes the ultrasound lines, which are time registered with the ECG signal, to develop an image having an effective frame rate significantly greater that the frame rate than may be obtained in real-time. A sequential series of image frames is reconstructed from the pool of time and position registered raw data to reconstruct a very high precision (i.e., high frame rate) representation of the rapidly moving structure.

Figure 6:
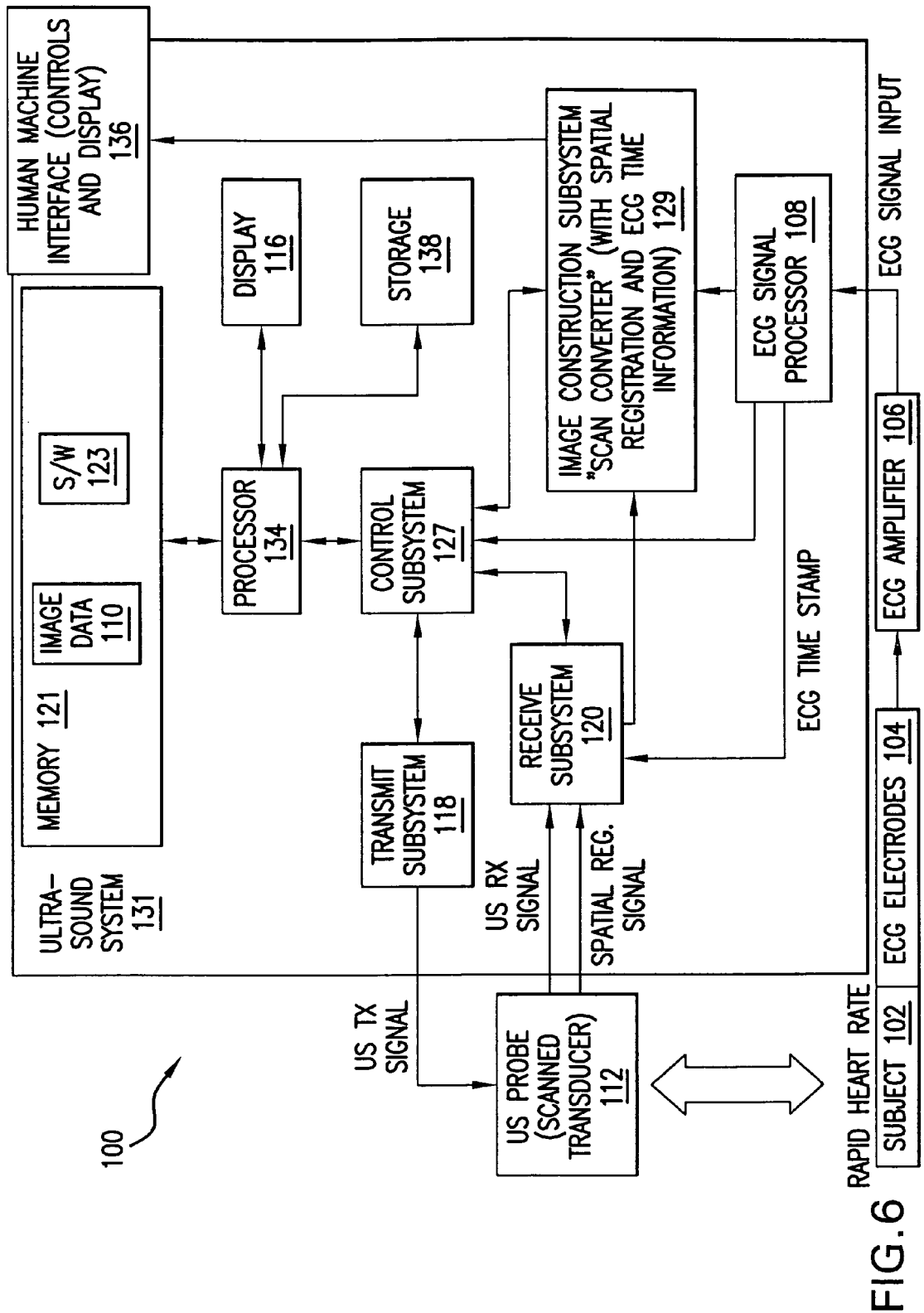
FIG. 6 shows a block diagram of an exemplary ultrasound imaging system that can be used with the disclosed compositions and methods.

FIG. 6 is a block diagram illustrating an imaging system 100. The system 100 operates on a subject 102. An ultrasound probe 112 is placed in proximity to the subject 102 to obtain image information. The ultrasound probe generates ultrasound energy at high frequencies, such as but not limited to greater than 20 MHz and including 25 MHz, 30 MHz, 35 MHz, 40 MHz, 45 MHz, 50 MHz, 55 MHz, 60 MHz and higher. Further, ultrasound operating frequencies significantly greater than those mentioned above are also contemplated. The subject 102 is connected to electrocardiogram (ECG) electrodes 104 to obtain a cardiac rhythm from the subject 102. The cardiac signal from the electrodes 104 is transmitted to an ECG amplifier 106 to condition the signal for provision to an ultrasound system 131. It is recognized that a signal processor or other such device may be used instead of an ECG amplifier to condition the signal. If the cardiac signal from the electrodes 104 is suitable, then use of an amplifier 106 or signal processor could be avoided entirely.

The ultrasound system 131 includes a control subsystem 127, an image construction subsystem 129, sometimes referred to as a "scan converter," the transmit subsystem 118, the receive subsystem 120 and the user input device 136. The processor 134 is coupled to the control subsystem 127 and the display 116 is coupled to the processor 134. A memory 121 is coupled to the processor 134. The memory 121 can be any type of computer memory, and is typically referred to as random access memory "RAM," in which the software 123 of the invention executes. The software 123 controls the acquisition, processing and display of the ultrasound data allowing the ultrasound system 131 to display a high frame rate image so that movement of a rapidly moving structure may be imaged. The software 123 comprises one or more modules to acquire, process, and display data from the ultrasound system 131. The software comprises various modules of machine code which coordinate the ultrasound subsystems, as will be described below. Data is acquired from the ultrasound system, processed to form complete images, and then displayed to the user on a display 116. The software 123 allows the management of multiple acquisition sessions and the saving and loading of these sessions. Post processing of the ultrasound data is also enabled through the software 123.

The system for producing an ultrasound image using line-based image reconstruction can be implemented using a combination of hardware and software. The hardware implementation of the system for producing an ultrasound image using line based image reconstruction can include any or a combination of the following technologies, which are all well known in the art: discrete electronic components, a discrete logic circuit(s) having logic gates for implementing logic functions upon data signals, an application specific integrated circuit having appropriate logic gates, a programmable gate array(s) (PGA), a field programmable gate array (FPGA), etc.

The software for the system for producing an ultrasound image using line based image reconstruction comprises an ordered listing of executable instructions for implementing logical functions, and can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

In the context of this document, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM), a read-only memory (ROM), an erasable programmable read-only memory (EPROM or Flash memory) (magnetic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

The memory 121 can include the image data 110 obtained by the ultrasound system 100. A computer readable storage medium 138 is coupled to the processor for providing instructions to the processor to instruct and/or configure processor to perform steps or algorithms related to the operation of the ultrasound system 131, as further explained below. The computer readable medium can include hardware and/or software such as, by way of example only, magnetic disks, magnetic tape, optically readable medium such as a CD ROM, and semiconductor memory such as a PCMCIA card. In each case, the medium may take the form of a portable item such as a small disk, floppy diskette, cassette, or it may take the form of a relatively large or immobile item such as hard disk drive, solid state memory card, or RAM provided in the support system. It should be noted that the above listed example mediums can be used either alone or in combination.

The ultrasound system 131 can include a control subsystem 127 to direct operation of various components of the ultrasound system 131. The control subsystem 127 and related components may be provided as software for instructing a general purpose processor or as specialized electronics in a hardware implementation. The ultrasound system 131 includes an image construction subsystem 129 for converting the electrical signals generated by the received ultrasound echoes to data that can be manipulated by the processor 134 and that can be rendered into an image on the display 116. The control subsystem 127 is connected to a transmit subsystem 118 to provide an ultrasound transmit signal to the ultrasound probe 112. The ultrasound probe 112 in turn provides an ultrasound receive signal to a receive subsystem 120. The receive subsystem 120 also provides signals representative of the received signals to the image construction subsystem 129. The receive subsystem 120 is also connected to the control subsystem 127. The scan converter 129 is directed by the control subsystem 127 to operate on the received data to render an image for display using the image data 110.

The ultrasound system 131 can include an ECG signal processor 108 configured to receive signals from the ECG amplifier 106. The ECG signal processor 108 provides various signals to the control subsystem 127. The receive subsystem 120 also receives an ECG time stamp from the ECG signal processor 108. The receive subsystem 120 is connected to the control subsystem 127 and an image construction subsystem 129. The image construction subsystem 129 is directed by the control subsystem 127.

The ultrasound system 131 transmits and receives ultrasound data through the ultrasound probe 112, provides an interface to a user to control the operational parameters of the imaging system 100, and processes data appropriate to formulate still and moving images that represent anatomy and/or physiology. Images are presented to the user through the interface display 116.

The human-machine interface 136 of the ultrasound system 131 takes input from the user, and translates such input to control the operation of the ultrasound probe 106. The human-machine interface 136 also presents processed images and data to the user through the display 116.

The software 123 in cooperation with the image construction subsystem 129 operate on the electrical signals developed by the receive subsystem 120 to develop a high framerate ultrasound image that can be used to image rapidly moving anatomy of the subject 102.

Figure 7A:
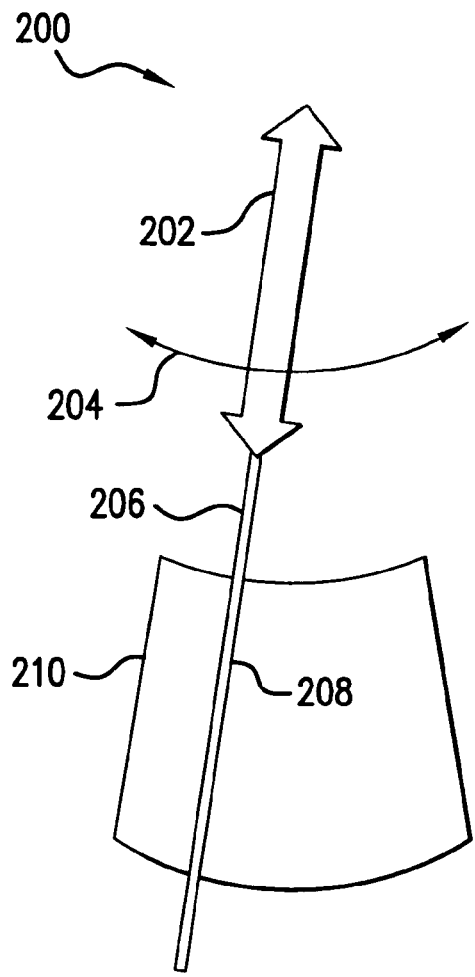
FIGS. 7A and 7B show schematic representations depicting methods of ultrasound imaging using the disclosed compositions and methods.
Figure 7B:
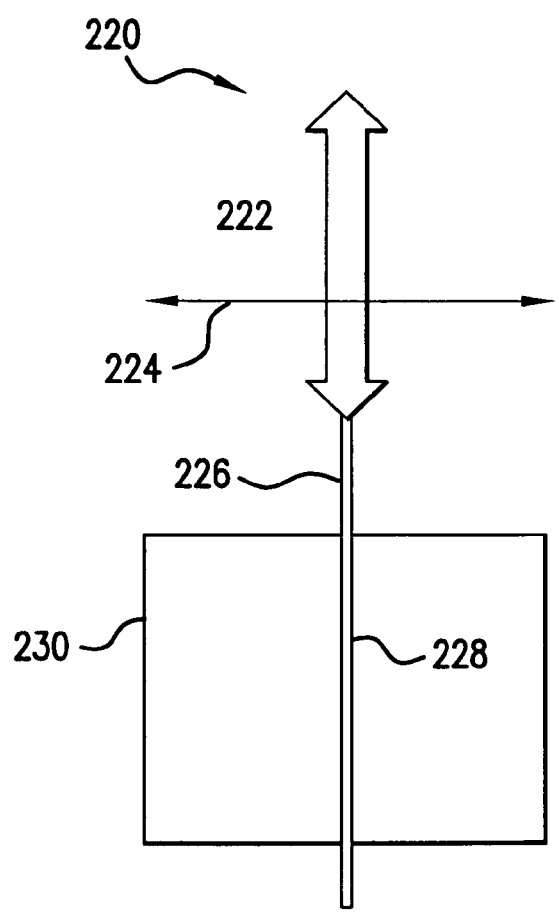

FIGS. 7A and 7B are schematic representations depicting methods of ultrasound imaging. In FIG. 7A, the operation of the ultrasound probe 112 in a sector format scan is illustrated generally. In FIG. 7A, use of the ultrasound probe 112 to obtain a sector format image is shown by the numeral 200. An ultrasound signal propagates in direction 202 projecting a "line" 206 of ultrasound energy. The ultrasound probe 112 moves along an arc 204. The ultrasound signal thus images, or "paints in," a portion 208 of a sector format image 210.

An alternative format of image is shown in FIG. 7B by the numeral 220. The ultrasound probe 112 propagates a signal in direction 222 projecting a "line" 226 of ultrasound energy. The position of the ultrasound probe 112 moves along a line 224. The ultrasound signal thus images, or "paints in," a portion 228 of rectangular format image 230.

It will be recognized that many other formats of images may be used with the ultrasound probe 112. Any technique that acquires spatially limited data may be used, including painting in a region, two-dimensional, and three-dimensional imaging.

The control subsystem 127 coordinates the operation of the ultrasound probe 112, based on user selected parameters, and other system inputs.

The control subsystem 127 ensures that data is acquired at each spatial location, and for each time window relative to the ECG signal. Therefore, a full data set includes raw data for each time window along the ECG signal, and for each spatial portion of the image frame. It is recognized that an incomplete data set may be used with appropriate interpolation between the values in the incomplete data set being used to approximate the complete data set.

The transmit subsystem 118 generates ultrasound pulses based on user selected parameters. The ultrasound pulses are sequenced appropriately by the control subsystem 127 and are applied to the probe 112 for transmission toward the subject 102.

The receive subsystem 120 records the echo data returning from the subject 102, and processes the ultrasound echo data based on user selected parameters. The receive subsystem 120 also receives a spatial registration signal from the probe 112 and provides position and timing information related to the received data to the image construction subsystem 129.

Figure 8A:
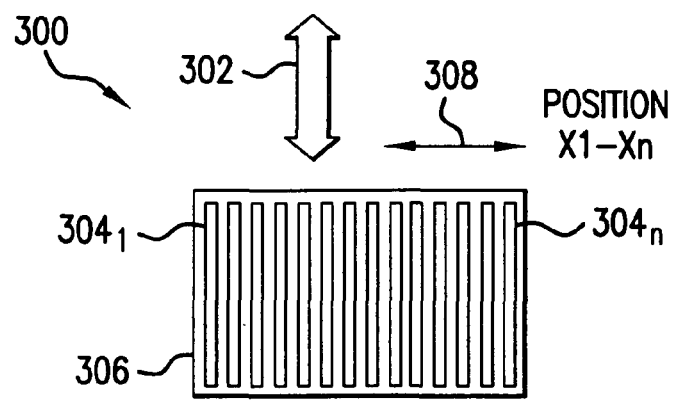

FIGS. 8A through 8E are schematic diagrams illustrating the operation of the system for producing an ultrasound image using line-based image reconstruction. The operation described below may be implemented using the software 123 to control the operation ultrasound system 131. FIG. 8A shows an ultrasound frame 300. The ultrasound probe 112 (FIG. 6) produces an ultrasound signal along line 302. FIG. 8A shows an exemplary representative signal which shows the general form of ultrasound signals. Each position of the ultrasound probe 112 along the line 308 provides a scan line 304 in the rectangular format image frame 306. The scan lines are labelled $304_1$ through $304_n$, depending on the number of lines per frame.

Figure 8B:
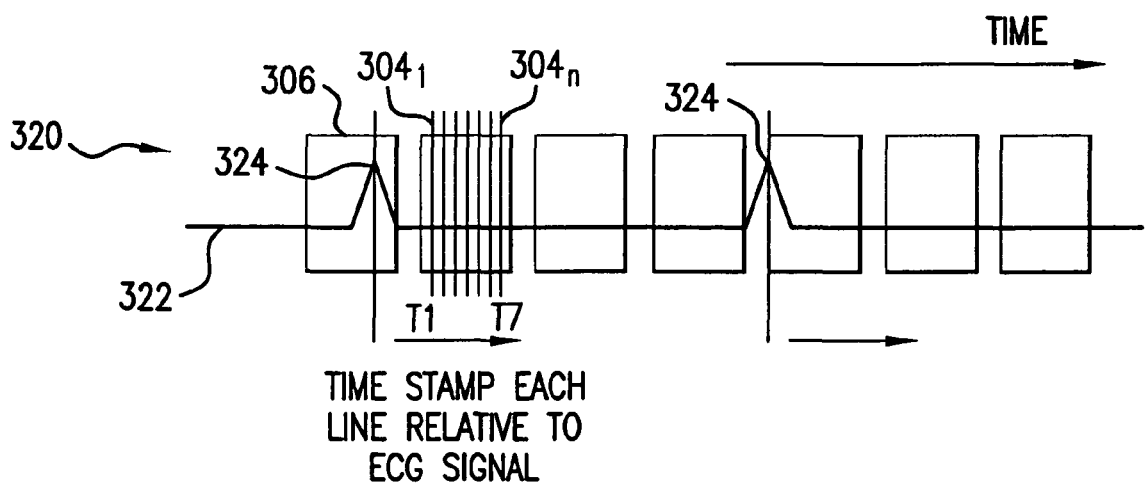

FIG. 8B is a schematic diagram 320 showing a plurality of image frames 306 along a cardiac rhythm trace 322. By monitoring the ECG signal using the ECG signal processor 108 (FIG. 6), a specific point 324 in the cardiac rhythm trace 322 may be identified, and a time stamp obtained for each line 304 relative to and offset from the point 324. The point 324 is referred to as the peak of the R wave. Thus, by collecting the same line 304 in frames 306, with each line 304 in each frame having the same offset from the point 324, an acquisition sequence 340, as shown in FIG. 8C, is obtained. The acquisition sequence 340 comprises frames 306 in which the same scan line 304 is collected, thus yielding a full cycle of the heart between points 324. As shown in FIG. 8D, the frames 306 may be reconstructed by reassembling multiple scan lines $304_1$ and $304_2$, for example. Each position Xn, Xn+1 of the ultrasound probe 112 yields lines at times T1, T2, . . . , T7 shown in FIG. 8E.

During image acquisition, the image construction subsystem 129 records as input all of the raw data associated with the scan lines 304, including position and ECG-time registration information for each line. When an amount of data sufficient to provide an acceptable image has been collected, the control subsystem 127 sends a signal to the image construction subsystem 129 initiating a reconstruction sequence in which the raw data for each scan line 304 is assembled into a complete image, by collecting sub-regions (i.e., individual scan lines 304) of the image. The sub-regions are temporally relative to a specific point 324 in the ECG cycle and generally correspond to the cardiac cycle from R wave to R wave. The assembly of the individual scan lines over a series of image frames results in a sequential time-series of complete image frames. When viewed, the time-series of constructed image frames appears to have an effective frame rate in excess of 200 fps and appears as a smooth and accurate depiction of rapidly moving structures.

The minimum time of frame acquisition represented is thus the maximum time required to obtain each raw data scan line 304, rather than the time required to obtain an entire image frame 306, thus providing an effective frame rate much greater that what would be obtained using real-time or frame-based image reconstruction.

Figure 9:
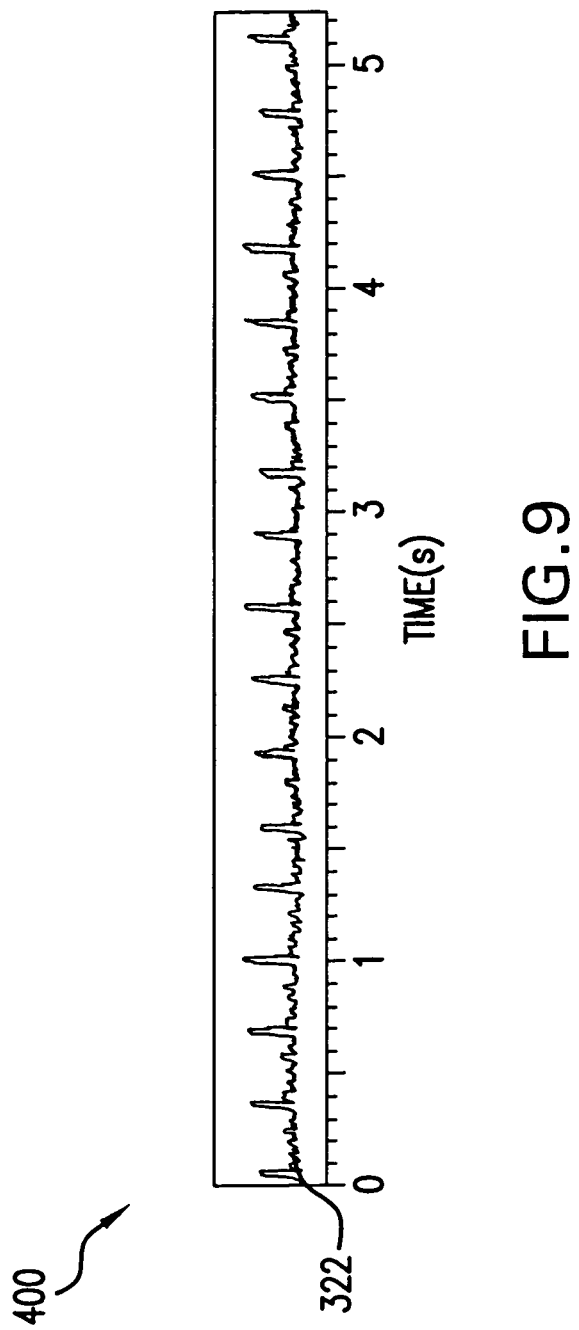
FIG. 9 shows an exemplary electrocardiogram signal used in the system of FIG. 6.

An exemplary ECG signal is shown in FIG. 9 by the numeral 400. The ECG signal is represented by the trace 322. The ECG signal processing module 108 (FIG. 6) of the ultrasound system 131 automatically detects, using peak detection of the R-wave pulse, a fixed and repeatable point (324 in FIG. 8B) on the ECG signal trace 322 from which the scan lines 304 are referenced in time. This automatically detects a point in time which is used as the origin for relative ECG time stamps for each element of raw data associated with each can line.

Figure 10:
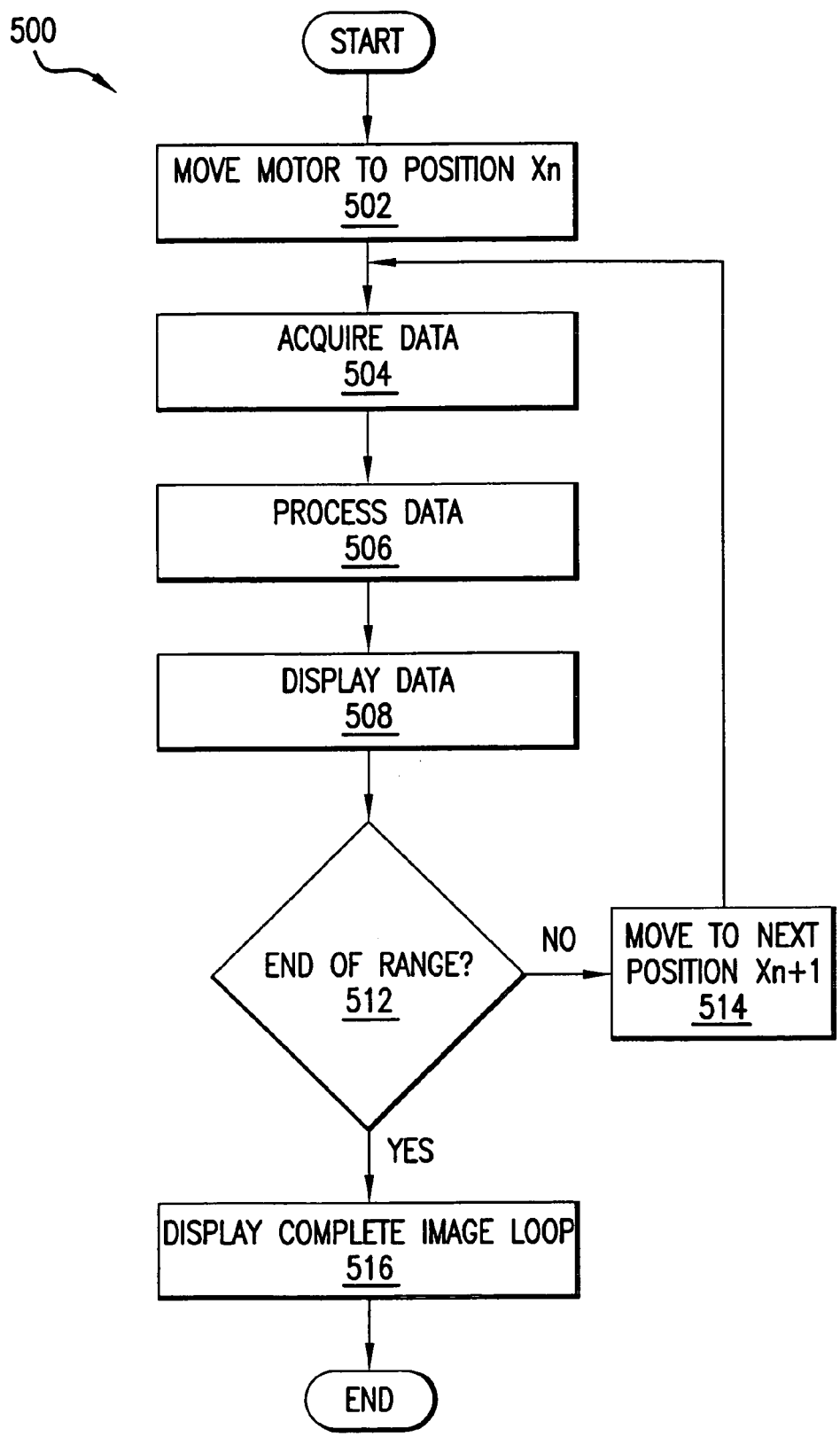
FIG. 10 shows a flowchart illustrating the overall operation of the system for producing an ultrasound image using line based image reconstruction that can be used with the disclosed compositions and methods.
Figure 11:
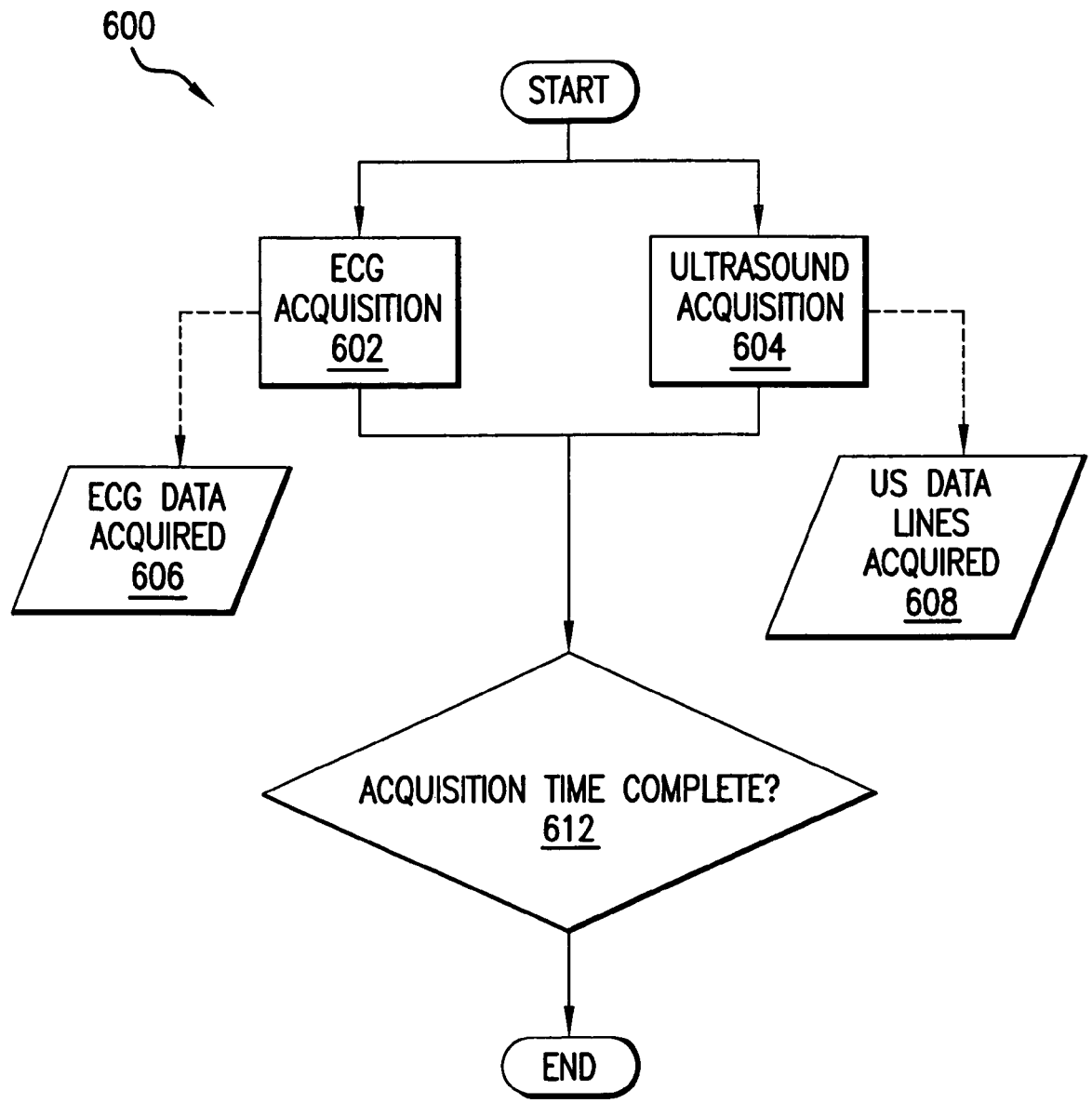
FIG. 11 shows a flowchart illustrating the operation of the acquisition block of FIG. 10.
Figure 12:
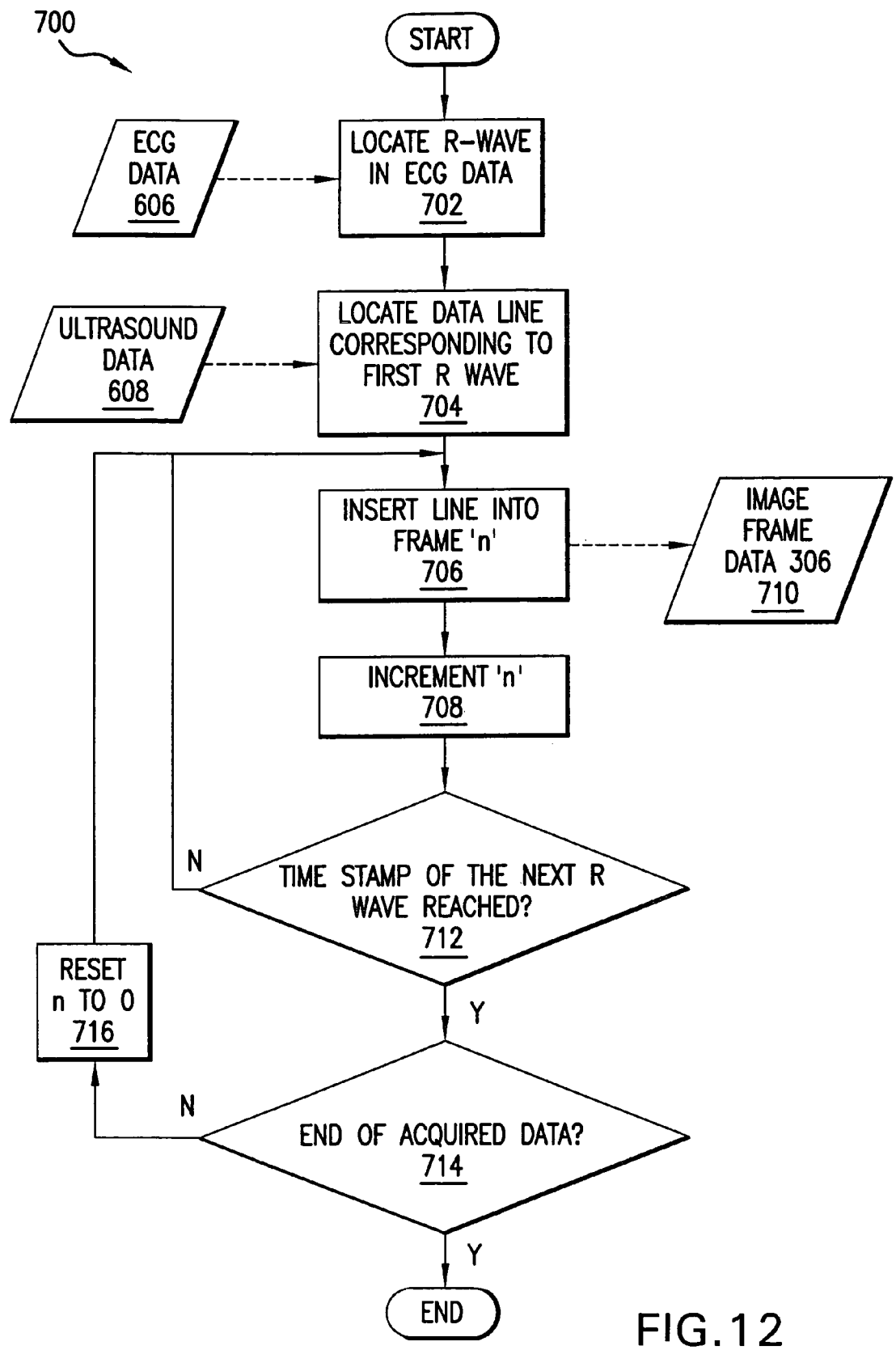
FIG. 12 shows a flowchart illustrating the operation of the process data block of FIG. 10.

FIGS. 10, 11 and 12 are flowcharts collectively illustrating the operation of the system for producing an ultrasound image using line based image reconstruction. The blocks in the flowcharts may be executed in the order shown, out of the order shown, or concurrently.

FIG. 10 is flowchart 500 illustrating the overall operation of the system for producing an ultrasound image using line based image reconstruction. In block 502, the transducer in the probe 112 is registered at its home position at one end of its travel. The movement of the transducer 112 is described in U.S. patent application Ser. No. 10/683,890, U.S. patent application publication 20040122319, entitled "High Frequency, High Frame-Rate Ultrasound Imaging System, which is incorporated herein by reference. In block 504, ultrasound data is acquired for the probe location described in block 502 and stored in memory 121 (FIG. 6). The operation of block 504 will be described in greater detail in FIG. 11.

In block 506, the data acquired in block 504 is processed. The operation of block 506 will be described in greater detail in FIG. 12.

In block 508, the data acquired in block 504 and processed in block 506 is displayed. In block 512 it is determined whether the probe 112 has reached the end of its travel, or sweep. If the probe 112 has not reached the end of its travel, its position is incremented in block 514 and the process returns to block 504 and data acquisition continues. If, in block 512 it is determined that the probe 112 has reached the end of its travel, then, in block 516, a line based reconstructed image is displayed on display 116 as what is referred to as a "B mode" loop.

FIG. 11 is a flowchart 600 illustrating the operation of the acquisition block 504 of FIG. 10. In block 602 ECG data is acquired and stored in memory 121 in block 606. In block 604, ultrasound data is acquired and stored in memory 121 in block 608. Each line 304 (FIG. 8A and FIG. 8B) of ultrasound data is stored in block 608. The ultrasound signal includes the data associated with a scan line and also includes a spatial registration signal associated with the scan line. The ultrasound signal containing the raw data and the spatial registration information is identified with the time stamp by the receive subsystem 120.

In block 612 ECG and ultrasound data acquisition is continued for a period of time specified by a user of the system. The time period specified in block 612 determines the number of ultrasound data lines 304 (FIGS. 8A and 8B) are acquired at a particular probe position. A sufficient amount of data is obtained when at least one heart cycle of data has been collected. Collecting data over more than one heart cycle improves the accuracy of the image.

FIG. 12 is a flowchart 700 illustrating the operation of the process data block 506 of FIG. 10. In block 702, the ECG data stored in block 606 (FIG. 11) is scanned to locate the first specific point 324 in the R wave (326a and 326b) as shown in FIG. 8B as described above. This automatically detects a point in time which is used as the origin for relative ECG time stamps for each element of raw data associated with each can line. Once the peak 324 is located, a corresponding point in the ultrasound data stored in block 608 is located in block 704. In block 706, each line 304 of ultrasound data following this point is placed, in block 710, into a reconstructed frame 306 (FIGS. 8C and 8D) based on its time displacement from the peak 324. For example, a line 304 acquired Tn milliseconds after the peak 324 will be placed into frame Tn.

In block 712 it is determined whether the peak 324 of the next R wave has been reached. If the peak 324 of the next R wave has not been reached, the process returns to block 706. If, in block 712 it is determined that the next peak 324 has been reached, then, in block 714, it is determined whether there is any additional data to process. If there is additional data to process, the image reconstruction subsystem 129 resets its time counter in block 716. If, in block 714 it is determined that there is no additional data to process, then the process ends.

Figure 13:
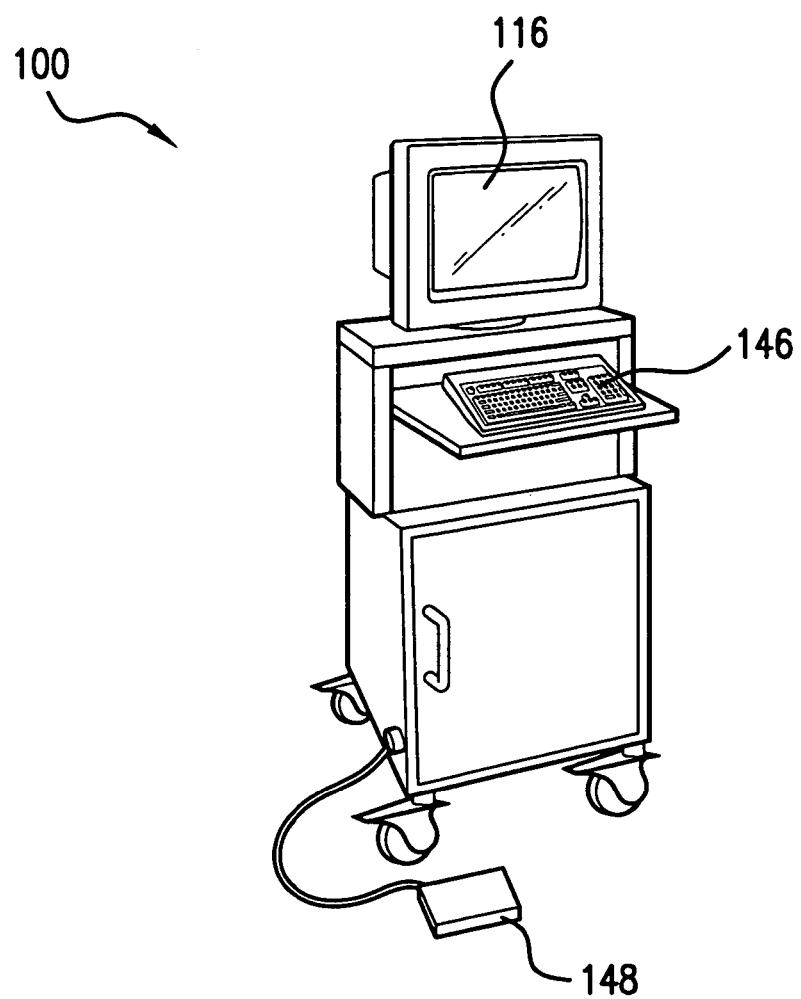
FIG. 13 shows a schematic view of an ultrasound system of FIG. 6 or FIG. 4.

Referring to FIG. 13, an embodiment of the imaging system 100 or 50 is shown by way of example only. In this example, the imaging system 100 or 50 is a free-standing unit on casters for mobility. The human machine interface 136 or 86 includes a display 116 or 66, a keyboard 146, and a foot control 148. The control subsystem 127 or 77 and related components are located inside a case.

Figure 14:
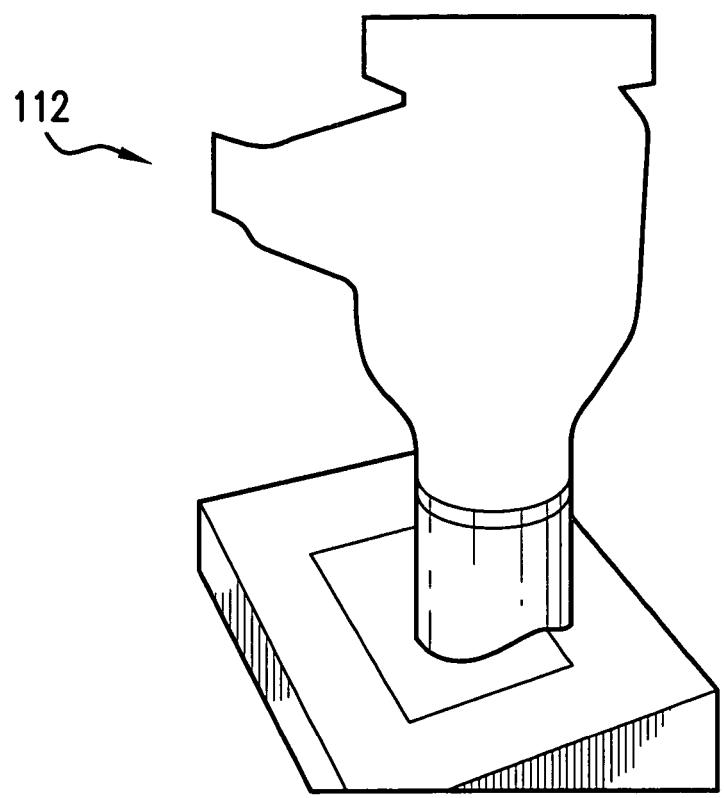
FIG. 14 shows a schematic view of an ultrasound scanhead of FIG. 6 or FIG. 4.

Referring to FIG. 14, an embodiment of the ultrasound probe 112 or 56 is shown by way of example only. The purpose of the ultrasound probe 112 or 56 is to generate and receive ultrasound signals, and feed these signals back to the ultrasound system 131 or 81, with position registration of each of the scan lines containing the raw data.

The ultrasound probe 112 or 56, also referred to as a scan head comprises a piezoelectric element(s) to convert ultrasound pressure waves to electrical signals, and received ultrasound pressure waves to electrical signals, and a mechanism to reposition (and record spatial location of) the ultrasound beam. In one embodiment, the positioning mechanism comprises an optical position encoder connected to a high resolution stepping motor as described in U.S. patent application Ser. No. 10/683,890, U.S. patent publication 20040122319, entitled "High Frequency, High Frame-Rate Ultrasound Imaging System, which is incorporated herein by reference. In another embodiment, the positioning mechanism comprises an array of piezoelectric elements which can be electronically steered using variable pulsing and delay mechanisms. Regardless of the positioning mechanism used, the position of each scan line is determined and associated with each scan line as described in FIG. 6.

Figure 15:
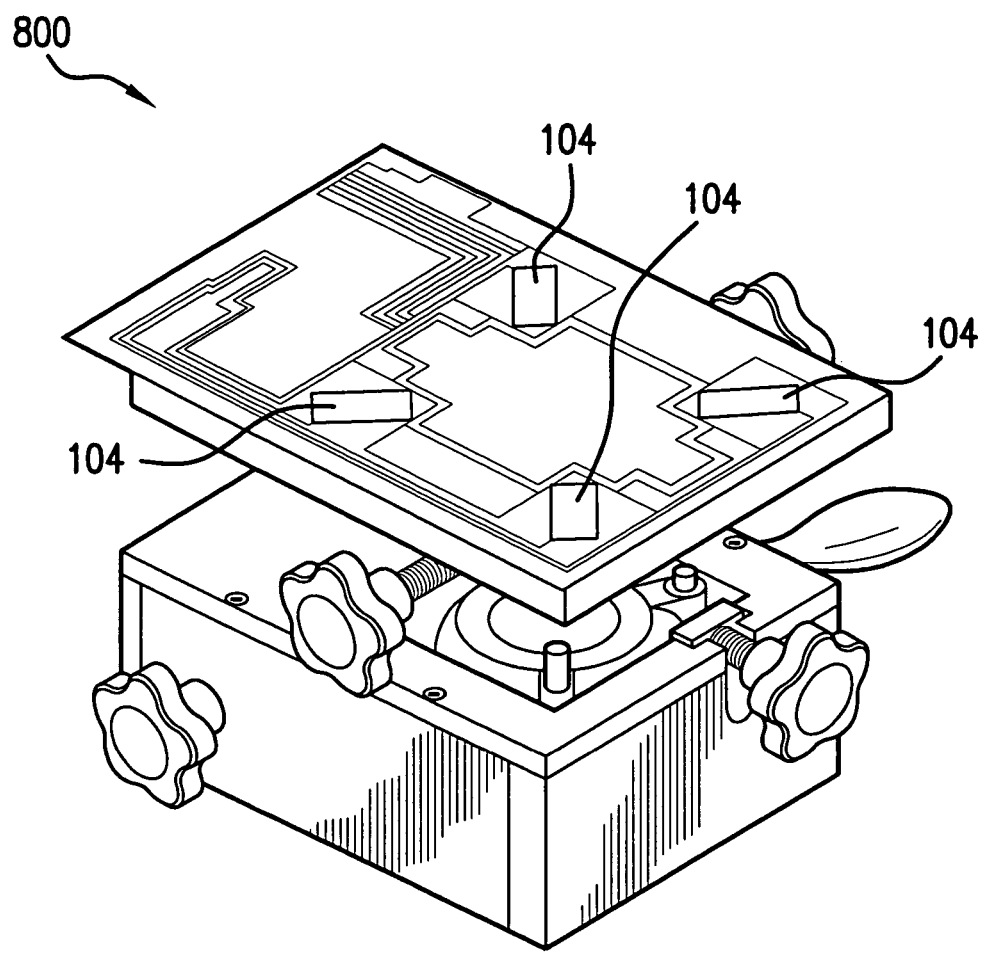
FIG. 15 shows a schematic view of the electrodes of FIG. 6 or FIG. 4.
Figure 16:
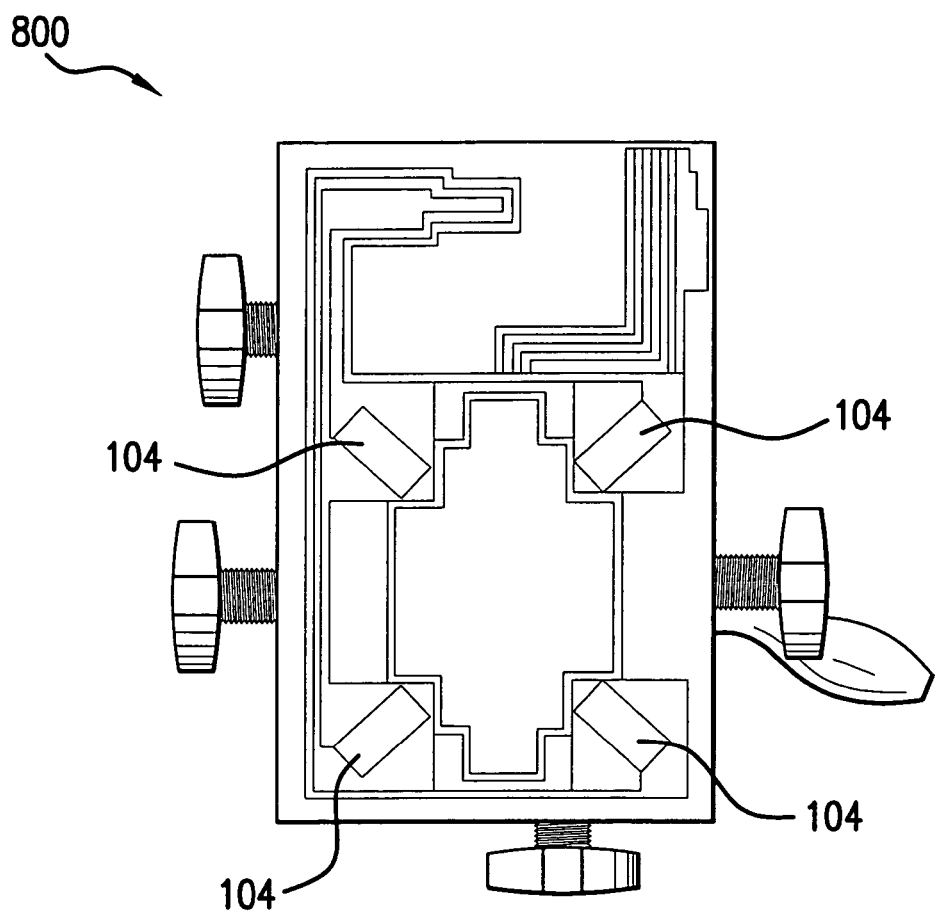
FIG. 16 shows a plan view of FIG. 15.

Referring to FIGS. 15 and 16, an embodiment of an ECG apparatus 800 is shown in more detail. The ECG apparatus comprises ECG electrodes 104, and an ECG amplifier 106 (FIG. 6). The ECG amplifier 106 is typically located close to the ECG electrodes 104 (FIG. 6) in a control module (not shown) which also controls a small animal heating element (not shown).

The embodiment of FIGS. 15 and 16 illustrates an example of a set of ECG electrodes designed to collect ECG signals from an adult mouse. Furthermore, knobs (not shown) are provided to adjust the position of the platform as required in various procedures. A control provides a quick height adjustment for the platform. A knob operates a magnet for holding the platform in position and allowing a quick release for coarse positioning of the platform.

Since the strength of the ECG signal obtained from a small animal is weak, the signal is amplified prior to being transmitted to the ultrasound system.

By accurately registering the position of the probe 112 for each scan line, the time of acquisition of each scan line relative to a reference point in the ECG trace 322 (FIG. 8B), each scan line having a raw data element, an effective frame rate at or in excess of 200 frames per second can be achieved during playback of a fully reconstructed data set. An ultrasound system constructed in accordance with the invention records both position registration with respect to the probe 112 and time registration with respect to the scan line relative to the ECG cycle, thus identifying each raw data element. The raw data elements are then used to construct a high precision high frame rate image.

First implementations have demonstrated the capability to acquire image sequences with complete data independence at for example 1000 frames per second. It is anticipated that operations may be performed at much higher frame rates. The frame rate may be as high as the pulse repetition frequency (PRF) limit for any given ultrasound line. The PRF limits the maximum image depth. The maximum image depth is equal to the speed of sound divided by twice the PRF (i.e. speed of sound/(2*PRF)). It is anticipated that this could be as high as approximately 100,000 frames per second.

It will therefore be recognized that a control subsystem has been provided which coordinates the acquisition of raw data (ultrasound lines or "A-Scans") ensuring that data is acquired at each spatial location, for each time window relative to the ECG signal.

Furthermore, an image construction subsystem (or scan converter) has been provided which is capable of reconstructing a sequence of spatially complete image frames at each time window relative to the ECG signal.

The above methods and compounds can also be used with human subjects for ophthalmology and dermatology imaging applications with typical human administration.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for.

Example 1

High Frequency Nonlinear B-Scan Imaging of Microbubble Contrast Agents

High Frequency Nonlinear Imaging System

Figure 17:
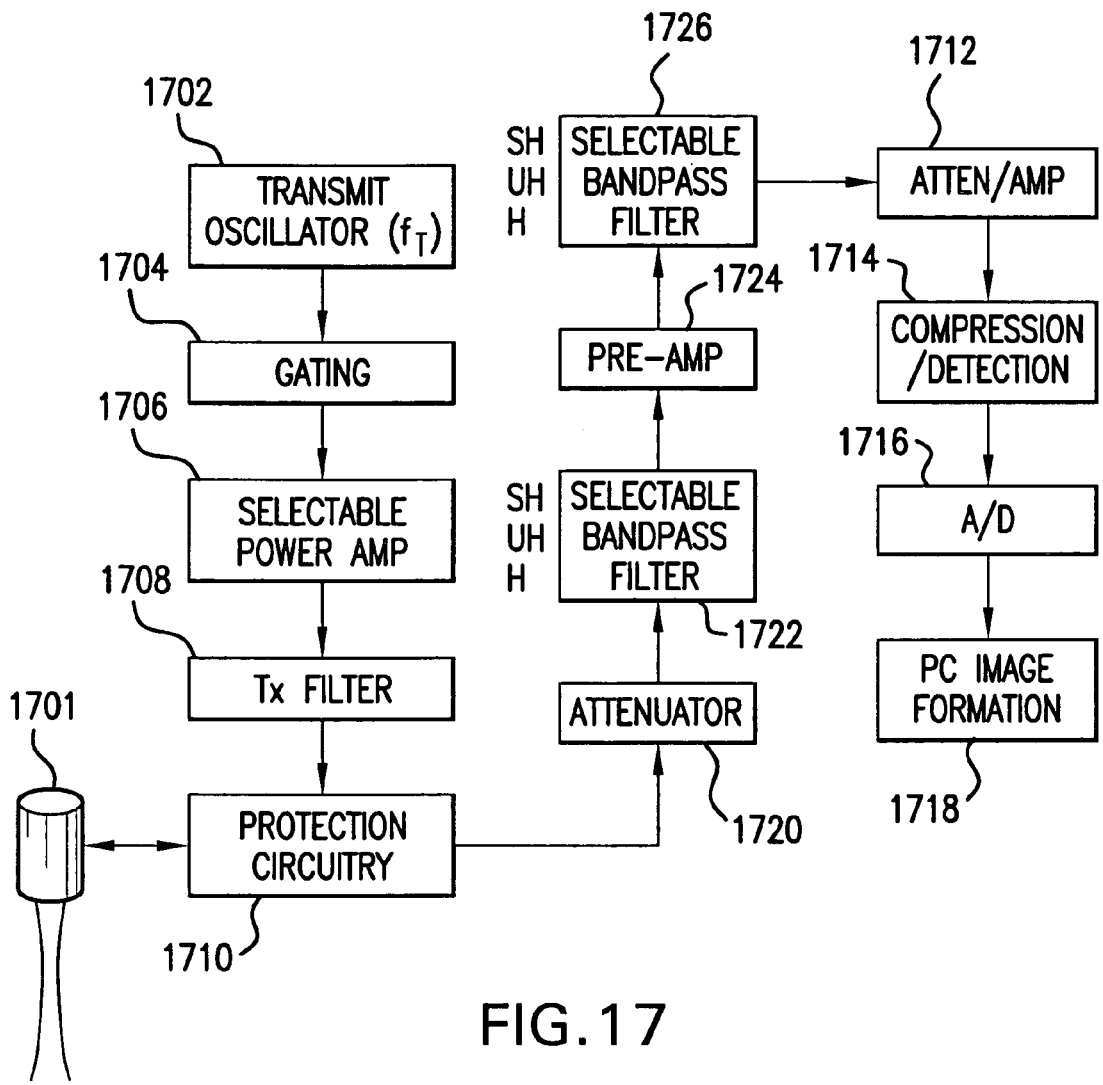
FIG. 17 shows a block diagram overview of the main components of an exemplarly nonlinear B-scan imaging system. The original linear imaging UBM system elements have been modified by the introduction of a transmit filter and received signals are conditioned by an additional amplification and filtering stage (shaded blocks). Nonlinear signals in the SH20, UH20, Sec20, or SH30 are isolated by selection of the appropriate filters.

A Visualsonics UBM system (model VS40 Visualsonics Inc., Toronto, Canada) was modified to permit the sensitive detection of nonlinear scattering. Foster et al., (2002) Ultrasound Med. Biol. 1165-1172. Alternatively a Vevo 660 or another high frequency ultrasound system could be utilized. The system employed a mechanically scanned single element transducer and images were constructed from a consecutive series of pulse-echo lines obtained during linear translation. A block diagram overview of the relevant system components is shown in FIG. 17, where modifications made to permit nonlinear imaging have been highlighted.

A. Transmit Sub-System

On the transmit side, a low amplitude pulse was generated by gating the output of a reference transmit oscillator 1702. For example a sinusoidal oscillator can be used. Both the oscillator frequency and gate length are selectable, thereby giving substantial control over the center frequency and pulse bandwidth. The gate length can be selected using a gating element 1704. The resulting low amplitude pulse was then amplified using a selectable power amplifier 1706 to a level appropriate for ultrasound pulse generation. In the original VS40 configuration, this pulse passes directly into protection circuitry comprising an expander, a limiter/pre-amplifier combination. After the received signal exits the limiter/pre-amplifier combination it enters the receive sub-system of the UBM.

The frequency content of the original high amplitude transmit pulse was found to have significant energy outside of the desired transmit bandwidth. This was due in part to the gating process, which introduces frequency domain side lobes about the main lobe of center frequency energy. It was also due to second and third harmonics introduced by the power amplification stage. While this energy may not be significant in linear imaging mode, it can seriously degrade the performance of a nonlinear imaging system. An analog transmit filtering stage 1708 was introduced after the power amplification output to remove this energy. For the 20 MHz transmit, an 8th order band pass filter was used with −3 dB points at 16.7 MHz and 24.9 MHz, and −20 dB points at 15.2 MHz and 25.5 MHz. For the 30 MHz transmit, an 8th order band pass filter with −3 dB points at 25.8 MHz and 34.3 MHz, and −20 dB points at 24.4 MHz and 36.8 MHz was employed. With these filters, the transmitted second harmonic levels were reduced to levels less than −50 dB. The filtered high-voltage signal exiting the power amplified was measured using a Lecroy 520 oscilloscope (Chestnut Ridge, N.Y.). The second harmonic level was found to be below the noise floor of the oscilloscope, which was −50 to −53 dB relative to the fundamental frequency peak, depending on the transmit setting.

The convention used to describe the frequency ranges of interest is: FN20 (fundamental 20 MHz), SH20 (subharmonic of a 20 MHz transmit—i.e. 10 MHz), UH20 (ultraharmonic of a 20 MHz transmit—i.e. 30 MHz), Sec20 (second harmonic of a 20 MHz transmit—i.e. 40 MHz), FN30 (fundamental 30 MHz), and SH30 (subharmonic of a 30 MHz transmit—i.e. 15 MHz).

B. Receive Sub-System

On the receive side of the original UBM system, signals exiting protection circuitry 1710 enter an amplification and filtering stage 1712, followed by a logarithmic compression/envelope detection stage 1714. The signals were subsequently digitized using an analog to digital converter (A/D) 1716 and image line formation and display are carried out on a PC platform 1718. A vertical image line was derived from a single pulse-echo signal that was triggered based on the transducer position within the image plane. Each image was composed of 512 equally spaced pulse echo lines.

For nonlinear imaging, the received signals were conditioned by the introduction of an additional analog filtering and amplification stage. This stage comprised a series configuration of an attenuator 1720, filter 1722, pre-amplifier 1724, and a second filter 1726. The attenuator (Minicircuits, Brooklyn, N.Y.) value was selected to prevent amplifier saturation and was typically between 3-10 dB. A pre-amplifier (either a 59 dB model AU-1341 or a 40 dB model AU-1341, Miteq, Hauppauge, N.Y.) provided the additional signal gain necessary to detect potentially small nonlinear signals. The first filter was used in order to remove the majority of the fundamental frequency signal and thereby permit a more efficient use of the effective dynamic range of the amplifier. The second filtering stage was used to exclude the remainder of tissue signals, as well as to reject wideband pre-amplifier noise outside of the frequency range of interest.

By employing the appropriate receive filters, images were formed using energy in either the fundamental (linear imaging) or one of the three nonlinear frequency ranges. A combination of custom designed $8^{th}$ order band pass filters and commercially available filters was used to isolate the nonlinear signals from the fundamental frequency signals. Table 1 summarizes the filters used for each of the SH20, UH20, Sec20, and SH30 imaging modes. Receive filter characteristics for each of the nonlinear imaging modes. HPF (MC) denotes a commercially available high-pass filter (Minicircuits, Brooklyn, N.Y.), while the remainder are custom designed band-pass filters.

TABLE 1

|  |  | Filter 1 (MHz) | Filter 2 (MHz) |
|---|---|---|---|
| SH20 | −3 dB | 7.0-11.5 | 7.0-11.5 |
|  | −20 dB | 6.4-13.0 | 6.4-13.0 |
| UH20 | −3 dB | 25.0 HPF (MC) | 28.3-33.4 |
|  | −20 dB | 29.0 | 27.5-34.3 |
| Sec20 | −3 dB | 25.0 HPF(MC) | 35.4-44.8 |
|  | −20 dB | 29.0 | 33.0-47.6 |
| SH30 | −3 dB | 11.1-18.5 | 11.1-18.5 |
|  | −20 dB | 16.4-20.7 | 16.4-20.7 |

C. Transducer Characteristics

A custom made spherically focused co-polymer transducer 1701 (8 mm aperture, 20 mm focal length) was employed as described by Foster and Sherar (1989) Ultrason. Imaging, 11: 75-94. At 20 MHz, the theoretical (Kino (1987) Acoustic Waves: Devices, Imaging and analog Signal Processing) −3 dB depth of field was 8.2 mm and beam width was 0.187 mm. At 30 MHz, the theoretical −3 dB depth of field was 5.5 mm and beam width was 0.125 mm. The transducer bandwidth was selected primarily to have sensitivity to nonlinear signals (SH, UH, and SecH) associated with a transmit frequency of 20 MHz. The frequency response of the transducer was measured using the pulse-echo response from a quartz flat. A low amplitude broadband pulse was employed and the results were corrected for the path length attenuation in water (0.000221 dB/(mm.MHz$^2$)). The transducer had a center frequency of 19 MHz and −12 dB points at 5 MHz and 32 MHz. The sensitivity of the transducer at the nonlinear center frequencies of SH20 (10 MHz), UH20 (30 MHz), and Sec20 (40 MHz), relative to its peak sensitivity at 19 MHz, was −4 dB, −9 dB, and −15 dB respectively. This frequency response also made it possible to examine the SH30, with a relative sensitivity of −3dB at the SH30 center frequency of 15 MHz.

In pulse-echo imaging, the effective lateral resolution is a function of both the transmit and receive beam widths. In a linear high-frequency, single-element, pulse-echo imaging system, the transmit and receive lateral beam functions is identical. In a nonlinear imaging system, the difference between the transmit and receive center frequencies contributes to creating a lateral resolution that is intermediate between these two cases. Theoretical estimates of the effective pulse-echo lateral resolution (i.e., −6 dB two-way) in the focal plane were made by multiplying the one-way transmit and receive lateral beam functions corresponding to the appropriate center frequencies. For example, the SH20 (two-way) beam function was the superposition of the 20 MHz (one-way) transmit beam and the 10 MHz (one-way) receive beam. The results are summarized in Table II.

TABLE II

| Lateral resolution (μm) | SH20 | FN20 | UH20 | Sec20 | FN30 | SH30 |
|---|---|---|---|---|---|---|
| −6 dB | 241 | 193 | 150 | 120 | 128 | 161 |
| −12 dB | 325 | 264 | 205 | 165 | 176 | 217 |

Transmit Characteristics

A. Transmit Conditions

The transmit conditions employed are of importance to the performance of a nonlinear microbubble imaging system. Transmit amplitudes, controlled in the VS40 by selecting attenuation levels to the output stage of the power amplifier, were varied over 1 order of magnitude. Amplitude values are referred to, from highest to lowest, as 0 dB, −6 dB, −12 dB and −20 dB.

The bandwidths of the pulse lengths employed in this study were measured in pulse-echo mode at the −20 dB transmit amplitude level using a quartz flat located at focus. Transmit gate lengths of 4, 6, and 10 cycles were used, which corresponded to measured −12 dB relative bandwidths of 34%, 27%, and 17% respectively. The transmit filter ensured that the −40 dB bandwidth of transmit frequency energy was between 13.2 MHz and 26.5 MHz for all bandwidths and transmit amplitudes. Linearly scattered energy from tissue did not therefore contribute to nonlinear frequency ranges of interest. Similarly, the transmit filter for the 30 MHz pulse ensured that no detectible energy was passed into the receive bandwidth of the SH30 filter.

B. Hydrophone Measurements

A hydrophone was used to measure the transmitted pressure at the focus for the pulse bandwidths and transmit amplitudes employed in this study. The measurements were conducted in a water tank using a 4 μm thick PVDF membrane hydrophone (Agilent Technologies, Palo Alta, Calif.) with a geometric spot of 25 μm diameter, as described in Cherin et al., (2002) Ultrasound Med. Biol., 28(5): 635-646, which is incorporated herein for the methods taught therein. The received hydrophone signals were digitized at a 250 MHz sampling rate using a PC based 8 bit A/D system (Gage Applied Sciences, Montreal). One hundred traces were averaged at each location. The fundamental and second harmonic ratios were calculated using the ratio of their peaks in the frequency domain.

Figure 18:
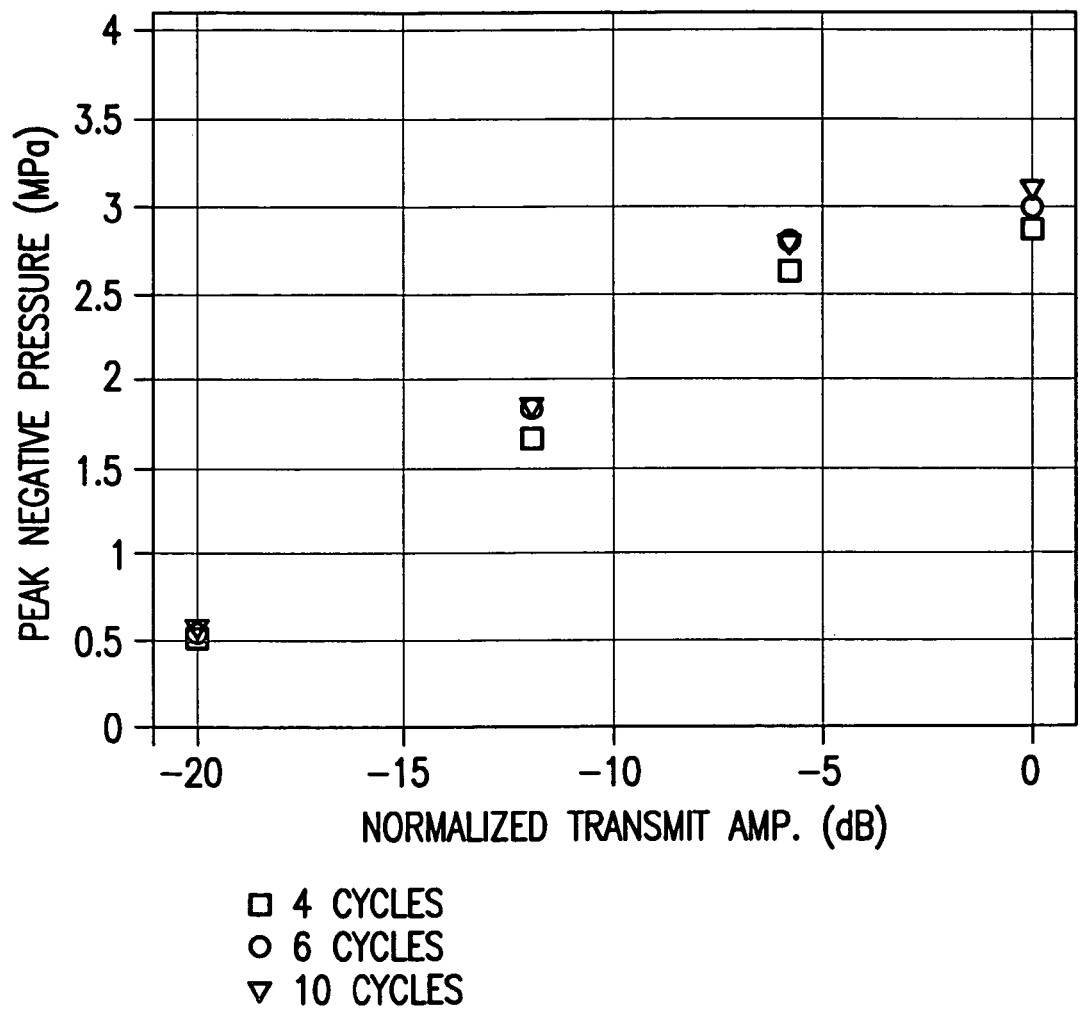
FIG. 18 shows the plot of peak negative pressure versus normalized transmit amplitude, as measured in a water tank by a 25 μm hydrophone located at focus.

FIG. 18 shows the peak negative pressures versus normalized transmit amplitudes for all pulse lengths. The pressure levels and nonlinear propagation are comparable to those reported in. Cherin et al., (2002) Ultrasound Med. Biol., 28(5): 635-646.

Figure 19:
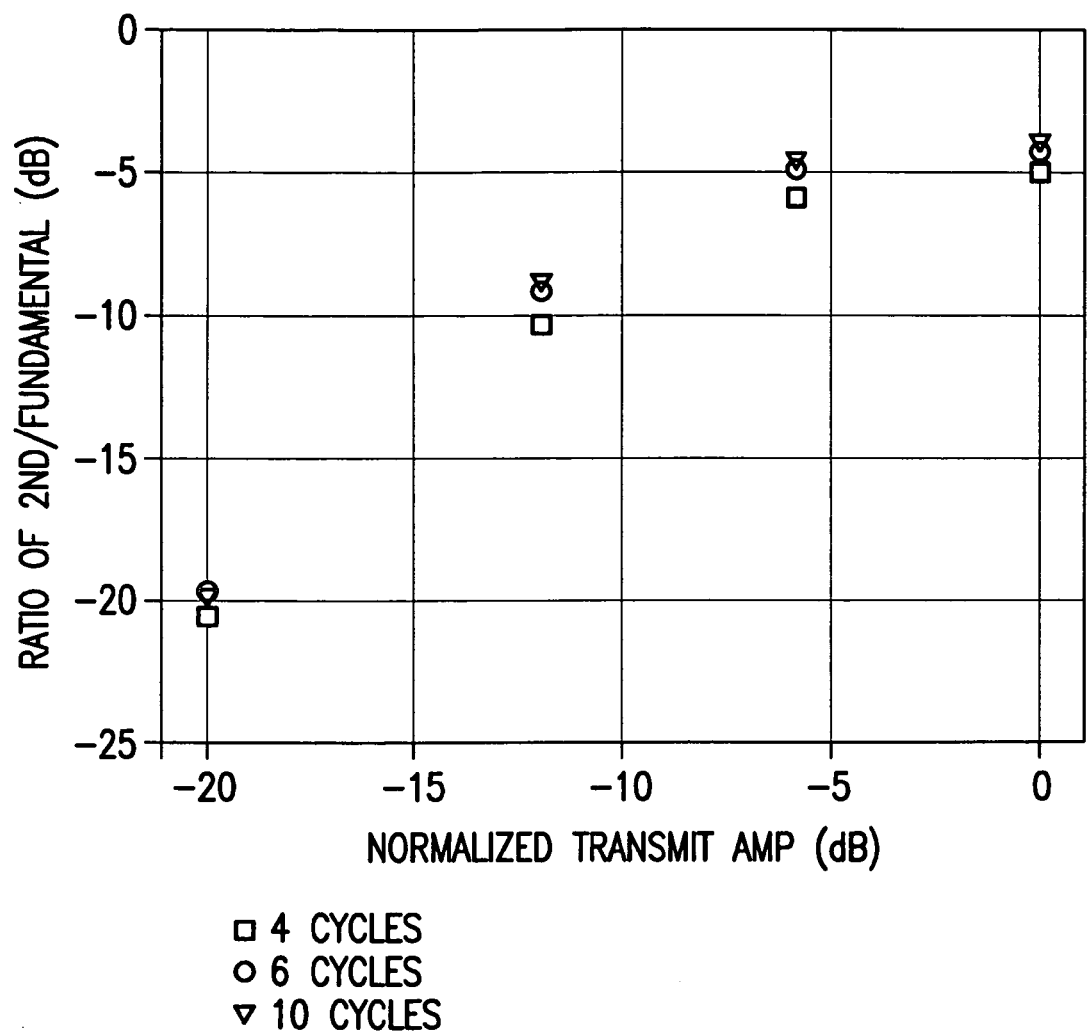
FIG. 19 shows the plot of the ratio of second harmonic over fundamental as a function of transmit amplitude indicates that significant nonlinear propagation occurs under the conditions employed herein. Results are from water tank hydrophone measurements at focus.

FIG. 19 shows a plot of the ratio of the second harmonic to fundamental peak as a function of transmit amplitude. In phantom experiments or in vivo, this ratio is lower than that measured in water due to the high Gol'berg number of water relative to soft tissues. Szabo et al., (1999) Ultrasound Med. Biol. 18: 33-41.

To confirm that the measured second harmonic signal levels were reasonable, nonlinear field simulations (Lee et al., (1995) J. Acoust. Soc. Amer., 97: 906-917) were performed for the transducer geometry and transmit conditions. In particular, the frequency domain amplitude ratios of second harmonic and fundamental frequency signals at the lowest transmit amplitudes at focus were calculated. As a point of reference, the simulations were performed such that the calculated and measured peak negative pressures were matched. The physical properties of water used in these simulations were: acoustic velocity=1500 m/s; density=1000 kg/m3; attenuation=2.221×1$^{-4}$ dB per millimeter per megahertz$^2$; and the coefficient of non-linearity β=3.5. The results predicted a second harmonic to fundamental frequency rations of −18.2, −18.0, and −17.7 dB for the 4, 6, and 10 cycle cases, respectively. The measured values of −20.2, −19.8, and −19.8 dB were slightly lower than the predicted values, which demonstrates that the received second harmonic signals are due to nonlinear propagation rather than transmission artifacts.

Nonlinear Scattering Characteristics

A. Methods

Figure 20:
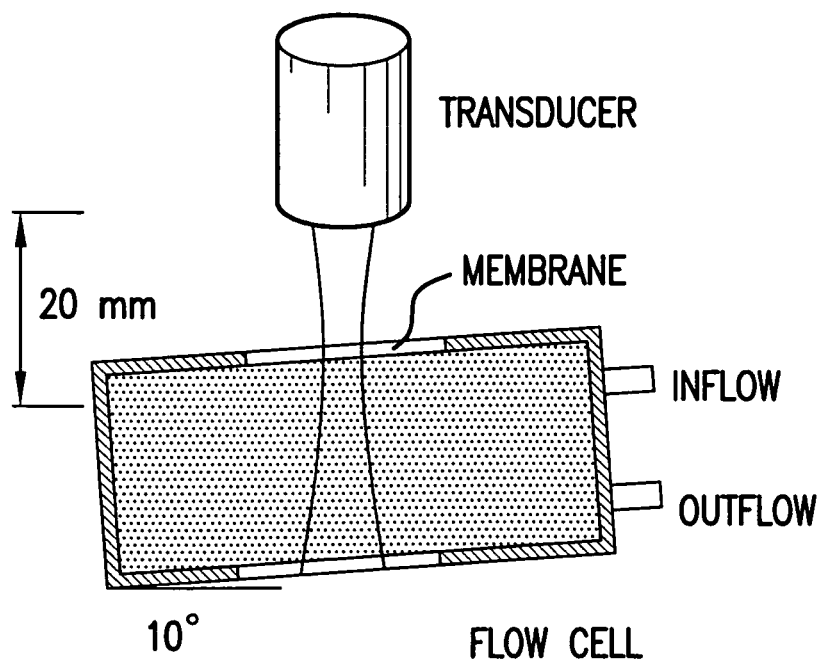
FIG. 20 shows a block diagram overview of the flow cell configuration employed for agent characterization.

Nonlinear scattering from Definity™ was evaluated using a flow cell located in the focal region of the transducer (FIG. 20). Mylar membranes at the front and back of the flow cell provided an acoustic window for the beam. The front membrane was oriented at 80 degrees with respect to the transducer beam axis to minimize membrane reverberation. The geometric focus was located 2 mm behind the membrane. On receive, the signals passed through a 59 dB pre-amplification stage (AU-1341, Miteq, Hauppauge, N.Y.). Signals were then digitized with a Lecroy 520 oscilloscope (Chestnut Ridge, N.Y.) at a sample rate of 500 MHz. A time window of 2 µs in length was analyzed, corresponding to 1.3 mm axial distance centered about the transducer focus.

Immediately prior to the scattering measurements, Definity™ was diluted to a concentration of 0.01% by volume in room temperature saline. The resulting suspension 2008 was placed in a reservoir and mixing was performed gently with a magnetic stirrer. Flow through the cell (inflow and outflow) 2010 was controlled with a gravity feed approach and was sufficiently fast for replacement of agent within the beam to occur between pulses (0.09 seconds). An average of 200 pulses was taken at each setting, and measurements were repeated for 2 different vials of Definity™. Noise spectra were also recorded at each acquisition setting, and these were removed from the received agent spectra. The spectra presented here are not corrected for the frequency response of the transducer on receive, in order to accurately reflect the relative signal strengths in each bandwidth that is available for image formation. For the purposes of display, plots for each pulse length are normalized to the peak of the fundamental frequency at the 0 dB (i.e. maximum) transmit amplitude setting.

B. Results

Figure 21A:
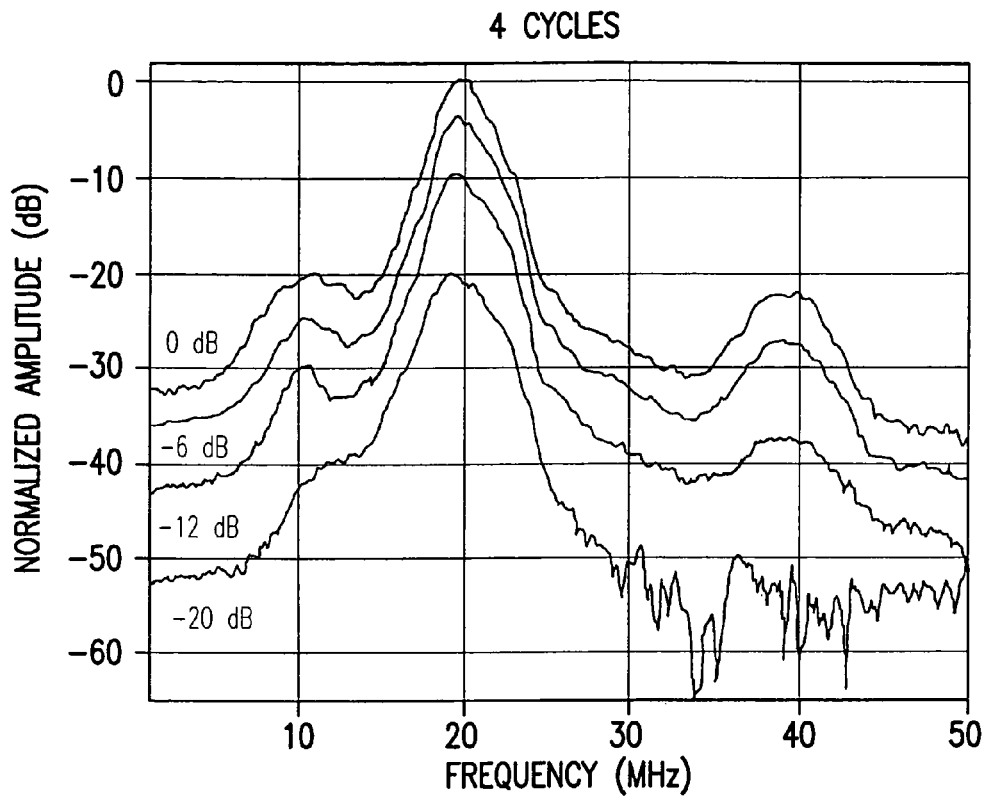
FIGS. 21a, b and c show received spectra from Definity™ within the flow cell under the conditions employed herein. Top (a), middle (b), and bottom (c) plots indicate results for 4, 6, and 10 cycle settings respectively. For each pulse length, the results for different pressures are normalized with respect to the peak signal at the fundamental frequency at the highest transmit amplitude.
Figure 21B:
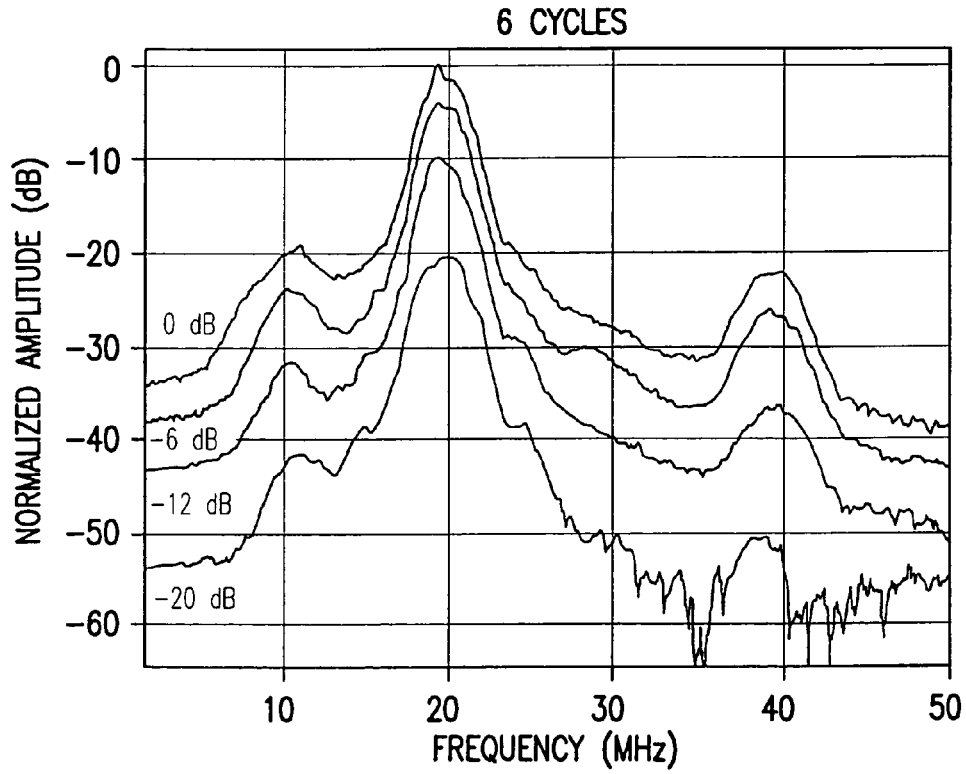
Figure 21C:
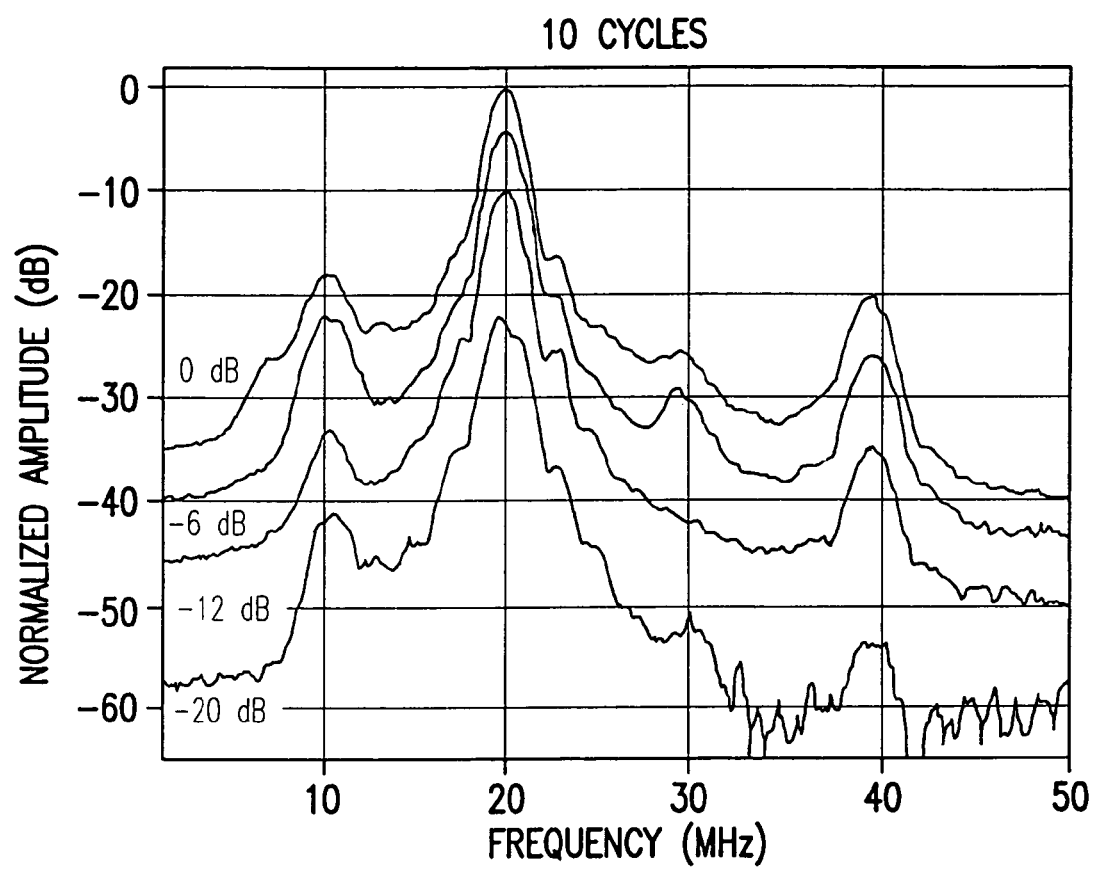
Figure 22A:
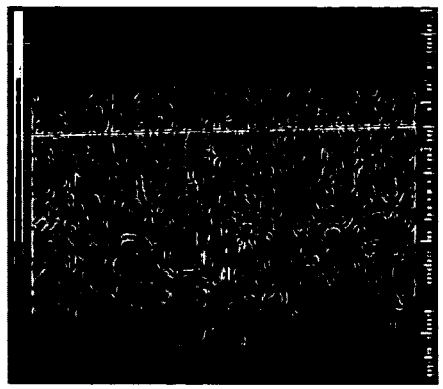
FIGS. 22a, b, c and d show example B-scan images of a 1 mm wall-less vessel phantom in FN20 (a), Sec20 (b), SH20 (c), and UH20 (d) imaging modes. Both FN20 and Sec20 images show poor contrast between the vessel and tissue regions. However, SH20 and UH20 imaging suppresses the tissue signal to below the noise floor. Transmit settings are 6 cycles and −6 dB transmit amplitude. The images are 8 mm square, and the spacing between the large ticks on the vertical scale is 1 mm.
Figure 22B:
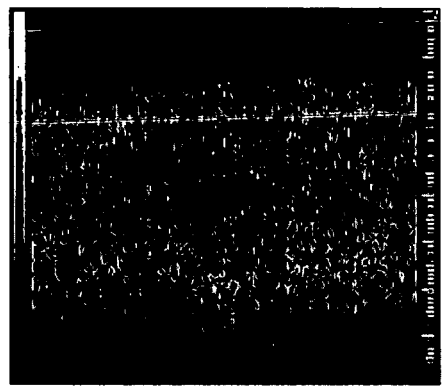
Figure 22C:
Figure 22D:

The received spectra as a function of pressure for transmit pulses of 4, 6, 10 cycles are shown in FIG. 21. Under all conditions a large and distinct SH20 peak can be seen. UH20 energy was also significant, though not generally in the form of a pronounced peak. The relative strengths of these peaks show that SH20 performs better than the UH20 in terms of signal strength. This is in part due to the frequency response of the transducer being more sensitive at the SH20 frequency (10 MHz) than the UH20 frequency (30 MHz). The Sec20 signals are strong but, as can be seen from the hydrophone data (FIG. 19), the second harmonic propagation is substantial. The pressure data represent a single axial location 25 µm in diameter whereas the contrast spectra are derived from a 1.3 mm axial region and across the entire beam width.

These scattering results are qualitatively consistent with those reported in Goertz et al., (2001) Proc. IEEE Ultrason. Symp. In that study, which provided a comparison with linear scatterers of known frequency response, it was found that Sec20 nonlinear scattering was observable but substantially contaminated by the presence of Sec20 propagation harmonic.

These results, demonstrate the generation of substantial subharmonic signals at relatively large bandwidths (17-34%). Investigations of driven free bubbles indicate that subharmonic signal strength builds up over a number of transmit cycles. The convention of referring to scattered energy centered at half the transmit frequency as subharmonic energy was adopted.

In this study the presence of subharmonic energy for transmit levels as low as 500 kPa was observed.

FIG. 21 also indicates strong Sec20 signals but, as can be seen from the hydrophone data (FIG. 19), the second harmonic propagation was substantial.

Phantom Experiments

A. Methods

Phantom experiments were conducted at a transmit frequency of 20 MHz in order to evaluate the qualitative and quantitative performance of the system in SH20, UH20, and Sec20 imaging modes. SH30 imaging is also demonstrated for a transmit frequency of 30 MHz.

Phantoms were comprised of 83% (by weight) water, 15% gelatin, and 2% amorphous silica particles (S-5631, Sigma Chemical Co., St. Louis, Mo.) as scatterers. The acoustic properties of this phantom material at high frequencies has been described previously. Ryan and Foster, (1997) Ultrasound in Medicine & Biology 23: 261-273. A wall-less vessel was created by 1 mm outer diameter wire located within a chamber when the phantom material was cast. The wire was then extracted, leaving two 18-gauge needle adaptors providing an inlet and outlet to a 1 mm diameter wall-less vessel. The vessel was located at a depth of ~3-4 mm below the surface of the phantom. Agent was passed through the vessel using a gravity feed approach at a mean velocity of ~30 mm/s, as calculated using the outflow. Agent was diluted to a concentration of 0.01% by volume in saline immediately prior to the experiments. This concentration resulted in a vessel echogenicity level comparable level to that of the surrounding tissue. Experiments were conducted within 5-20 minutes of agent dilution, which corresponds to a period of stable acoustic properties at high frequencies with Definity™. Goertz, (2002) PhD Thesis, University of Toronto, 2002. The lateral scan distance was 8 mm, and the frame rate was 1.9 Hz. All images were acquired and displayed at this frame rate. At 512 lines per image, this corresponded to approximately a 1 KHz pulse repetition frequency (PRF).

Experiments were conducted in SH20, FN20, UH20 and Sec20 modes, as well as SH30 and FN30 modes. The transducer beam was oriented at an angle of 70 degrees with respect to the vessel long axis and the scan plane imaged the vessel in cross-section. A water bath was used to couple the transducer with the phantom. The experiments were conducted as a function of transmit amplitude and bandwidth. For each transmit condition, 16 image frames were recorded using 2 bottles of agent. Quantification of the B-scan images was accomplished in the following manner. A conversion from logarithmically compressed data to linear power data was performed using a calibration table derived from measurements. Within each linear power image, three regions of interest (ROI) are selected. Contrast ('vessel') signals were derived from the average power within a 0.5 mm by 0.5 mm region located within the vessel. Tissue signals were measured from a 2 mm wide by 0.5 mm deep region at the same depth as the vessel. The noise signal was recorded from a location within the water coupling region preceding the phantom where no echoes were present. The mean and standard error of the average power within these regions was then calculated at each setting. When a tissue signal was present the contrast to tissue ratio (CTR) was calculated. When the tissue signal was suppressed to below the noise floor, the contrast to noise ratio (CNR) was calculated as the ratio of the average power in the vessel ROI to the average power in the noise ROI.

These results were then plotted against mechanical index, using the water tank hydrophone pressure data (FIG. 18). The mechanical index was calculated as the peak negative pressure divided by the square root of the transmit frequency measured in MHz.

Axial and lateral vessel sizes were measured in each imaging mode. The mean and standard error were calculated using 16 image frames. For the subharmonic and ultraharmonic cases, the vessel dimensions corresponded to the point at which the vessel dimensions corresponded to the point at which the vessel image rose above the electronic noise floor. For the fundamental and second harmonic cases, the vessel dimensions were made visible due to differences in the lateral correlation pattern of flowing agent as compared to tissue.

B. Results

The ability to form images using the linear FN20, and the three nonlinear frequency regions of SH20, UH20, and Sec20 is demonstrated in FIG. 22. These results are for a 6-cycle pulse and transmit amplitude of −6 dB. By selection of the Definity™ concentration, the FN20 image shows similar signals level in the vessel and tissue regions. Both the SH20 and UH20 images demonstrate suppression of tissues signal to below the noise floor. This latter point is due to the use of nonoverlapping transmit and receive analog filter bandwidths. The presence of significant contrast signal compared to the noise floor in both the subharmonic and ultraharmonic frequency regions is due to the nonlinear scattering demonstrated in FIG. 21. In the Sec20 image the tissue signal has not been suppressed, and shows qualitatively little difference in CTR as compared to FN20 mode.

Note also that the character of the speckle is different in the vessel region as compared to the surrounding tissue. This is primarily due to the speed of microbubbles within the vessel being significant relative to the transducer scan speed, which reduces the lateral correlation length of speckle within the vessel. This is also observed with linear scatters.

An examination of FIG. 22 also reveals differences in the vessel size appearance between imaging modes. The axial and lateral dimensions, as measured in each imaging mode under the conditions shown in FIG. 22, are summarized in Table III.

dependent nature of the received signals. If an onset pressure threshold is present, this has the effect of limiting the lateral width of the transmit beam. Furthermore, the form of the increase in signal strength as a function of pressure also changes the lateral distribution of received signal strengths for a point scatterer, which in turn affects the lateral point-spread function. For the Sec20 case, the measured vessel size is smaller than would be expected when considering the theoretical effective beamwidth (Table II). However, this estimate does not take into account the narrowing of the transmit beam due to nonlinear propagation. Additionally, the poor CTR and SNR in second harmonic mode can lead to a lower estimate of the measured vessel width than for the other imaging modes.

Figure 23A:
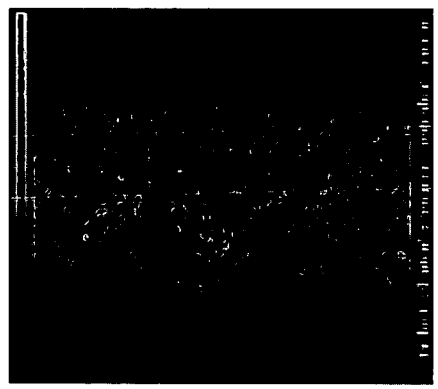
FIGS. 23a and b show example B-scan images of a 1 mm wall-less vessel phantom in FN30 (a) and SH30 (b) imaging modes. Again the use of subharmonic imaging has resulted in the suppression of tissue signal to below the noise floor. The images are 8 mm square, and the spacing between the large ticks on the vertical scale is 1 mm.
Figure 23B:
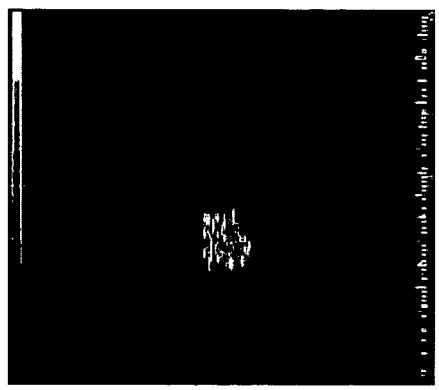
Figure 24A:
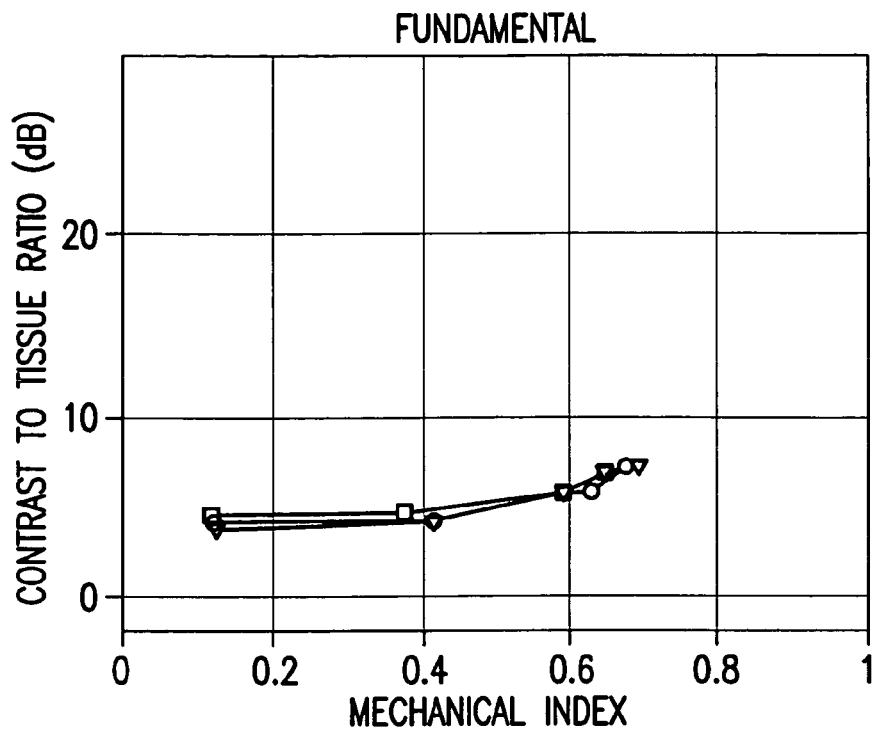
FIGS. 24a, b, c and d show quantitative analysis of the performance of linear and nonlinear imaging modes as a function of transmit pulse length (□-4 cycles; o-6 cycles; ∇-10 cycles) and transmit amplitude. Contrast to tissue ratios for F20 (a) is modest, by choice of the agent concentration, and increases slightly with MI. Sec20 (b) imaging has similar, but slightly lower levels of CTR as compared to F20. Both SH20 (c) and UH20 (d) have suppressed the tissue signal and have substantial CNR that increase with MI.
Figure 24B:
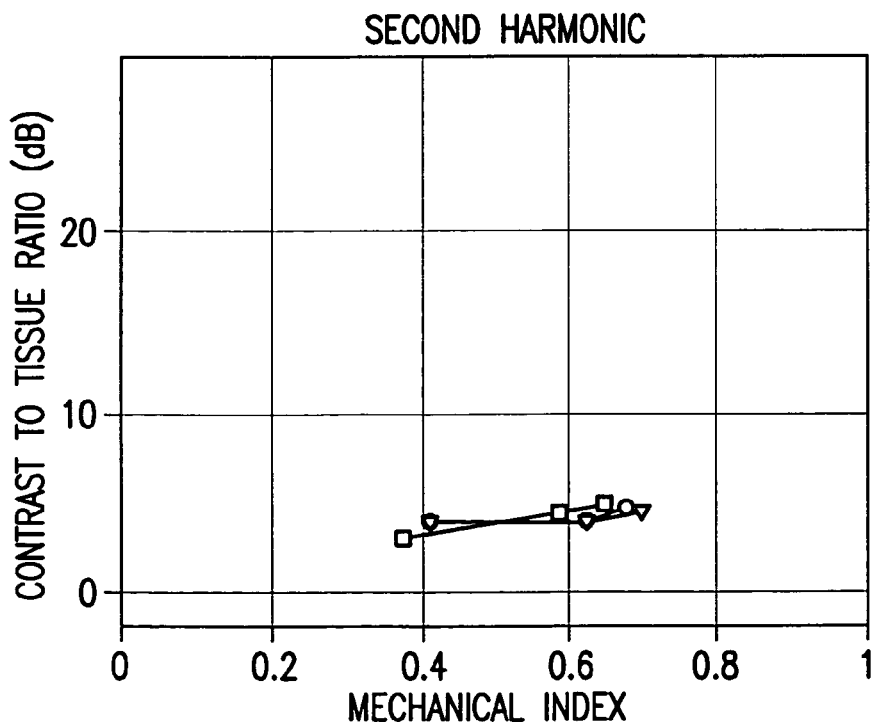
Figure 24C:
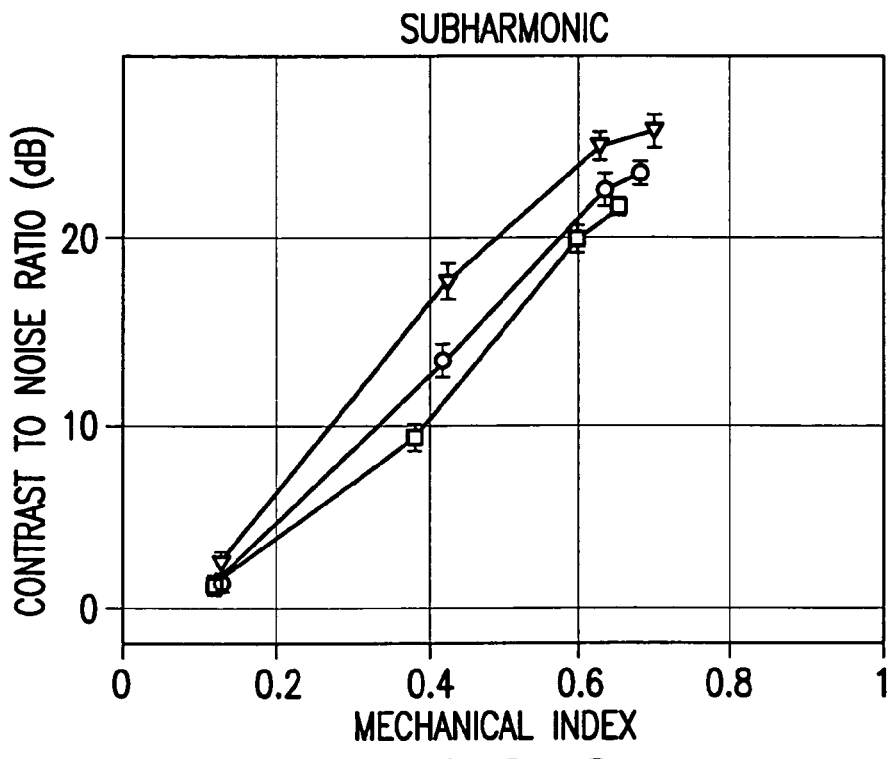
Figure 24D:
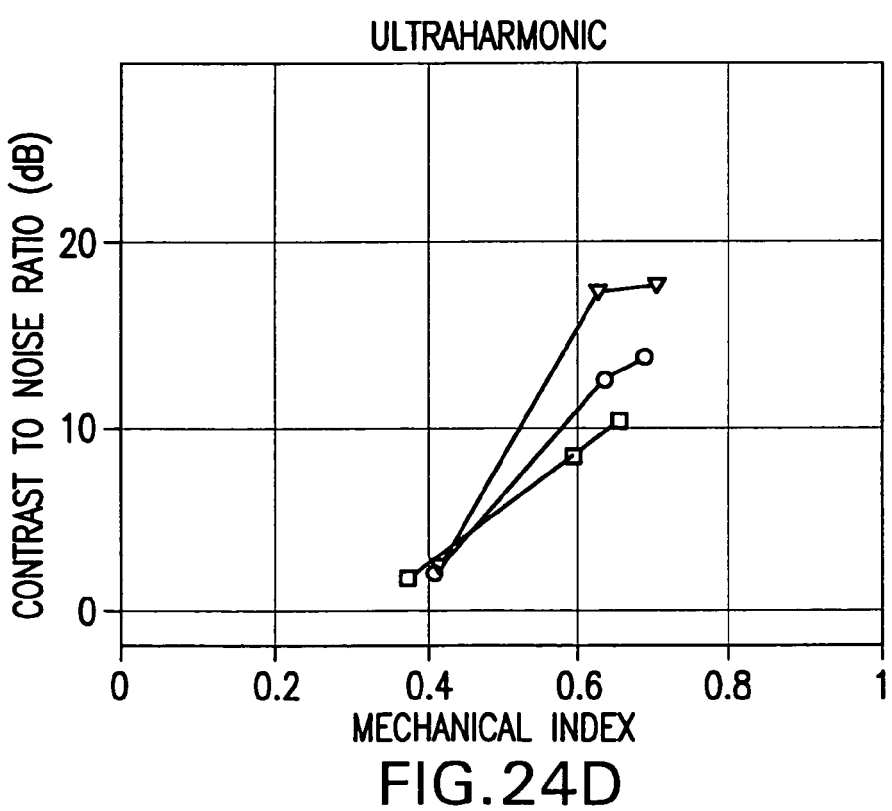

FIG. 23 shows an example result for a transmit frequency of 30 MHz (six cycles). As with SH20 imaging mode, the UH20 mode also demonstrates the suppression of tissue signal to below the noise floor. The 20 MHz transmit case in a quantitative manner using SH20, UH20, and Sec20 signals were concentrated on, but, the results shown in FIG. 23 demonstrate that the potential exists to extend SH imaging to substantially higher transmit frequencies.

A quantative analysis of the CTR and CNR was performed as a function of pulse length and MI for a transmit frequency of 20 MHz (FIG. 24). In FN20 mode, the CTR rises from 4 dB to 7 dB with increasing MI. For both the SH20 and UH20 modes, the CNR is substantial and increases with pulse length and MI. At the highest MI, SH20 and UH20 have CNRs of 26 dB and 17 dB, respectively. Even at the lowest transmit amplitude, subharmonic and ultraharmonic signals are present. Therefore, these data indicate that SH20 and UH20 imaging modes are both perform well in suppressing tissue signals.

The vessel appears largest for SH20 mode, and is progressively smaller for the FN20, UH20, and Sec20 modes. In the lateral direction, this is attributed to receive beam width differences arising from the different center frequencies. In the axial direction, both differences in the receive filters as well as nonlinear bubble responses can result in differences in resolution. Note also that the character of the speckle is different in the vessel region as compared to the surrounding tissue.

TABLE III

| Measured Size (mm) | SH20 | FN20 | UH20 | Sec20 |
| --- | --- | --- | --- | --- |
| Axial | 1.335 ± 0.016 | 1.076 ± 0.015 | 1.178 ± 0.01 | 1.010 ± 0.002 |
| Lateral | 1.34 ± 0.02 | 1.188 ± 0.03 | 1.146 ± 0.014 | 1.023 ± 0.008 |

In the axial direction, the vessel size appears largest in SH20 mode, and progressively smaller for the FN20, UH20, and Sec20 modes, respectively. At least two factors contribute to this. First, as summarized in Table I, the receive bandwidths differ between imaging modes, which can result in differences in axial resolution. Second, nonlinear bubble behavior may potentially lead to differences in emitted pulse lengths between each imaging mode.

In the lateral direction, the vessel also appears larges in the SH20 made and is progressively smaller for the FN20, UH20, and Sec20 modes, respectively. As illustrated in Table II, an important factor contributing to this are differences in transmit and receive frequencies leading to differences in the transmit and receive beamwidths. The increase in lateral vessel dimension would be expected to correspond to the effective lateral resolution of the transducer. Indeed, for the SH20, FN20, and UH20, the difference between the actual and measured vessel sizes was within the range of theoretical −6 to −12 dB effective beamwidths. In SH20 and UH20 modes, another factor affecting the lateral resolution is the pressure This is primarily due to the speed of microbubbles within the vessel being significant relative to the transducer scan speed, which reduces the lateral correlation length of speckle within the vessel. This is also observed with linear scatterers. Goertz et al., (2003) Ultra sound Med. Biol., 29: 39-51.

These data therefore indicate that SH20 and UH20 imaging modes perform well in suppressing tissue signals.

In Vivo Experiments

A. Methods

Experiments were conducted using a mouse heart and rabbit ear. In the mouse heart, agent located within the left ventricle was specifically visualized. The mice were anesthetized using isoflurane. Definity™ was diluted to 25% by volume in saline, and a bolus of 0.02 ml was injected through a 24-gauge catheter located within a tail vein. Images were acquired within 3 minutes after injection. Nonlinear experiments were performed in SH20 imaging mode using a 6-cycle pulse at −6 dB transmit amplitude. Linear imaging was performed in VS40 B-scan mode with a broadband pulse centered at 19 MHz.

The rabbit ear is a useful model with which to examine the microvasculature. A range of vessel calibers are readily visible and the ear can be stabilized to avoid tissue motion artifacts. The rabbit was anesthetized with isoflurane during the experiments. Agent was administered through a contralateral ear vein by means of an intravenous drip, with the agent diluted to a concentration of 2% by volume in physiologic saline. Linear imaging was performed in normal VS40 B-scan imaging mode using a broadband 19 MHz centered pulse. Nonlinear imaging experiments were performed in SH20 mode using 6 cycles and a ~6 dB transmit amplitude. All animal experiments were conducted in accordance with protocols approved by the Sunnybrook and Women's College Health Sciences Centre Institutional Animal Care and Use Committee.

B. Results

Figure 25A:
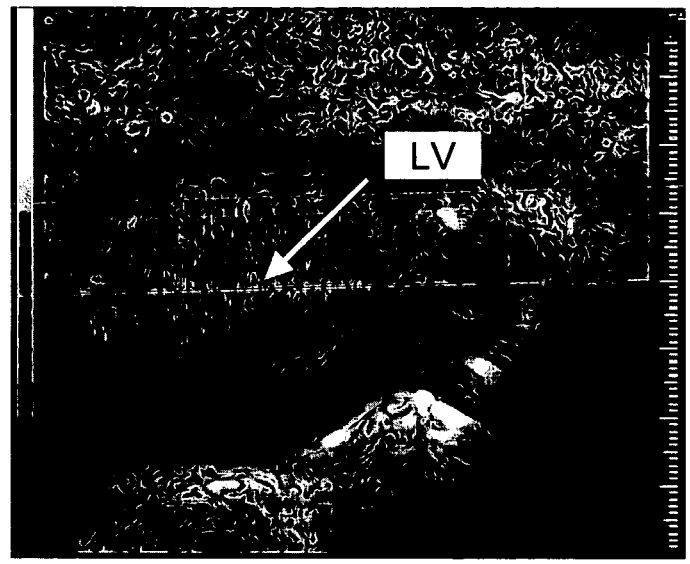
FIGS. 25a and b show In vivo demonstration of nonlinear B-scan imaging in the mouse heart. a) Short axis view of a left ventricle (LV) of a mouse heart in fundamental at 20 MHz. b) a SH20 image clearly shows the suppression of the tissue signal, leaving a view of agent located within the left ventricle.
Figure 25B:
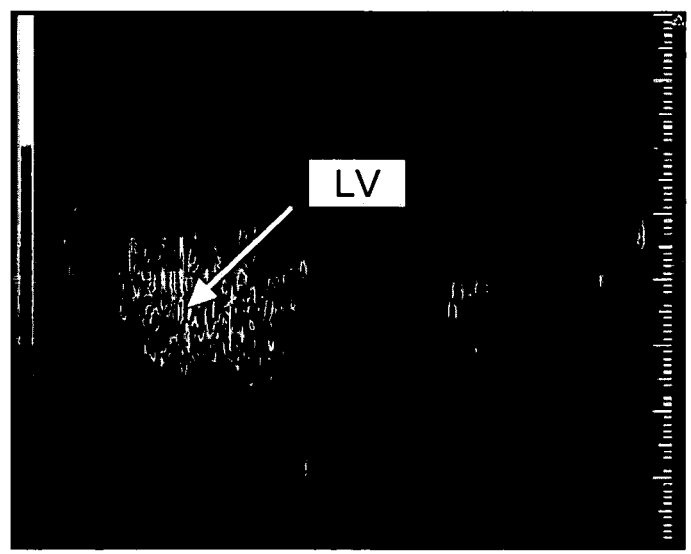

FIG. 25a shows a short axis view of the left ventricle of a mouse heart in linear B-scan imaging mode. FIG. 25b shows a SH20 image of the same view following a tail vein bolus injection of Definity™. SH20 mode can be seen to suppress the tissue signal, and leaves a clear view of agent located within the left ventricle. Other isolated bright spots are also evident that may be associated with agent located in nearby vasculature. These spots were not present prior to the injection of agent. In addition to providing a useful in vivo validation, these results demonstrate that nonlinear contrast imaging is useful in high frequency small animal imaging, which is a rapidly growing application for ultrasound biomicroscopy. Foster et al., (2000) Ultrasound Med. Biol. 26:1-27.

Agents became detectable in the nonlinear images within several seconds after venous injection, which is reasonable when it is considered that the average circulation time for blood in adult mice is approximately 7 seconds. As with conventional frequency contrast, the implementation and investigation of techniques to examine the time course of agent inflow into regions of interest can provide important physiological information. The use of nonlinear agent-detection strategies, such as those demonstrated herein, can enhance the performance of such techniques.

Figure 26A:
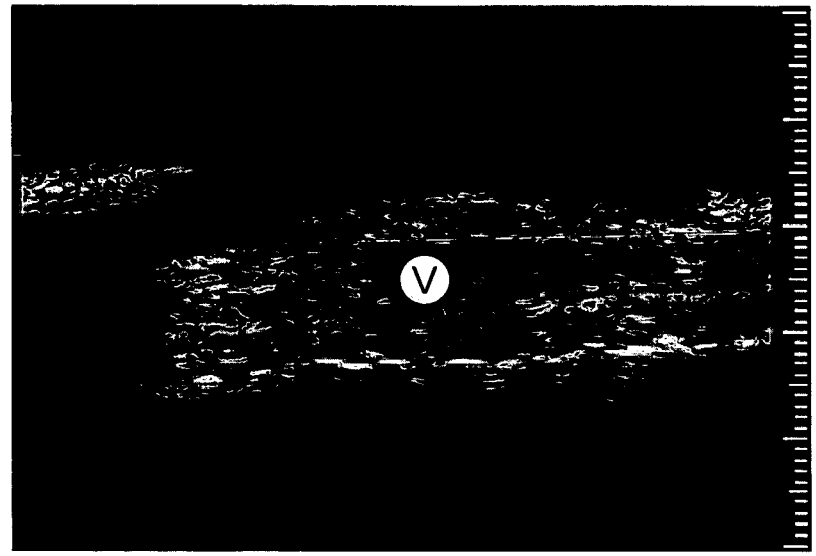
FIGS. 26a and b show In vivo demonstration of nonlinear B-scan imaging in the microvasculature of a rabbit ear. a) 20 MHz B-scan fundamental mode image of a rabbit ear in cross section, where the presence of a 300-400 μm diameter microvessel ('V') is evident by its hypoechogenecity relative to the surrounding tissue prior to the injection of contrast. b) SH20 inset image of this same region after the introduction of contrast. The tissue has been suppressed, leaving an image of the 400 μm vessel as well as signals from several smaller vessels that were not visible in the original scan.
Figure 26B:
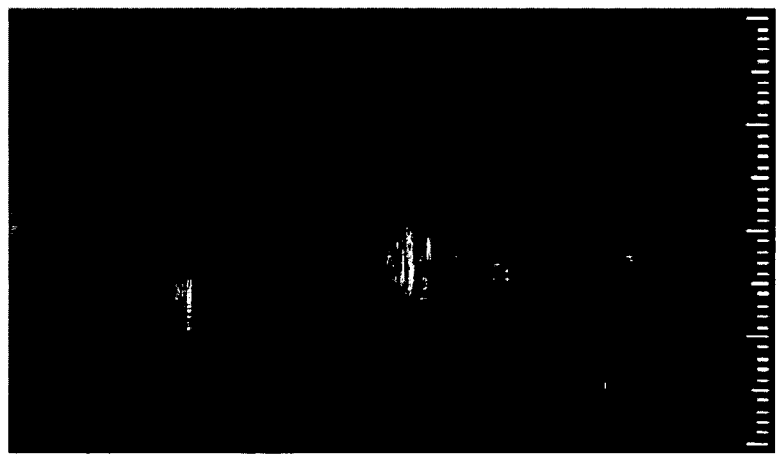

FIG. 26 shows a 20 MHz fundamental mode image of the cross section of a rabbit ear which includes a visible vessel of ~300-400 µm in diameter. Following a bolus injection of agent, SH20 imaging clearly detects agent in this vessel as well as other previously unresolved microvessels while suppressing the tissue signal to below the noise floor.

Example 2

A High Frequency Nonlinear Color Flow Imaging System

Figure 27:
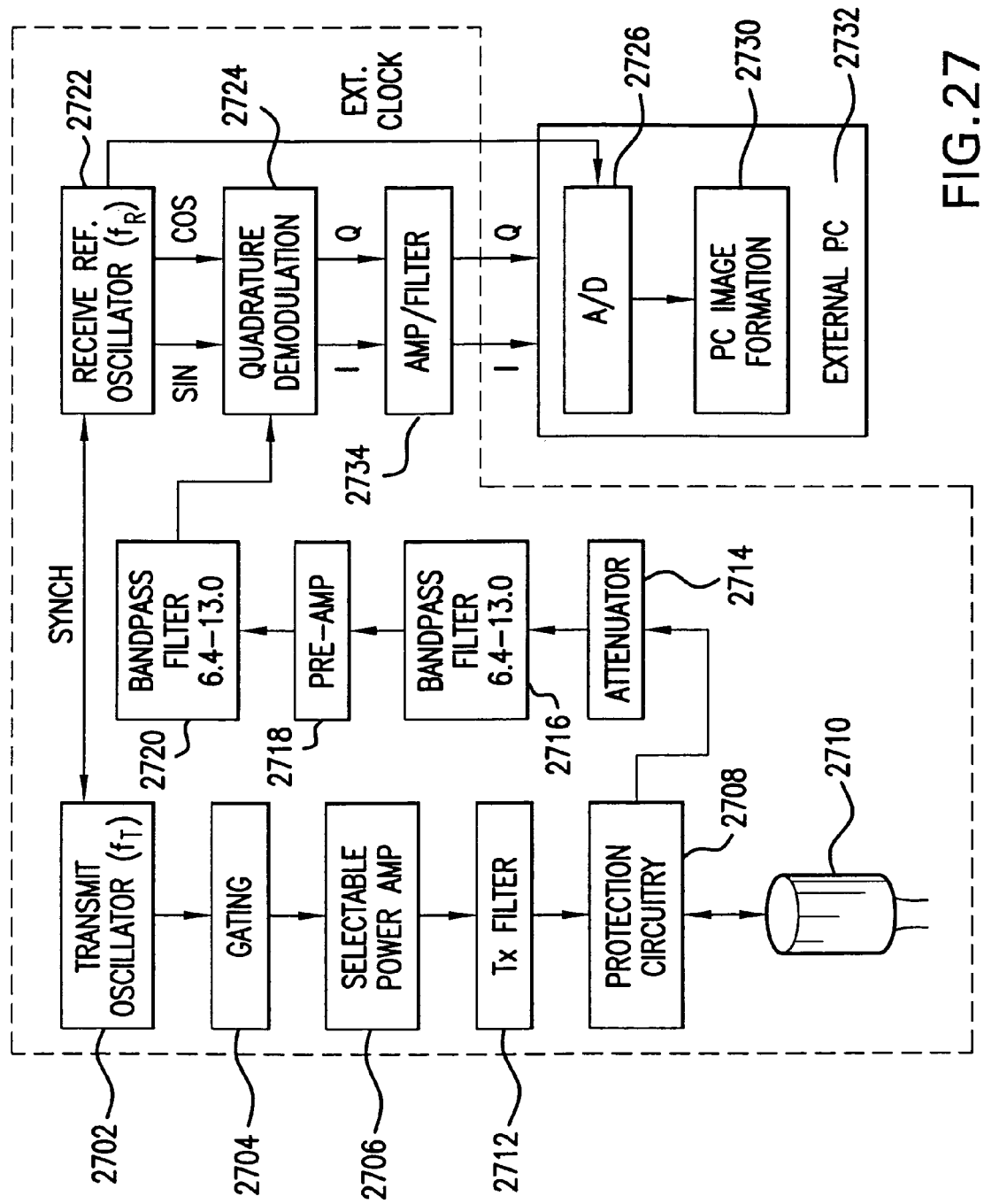
FIG. 27 shows a block diagram overview of an exemplary nonlinear color flow imaging system, where components specifically related to nonlinear imaging are highlighted. The dashed box indicates components related to the VS40 PLUS VEVO 660 system. The received nonlinear signals are isolated with analog filtering, undergo coherent quadrature analog demodulation, and are then acquired on a separate PC based acquisition system. Note that −20 dB bandpass cut-off frequencies are specified.

The system design was based on a previously reported combined pulsed-wave Doppler (PWD)/high frequency flow imaging system (Deng et al., (1998) Ultrasound Med. Biol. 24: 383-394), which was modified for use with nonlinear signals. The system was implemented using a Visualsonics (model VS40, Visualsonics Inc., Toronto) B-scan/PWD instrument (Foster et al., (2002) Ultrasound Med. Biol. 1165-1172) in combination with a separate PC based data acquisition card and flow processing. Alternatively a Vevo 660, or another system, could be utilized. A mechanically scanned single element transducer was used and images were constructed from a consecutive series of pulse-echo lines obtained during linear translation. A block diagram overview is shown in FIG. 27, where design modifications to enable nonlinear imaging capabilities are highlighted.

A. Transmit Sub-System

The transmit component of the system is described herein. Both the oscillator frequency and gate length were selectable using a transmit oscillator 2702 and a gating element 2704, thereby giving substantial control over the center frequency and pulse bandwidth. The resulting low amplitude pulse was then amplified using a selectable power amplifier 2706 to a level appropriate for ultrasound pulse generation. In the original VS40 configuration, this pulse passed directly into protection circuitry 2708 consisting of an expander and a limiter/pre-amplifier combination. After the received signal exited the limiter/pre-amplifier it entered the receive sub-system, which is discussed in more detail in the following section.

To ensure that the transmit and receive frequency bands do not overlap a high power bandpass filter 2712 to remove frequency domain side-lobes that would leak into the receive filter bandwidths. For the 20 MHz centered transmit pulse used in this study, an $8^{th}$ order band pass filter was used with −3 dB points at 16.7 MHz and 24.9 MHz, and −20 dB points at 15.2 MHz and 25.5 MHz.

A spherically focused polymer transducer 2710 (8 mm aperture, 20 mm focal length) was employed. At 20 MHz, the theoretical −3 dB depth of field was 8.2 mm and beam width was 0.187 mm. The transducer has center frequency of 19 MHz and −12 dB points at 5 MHz and 32 MHz. The sensitivity of the transducer at the subharmonic center frequency (10 MHz) relative to its peak sensitivity at 19 MHz, is −4 dB.

B. Receive Sub-System

The receive side of the original VS40 system is split into two sub-systems: one for B-scan imaging and one for PWD. The B-scan imaging sub-system (not shown) employs analog logarithmic compression circuitry, which in this study is used to form linear B-scan images prior to conducting color flow imaging experiments. To enable color flow imaging mode, RF signals exiting the protection circuitry undergo analog coherent quadrature demodulation 2724 using components of the VS40 PWD sub-system. In linear flow imaging mode (Deng et al., (1998) Ultrasound Med. Biol. 24: 383-394), the transmit oscillator signal was used as a reference demodulation source. The resulting in-phase and quadrature baseband signals were then split into two paths: one for PWD and the second for color flow imaging. In the PWD path (not shown), the signals enter audio frequency circuitry where they were sampled at a specific depth to generate a PWD spectrum. An amplifier/filter 2734 can condition the signal between quadrature demodulation and the A/D system. In the flow imaging path, the baseband signals were acquired using a two channel 12-bit A/D system 2726 (PDA12, Signatec, Corona, Calif.) located in a separate PC 2732. To ensure that trace-to-trace acquisition jitter was not significant, the A/D board was operated in external clock mode using the master oscillator output as a source. Triggers were provided by timing circuitry within the PWD sub-system of the VS40. Data for a 2D image plane were acquired as pulses were continuously sent and received at the PRF while the transducer was scanned in a linear manner over the region of interest. The resulting data then undergo processing to extract color flow information.

Figure 28C:
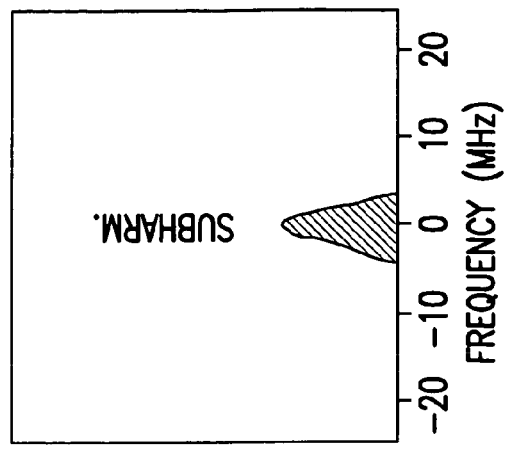
FIGS. 28a, b and c show a schematic overview of nonlinear signal conditioning approach. Received signals from exiting protection circuitry (a) contain subharmonic, fundamental, ultraharmonic and second harmonic energy. These are bandpass filtered to extract the subharmonic (b), which is then quadrature demodulated to obtain baseband signals (c).
Figure 28B:
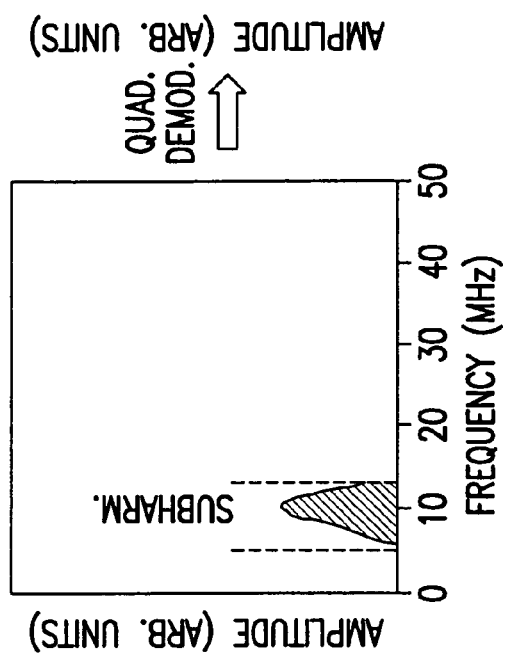
Figure 28A:
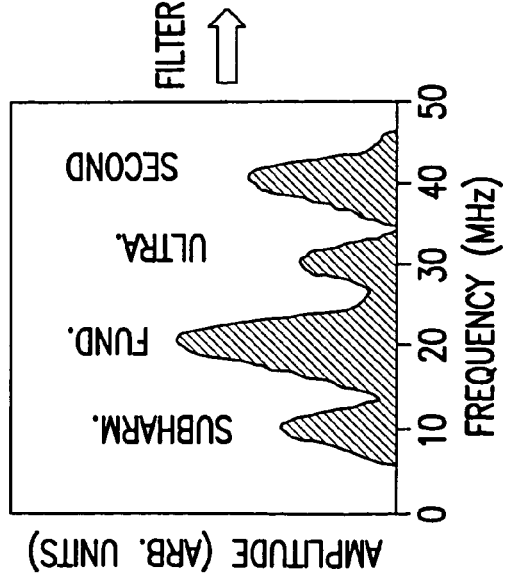

For nonlinear color flow imaging, two modifications were made to the above approach: the addition of an analog RF signal conditioning stage, and the use of a separate receive demodulator. The instrumentation modifications are highlighted in FIG. 27 and their effect on the signals is illustrated in FIG. 28. In the signal conditioning stage the nonlinear signals are isolated using a series configuration of an attenuator 2714, filter 2716, pre-amplifier 2718, and a second filter

2720. The pre-amplifier (44 dB model AU-1313, Miteq, Hauppauge, N.Y.) provided the additional signal gain to detect the nonlinear signals. Two filters 2716 and 2720 were used for the efficient removal of linear signals, as well as the rejection of wideband amplifier noise outside the frequency range of interest. The subharmonic of a 20 MHz transmit signal was evaluated, and the filters used for this were two $8^{th}$ order bandpass with −20 dB cut-off values at 6.4 and 13.0 MHz. As described herein, other nonlinear frequency regions may also be assessed with this instrumentation by the appropriate selection of receive filter characteristics.

The use of a separate receive oscillator 2722 made it possible to selectively demodulate the nonlinear signals of interest, thereby producing analog quadrature baseband signals for that frequency range. This was accomplished by setting the receive oscillator frequency to be equal to the center of the nonlinear frequency band of interest. The transmit oscillator was set to 20 MHz, and the receive oscillator to 10 MHz, corresponding to the center frequency of subharmonic energy.

This system design approach, which integrates PWD and color flow functionality, also enables nonlinear PWD in addition to color flow imaging.

C. Signal Processing

Data for a single frame were acquired by scanning the transducer in a linear manner at constant velocity over a region of interest using the VS40 scanning software. For linear fundamental mode imaging a clutter filter is first applied across the entire data set, followed by partitioning the data into ensembles centered about a series of transducer locations (Deng et al., (1998) Ultrasound Med. Biol. 24: 383-394). In subharmonic imaging mode this is not used, since all tissue signals were suppressed to below the noise floor. Velocity and Doppler power estimates were then performed on these ensembles using the 2D autocorrelator (Loupas (1995) IEEE Trans. Ultrason., Ferroelec., Freq. Contr. 42: 672-688), (Loupas (1995) IEEE Trans. Ultrason., Ferroelec., Freq. Contr. 42: 689-699). Unlike a 1D autocorrelator, which assumes a center frequency for the received signal, the 2D autocorrelator explicitly estimates the receive signal center frequency and accounts for this in the velocity estimate. This may be important if the nonlinear signals of interest deviate significantly from their assumed center frequency (the demodulation frequency), or have substantial stochastic variation about that center frequency.

The use of second harmonic scattering for velocity estimation has been discussed previously (Hope-Simpson et al., (1999) Ultrason. Ferroele, Freq. Contr 46: 372-382), including the implications of applying coherent Doppler estimators to data sets derived from coherent analog demodulation approaches. Verbeek et al., (1998) IEEE T. Bio-med. Eng. 45(10): 1217-1226. While the use of subharmonic signals for image formation has been reported previously (Forsberg et al., (2000) Ultrasonics 38: 93-98), the use of subharmonic signals for velocity estimation has not been reported.

In a conventional flow imaging system, this estimator is applied to clutter filtered data and its output therefore related to the amount of blood with a velocity (along the transducer beam axis) above the clutter filter cut-off frequency. Without applying a clutter filter, this parameter is not directly constrained by a minimum blood velocity determined by the clutter filter passband.

In the final stage of image formation, the decision to display a color pixel is based solely on setting a threshold level of the Doppler power. No additional image processing is performed, in order to have a direct indication of the velocity and power estimator outputs for the purposes of analysis.

D. Transmit Conditions

The results were obtained using a 27% (−12 dB) bandwidth 20 MHz centered pulse. The transmit amplitude corresponded to the −6 dB of the maximum transmit setting of the VS40, which was measured by hydrophone to have a peak negative pressure of 2.6 MPa (mechanical index=0.68) at focus in a water bath. As found in agent characterization experiments described herein, these conditions produce a pronounced subharmonic signal from Definity™.

Phantom Experiments

A. Methods

Validation experiments were conducted using a wall-less vessel phantom. Phantoms were comprised of 83% (by weight) water, 15% gelatin, and 2% amorphous silica particles (S-5631, Sigma Chemical Co. St. Louis Mo.) as scatterers. The acoustic properties of this phantom material at high frequencies has been described previously. Ryan and Foster (1997) Ultrasound in Medicine & Biology 23(2): 261-273. A wall-less vessel was created by a 1 mm outer diameter wire located within a chamber when the phantom material was cast. The wire was then extracted, leaving two 18-gauge needle adaptors providing an inlet and outlet to a 1 mm diameter wall-less vessel. The vessel was located at a depth of ~3-4 mm below the surface of the phantom. Agent was passed through the vessel using a gravity feed approach and mean velocities were calculated using the outflow. Agent (Definity™) was diluted to a concentration of 0.01% by volume in saline immediately prior to the experiments.

The transducer scan speed was 1 mm/s and the PRF was 5 KHz. Ensemble lengths of 50 pulses were used to perform velocity and power estimates, and image lines were calculated every 40 μm. The transducer axis was oriented at an angle of 70 degrees with respect to the vessel axis. This known angle was corrected for in the processed results, which therefore indicate the estimated velocity along the long axis of the vessel. Mean velocities through the vessel were estimated by Doppler power-weighting each velocity pixel. For the purposes of comparison, mean flow velocities within the vessel were also measured using the vessel outflow combined with the vessel diameter as measured with 40 MHz linear B-scan ultrasound. Mean flow velocities in 10-20 mm/s range were used.

B. Results

FIG. 29*a* shows a phantom image in fundamental VS40 B-scan imaging mode, where contrast agent is visible within the vessel region. FIG. 29*b* shows an enlarged view of the target region. The signal intensity level is slightly higher within the vessel lumen and has vertically striated speckle appearance due to signal decorrelation arising from flow speeds that are significant in comparison to the transducer scan speed. Illustrative subharmonic power Doppler and velocity images derived from this phantom at a transmit amplitude of −6 dB are shown in FIGS. 29*c* and d respectively. The power Doppler image has an appearance similar to that of the nonlinear B-scan images as described herein, with the signals from the tissue region of the phantom having been suppressed to below the noise floor. The velocity image exhibits a unidirectional velocity pattern, consistent with what is expected within the vessel phantom. A repetitive measurement of the velocity under these transmit conditions found the Doppler estimated mean velocity within the vessel to be 18.8±1.1 mm/s, which compared well with the velocity of 18.1 mm/s measured using the outflow. The phantom experiments therefore indicate that both power Doppler and velocity estimation can be performed using subharmonic emissions stimulated at a 20 MHz transmit frequency.

In Vivo Experiments

A. Methods

In vivo experiments were conducted using microvessels located within a rabbit ear. Images were acquired with a 1 mm/s scan speed and at a PRF of 5 kHz. Ensemble lengths of 50 pulses were used to perform velocity and power estimates. Prior to conducting the color flow experiments, the ear was imaged in linear B-scan mode, and the velocity of flow within the vessels was assessed using 20 MHz linear PWD. A 15-cycle pulse was used at a PRF of 5 kHz, and these data were collected prior to the injection of contrast.

The rabbit was anesthetized with isoflurane during the experiments. Agent was administered through a contra-lateral ear vein by means of an intravenous drip, with the agent diluted to a concentration of 2% by volume in physiologic saline. Linear imaging was performed in normal VS40 B-scan imaging mode using a broadband 19 MHz centered pulse. All animal experiments were conducted in accordance with protocols approved by the Sunnybrook and Women's College Health Science Centre Institutional Animal Care and Use Committee.

B. Results

Figure 30A:
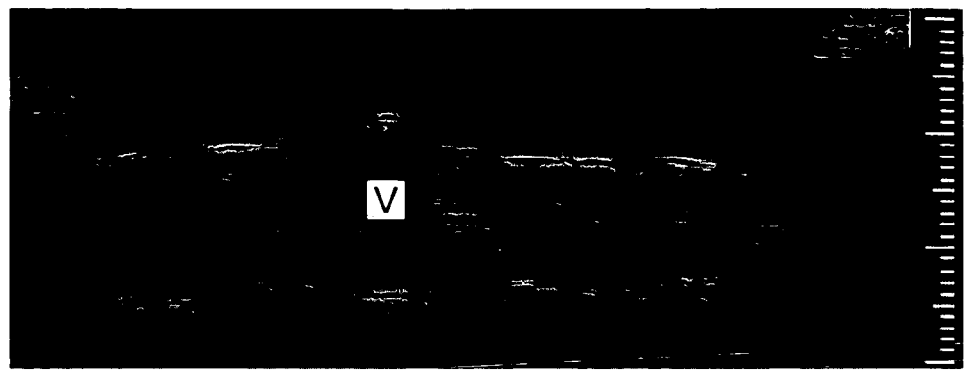
FIGS. 30a, b and c show In vivo demonstration of SH20 velocity in the microvasculature of a rabbit ear. a) A 19 MHz B-scan fundamental mode image of a rabbit ear in cross section, where the presence of a 300-400 μm diameter microvessel ('V') is evident. Linear 20 MHz PWD at a central position within the vessel (b). A SH20 inset velocity image (c) of the vessel region after the introduction of contrast. A velocity image can be formed, and the resulting velocities are comparable to those indicated by the PWD spectrum.
Figure 30B:
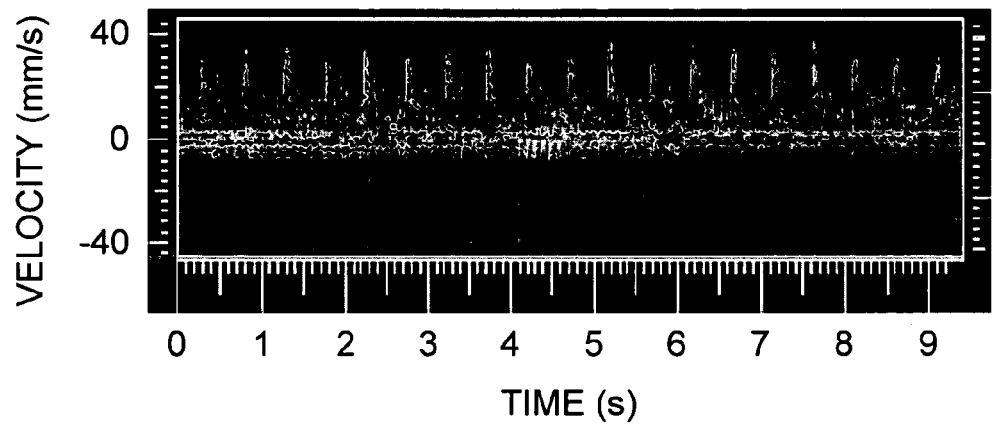
Figure 30C:
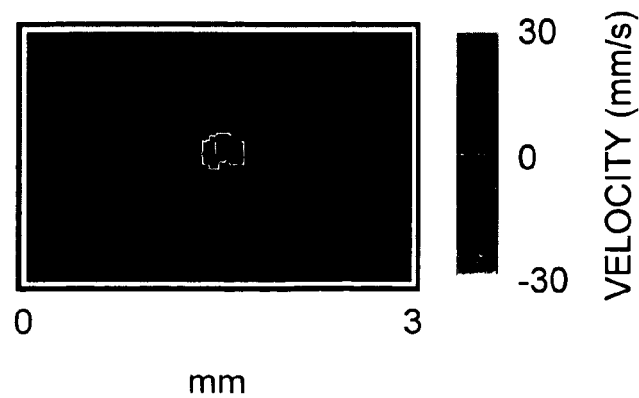

FIG. 30a shows a 19 MHz B-scan image of a rabbit ear in cross-section, where a 300-400 μm microvessel is evident. FIG. 30b is a 20 MHz pulsed-wave Doppler spectra from this vessel which shows the flow to be pulsatile, with peak velocities on the order of 20-35 mm/s. FIG. 30c is a color flow image of this vessel derived from the subharmonic signals. The estimated velocities are in a similar range to those indicated by PWD spectrum. These results provide an in vivo demonstration of velocity imaging using subharmonic emissions at ultrasound biomicroscopy frequencies.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

References

F. S. Foster, C. J. Pavlin, K. A. Harasiewicz, D. A. Christopher, and D. H. Turnbull, "Advances in ultrasound biomicroscopy", *Ultrasound Med. Biol.*, vol. 26, pp 1-27, 2000.

D. E. Goertz, J. L. Yu, R. S. Kerbel, P. N. Burns, and F. S. Foster, "High frequency 3D imaging of the microcirculation", *Ultrasound Med. Biol.*, vol 29., pp 39-51, 2003.

D. E. Goertz, "High frequency ultrasound imaging of the microcirculation", *PhD Thesis*, University of Toronto, 2002.

D. E. Goertz, S. W. S. Wong, E. Cherin, C. T. Chin, P. N. Burns, and F. S. Foster, "Non-linear scattering properties of microbubble contrast agents at high frequencies", *Proc. IEEE Ultrason. Symp.*, 2001.

D. E. Goertz, E. Cherin, A. Needles, R. Karshafian, A. Duckett, P. N. Burns, and F. S. Foster, "High frequency nonlinear b-scan and color flow imaging of microbubble contrast agents", presented at the 8$^{th}$ European Symposium on Ultrasound Contrast Imaging, January, 2003.

F. S. Foster, M. Y. Zhang, Y. Q. Zhou, G. Liu, J. Mehi, E. Cherin, K. S. Harasiewicz, B. G. Starkoski, L. Zan, D. A. Knapik, and L. Adamson, "A new instrument for in vivo microimaging of mice", *Ultrasound Med. Biol., pp.* 1165-1172, 2002.

M. D. Sherar, and F. S. Foster, "The design and fabrication of high frequency poly (vinylidene flouride) transducers, *Ultrason. Imaging*, vol. 11, pp. 75-94, 1989.

G. S. Kino, *Acoustic Waves: Devices, Imaging, and analog Signal Processing*, Prentice-Hall, New Jersey, 1987.

E. W. Cherin, J. K. Poulsen, A. F. W. van der Steen, et al., "Experimental characterization of fundamental and second harmonic beams for a high-frequency ultrasound transducer", *Ultrasound Med. Biol.*, vol. 28 (5), pp. 635-646, 2002.

T. L. Szabo, F. Clougherty, and C. J. Grossman. "Effects of nonlinearity on the estimation of in situ values of acoustic output parameters", *Ultrasound Med. Biol.*, vol. 18, pp. 33-41, 1999.

L. K. Ryan and F. S. Foster, "Tissue equivalent vessel phantoms for intravascular ultrasound", *Ultrasound in Medicine & Biology*, vol. 23, pp. 261-273, 1997.

C. T. Chin and P. N. Burns, "Experimental verification of ensemble model for scattering by microbubble population", *Proc. UFFC Symp.*, pp. 1827-1830, 1998.

D. Hope-Simpson, C. T. Chin, and P. N. Burns, "Pulse inversion Doppler: a new method for detecting non-linear echoes from microbubble contrast agents," *Ultrason., Ferroelec, Freq. Contr.*, vol. 46, pp. 372-382, 1999.

X. Deng, F. L. Lizzi, R. H. Silverman, R. Ursea, and D. J. Coleman, "Imaging and spectrum analysis of contrast agents in the in vivo rabbit eye using very high frequency ultrasound," *Ultrasound Med. Biol., vol.* 24, pp. 383-394, 1998.

D. E. Goertz, E. Cherin, A. Needles, R. Karshafian, A. Duckett, P. N. Burns, and F. S. Foster, "High frequency nonlinear imaging of microbubble contrast agents," *Submitted to IEEE Trans. Ultrason., Ferroelec., Freq. Contr*. F. S. Foster, M. Y. Zhang, Y. Q. Zhou, G. Liu, J. Mehi, E. Cherin, K. S. Harasiewicz, B. G. Starkoski, L. Zan, D. A. Knapik, L. Adamson, "A new instrument for in vivo microimaging of mice," *Ultrasound Med. Biol., pp.* 1165-1172, 2002.

T. Loupas, J. E. Powers, and R. W. Gill, "An axial velocity estimator for ultrasound blood flow imaging based on a full evaluation of the Doppler equation using a 2-dimensional autocorrelation approach," *IEEE Trans. Ultrason., Ferroelec., Freq. Contr.*, vol. 42, pp. 672-688, 1995.

T. Loupas, R. B. Peterson, and R. W. Gill, "Experimental evaluation of velocity and power estimation for ultrasound blood flow imaging by means of a two-dimensional autocorrelation approach," *IEEE Trans. Ultrason., Ferroelec., Freq. Contr.*, vol. 42, pp. 689- 699, 1995.

X. Verbeek, L. A. F. Ledoux, P. J. Brands, et al., "Baseband velocity estimation for second-harmonic signals exploiting the invariance of the doppler equation," *IEEE T Bio-med. Eng.*, vol. 45 (10), pp. 1217-1226, October 1998.

F. Forsberg, W. T. Shi, and B. B. Goldberg, "Subharmonic imaging of contrast agents," *Ultrasonics*, vol. 38, pp. 93-98, March 2000.

Y.-S Lee and M. F. Hamilton, "Time-domain modeling of pulsed finite-amplitude sound beams," *J. Acoust. Soc. Amer.*, vol. 97, pp. 906-917, 1995.

What is claimed is:

1. An ultrasound imaging system, comprising:
a transmit subsystem configured to produce high frequency ultrasound energy at a center frequency of at least 25 MHz, wherein the transmit subsystem includes— a transmit oscillator configured to generate a transmit pulse having a pulse frequency centered at the center frequency and a pulse length of a predetermined number of cycles; and an external transducer electrically connected to the transmit oscillator and configured to transmit ultrasound energy based on the transmit pulse;

a receive subsystem configured to receive ultrasound echoes emission of the transmitted ultrasound energy scattered by a microbubble contrast agent, wherein the receive subsystem includes at least a first filter configured to filter the ultrasound echoes received at the transducer and output nonlinear ultrasound echoes in a frequency band of interest centered at a subharmonic frequency of the first frequency; and a processing system configured to produce an image from the filtered non-linear ultrasound echoes, wherein the processing system includes— a reference oscillator coupled to the transmit oscillator and configured to produce reference signals at the subharmonic frequency; and a demodulator coupled to the reference oscillator and configured to selectively demodulate the filtered non-linear ultrasound echoes.

2. The ultrasound imaging system of claim 1, wherein the image produced by the processing system is a B-Mode ultrasound image.

3. The ultrasound imaging system of claim 1, wherein the image produced by the processing system is a color flow ultrasound image.

4. The ultrasound imaging system of claim 1, wherein the image produced by the processing system is a pulsed wave Doppler spectrum.

5. The ultrasound imaging system of claim 1, wherein the image produced by the processing system is a power Doppler image.

6. The ultrasound imaging system of claim 1, wherein the received non-linear echoes include ultrasound energy at a sub-harmonic frequency of the transmitted frequency.

7. The ultrasound imaging system of claim 6, wherein the processing system is further configured to generate a blood velocity estimate from the nonlinear sub-harmonic frequency echoes.

8. The ultrasound imaging system of claim 1, wherein the received nonlinear ultrasound echoes include ultrasound energy at a second harmonic of the transmitted frequency.

9. The ultrasound imaging system of claim 6, wherein the high frequency ultrasound is transmitted at a fundamental center frequency of $f_{center}$, and the received non-linear ultrasound echoes include ultrasound energy having a frequency of $f_{center}/2$.

10. The ultrasound imaging system of claim 1, wherein the transducer is configured to transmit a plurality of high frequency ultrasound pulses and to receive non-linear ultrasound echoes of the transmitted ultrasound scattered by the microbubble contrast agent and wherein the processing system is configured to provide at least one velocity estimate from the filtered non-linear ultrasound echoes.

11. The ultrasonic imaging system of claim 10, wherein the processing system is further configured to produce a pulsed wave Doppler spectrum from the filtered nonlinear ultrasound echoes.

12. The ultrasound imaging system of claim 10, wherein the high frequency ultrasound is transmitted at a fundamental center frequency of $f_{center}$, and the filtered non-linear sound echoes have a frequency of $f_{center}/2$.

13. The ultrasound imaging system of claim 12, wherein the processing system is configured to produce a color flow image.

14. The ultrasound imaging system of claim 1, wherein the ultrasound transducer has only a single element for transmitting and receiving sound.

15. The ultrasound imaging system of claim 1, wherein the microbubble contrast agent is located within a living subject.

16. The ultrasound imaging system of claim 15, wherein the subject is a small animal.

17. The ultrasound imaging system of claim 16, wherein the small animal is a mouse or a rat.

18. A method for producing an ultrasound image, comprising:

administering a plurality of microbubbles to a subject;

transmitting high frequency ultrasound at a center frequency of at least 25 MHz into the subject;

receiving ultrasound echoes of the transmitted ultrasound scattered by at least one administered microbubble located within the subject, wherein the receiving includes applying a first filter to remove linear signals from the ultrasound echoes; and processing the non-linear ultrasound echoes to produce an image, wherein the processing includes— producing a first reference signal and a second reference signal at a subharmonic frequency of the transmitted center frequency; and selectively demodulating the filtered non-linear ultrasound echoes using the first reference signal and the second reference signal.

19. The method of claim 18, wherein the subject is a small animal.

20. The method of claim 19, wherein the small animal is a mouse or a rat.

21. The method of claim 18, wherein the image produced is a B-Mode ultrasound image.

22. The method of claim 18, wherein the image produced is a color flow ultrasound image.

23. The method of claim 18, wherein the image is a pulsed wave Doppler spectrum.

24. The method of claim 18, wherein the image is a power Doppler image.

25. The method of claim 18, wherein the received non-linear echoes include ultrasound energy at a sub-harmonic frequency of the transmitted frequency.

26. The method of claim 25, further comprising generating a blood velocity estimate from the received non-linear sub-harmonic frequency echoes.

27. The method of claim 18, wherein the received non-linear echoes include ultrasound energy at a second harmonic of the transmitted frequency.

28. The method of claim 18, wherein the high frequency ultrasound is transmitted at a fundamental center frequency of $f_{center}$, and the received non-linear sound echoes have a frequency of $f_{center}/2$.

29. The method of claim 18, wherein a plurality of high frequency ultrasound pulses are transmitted into the subject and a plurality of non-linear sound echoes of the transmitted ultrasound scattered by a microbubble contrast agent are received, and wherein at least one velocity estimate is produced from the received non-linear echoes.

30. The method of claim 29, wherein a pulsed wave Doppler spectrum is produced from the received non-linear echoes.

31. The method of claim 29, wherein the high frequency ultrasound is transmitted at a fundamental center frequency of $f_{center}$, and the received non-linear sound echoes have a frequency of $f_{center}/2$.

32. The method of claim 31, wherein the received non-linear sound echoes are used to produce a color flow ultrasound image.

33. The system of claim 1 wherein at least 20% by volume of microbubbles in the microbubble contrast agent have a size of less than 1 micron.

34. The method of claim 18 wherein at least 20% by volume of the microbubbles have a size of less than 1 micron.

35. The method of claim 18 further comprising applying a second filter to the ultrasound echoes to remove ultrasound energy outside of a frequency range of interest, approximately centered at the subharmonic frequency.

\* \* \* \* \*